United States Patent
Mort et al.

(10) Patent No.: US 10,266,814 B2
(45) Date of Patent: Apr. 23, 2019

(54) SYSTEMS AND METHODS FOR PRODUCTION AND USE OF FUNGAL GLYCOSYL HYDROLASES

(71) Applicant: THE BOARD OF REGENTS FOR OKLAHOMA STATE UNIVERSITY, Stillwater, OK (US)

(72) Inventors: Andrew Mort, Stillwater, OK (US); Anamika Ray, Torrance, CA (US); Sayali S. Saykhedkar, Hatboro, PA (US); Rolf A. Prade, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 15/315,484

(22) PCT Filed: Jun. 2, 2015

(86) PCT No.: PCT/US2015/033791
§ 371 (c)(1),
(2) Date: Dec. 1, 2016

(87) PCT Pub. No.: WO2015/187697
PCT Pub. Date: Dec. 10, 2015

(65) Prior Publication Data
US 2017/0198270 A1    Jul. 13, 2017

Related U.S. Application Data

(60) Provisional application No. 62/006,410, filed on Jun. 2, 2014.

(51) Int. Cl.
| | |
|---|---|
| *C12N 9/02* | (2006.01) |
| *C12N 9/42* | (2006.01) |
| *C12P 19/02* | (2006.01) |
| *C12P 19/14* | (2006.01) |
| *C12N 9/24* | (2006.01) |
| *C12P 19/00* | (2006.01) |

(52) U.S. Cl.
CPC ......... *C12N 9/2402* (2013.01); *C12N 9/0083* (2013.01); *C12N 9/24* (2013.01); *C12N 9/2437* (2013.01); *C12P 19/02* (2013.01); *C12P 19/14* (2013.01); *C12P 2203/00* (2013.01)

(58) Field of Classification Search
None
See application file for complete search history.

(56) References Cited

U.S. PATENT DOCUMENTS

2014/0030769 A1    1/2014  Resch et al.

OTHER PUBLICATIONS

MYCOTA entry for Aspergillu nidulans, http://mycota-crcc.mnhn.fr/site/specie.php?idE=93#ancre13, retrieved on Feb. 23, 2018 (Year: 2018).*
Saykhedkar, et al., "A Time Course Analysis of the Extracellular Proteome of Aspergillus Nidulans Growing on Sorghum Stover", 2012, pp. 1-17, vol. 5, No. 52, Publisher: Biotechnology for Biofuels, Published in: US.
PCT/US2015/033791; Filed: Jun. 2, 2015; International Search Report and Written Opinion, Applicant: The Board of Regents for Oklahoma State University; dated Nov. 24, 2015.

* cited by examiner

*Primary Examiner* — Rebecca E Prouty
(74) *Attorney, Agent, or Firm* — Crowe & Dunlevy; Terry L. Watt

(57) ABSTRACT

Compositions comprising glycosyl hydrolase enzymes are provided, as are methods for their use to depolymerize hemicellulose, cellulose, lignin and pectin in biomass in order to produce products such as simple sugars. The enzymes, isolated from *Aspergillus nidulans* and *Phanerochaete chrysosporium*, were characterized, and synergistic mixtures of the enzymes were produced and used to generate simple sugars from biomass without the need to pretreat the biomass before digestion. The enzyme blends generally comprise two or more enzymes, which may be from the same fungus or from two different fungi, and are used for efficient and cost effective complete degradation of lignocelluloses. Applications of this technology include biofuel production.

3 Claims, 23 Drawing Sheets

Specification includes a Sequence Listing.

A.
B.
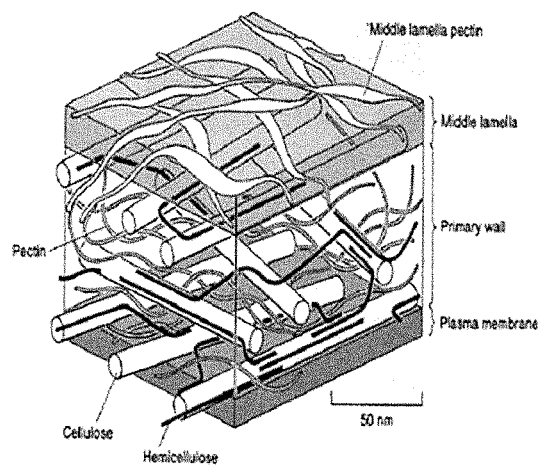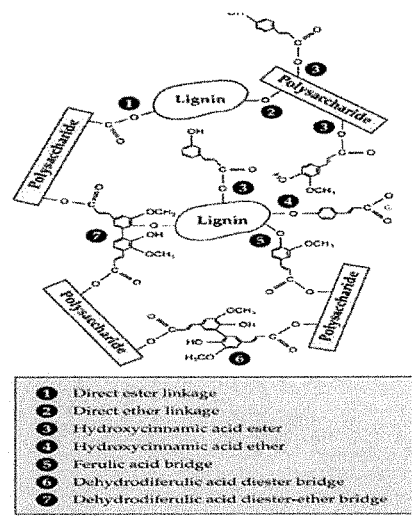
Figure 1 A and B

FaeEZY feruloyl esterase 813 bp

ATGCTTCGTGCTGTTCTTCTTCCTACACTTCTTGCTTTCGGCGCTTTCACACCTGTTCATGGCGCTAACTCTCCTGGCTGCGGCAAACA
ACCTACACTTACAAACGGCGTTAACCAAATCAACGGCCGTGAATACGTTCTTAAAATCCCTGATGGCTACGATCCTTCTAAACCTCAT
CATCTTATCTTCGGCCTTCATTGGCGTGGCGGCAACATGTACAACGTTGTTAACGGCGATTCTATCCAACCTTGGTACGGCCTTGAAG
CTCGTGCTCAAGGCTCTGCTATCTTCGTTGCTCCTAACGGCCTTAACGCTGGCTGGGCTAACACAAACGGCGAAGATGTTGCTTTCA
TCGATGCTATCATGGAACAAGTTGAAGATGATCTTTGCGTTGATCAAGCTTCTCGTTTCGCTACAGGCTTCTCTTGGGGCGGCGGCAT
GTCTTACGCTCTTGCTTGCGCTCGTGCTGCTGAATTCCGTGCTGTTTCTGTTCTTTCTGGCGGCCTTATCTCTGGCTGCGATGGCGGC
AACGATCCTATCGCTTACCTTGGCATCCATGGCATCAACGATCCTGTTCTTCCTCTTGATGGCGGCGTTACACTTGCTAACACATTCGT
TTCTAACAACGGCTGCCAACCTACAGATATCGGCCAACCTGCTTCTGGCTCTGGCGGCTCTGTTCGTACAGATTTCTCTGGCTGCTCT
CATCCTGTTTCTTTCATCGCTTACGATGGCGGCCATGATGGCGCTCCTCTTGGCGTTGGCTCTTCTCTTGCTCCTGATGCTACATGGG
AATTCTTCATGGCTGCTTGA (SEQ ID NO: 1)

CelEZY cellulase 1290 bp

ATGGCTCTTCTTCTTTCTCTTTCTCTTCTTGCTACAACAATCTCTGCTCAACAAATCGGCACACCTGAAATCCGTCCTCGTCTTACAACA
TACCATTGCACATCTGCTAACGGCTGCACAGAACAAAACACATCTGTTGTTCTTGATGCTGCTACACATCCTATCCATGATGCTTCTAA
CCCTTCTGTTTCTTGCACAACATCTAACGGCCTTAACCCTGCTCTTTGCCCTGATAAACAAACATGCGCTGATAACTGCGTTATCGATG
GCATCACAGATTACGCTGCTCATGGCGTTGAAACACATGGCTCTCGTCTTACACTTACACAATACCGTAACGTTAACGGCGCTCTTTC
TTCTGTTTCTCCTCGTGTTTACCTTGTTGATGAATCTGATCCTGATGAACAAGAATACCGTGCTCTTTCTCTTCTTGCTCAAGAATTCACA
TTCACAGTTAACGTTTCTGCTCTTCCTTGCGGCATGAACGGCGCTCTTTACCTTTCTGAAATGTCTCCTTCTGGCGGCCGTTCTGCTCT
TAACCCTGCTGGCGCTTCTTACGGCACAGGCTACTGCGATGCTCAATGCTACGTTAACCCTTGGATCAACGGCGAAGGCAACATCA
ACGGCTACGGCGCTTGCTGCAACGAAATGGATATCTGGGAAGCTAACTCTCGTTCTACAGGCTTCACACCTCATGCTTGCCTTTACG
AACCTGAAGAAACAGAAGGCCGTGGCGTTTACGAATGCGCTTCTGAAGATGAATGCGATTCTGCTGGCGAAAACGATGGCATCTGC
GATAAATGGGGCTGCGGCTTCAACCCTTACGCTCTTGGCAACACAGAATACTACGGCCGTGGCCAAGGCTTCGAAGTTGATACAAA
AGAACCTTTCACAGTTGTTACACAATTCCTTACAGATGATGGCACATCTACAGGCGCTCTTACAGAAATCCGTCGTCTTTACATCCAAA
ACGGCCAAGTTATCGAAAACGCTGTTGTTTCTTCTGGCGCTGATTCTCTTACAGATTCTCTTTGCGCTTCTACAGCTTCTTGGTTCGATT
CTTACGGCGGCATGGAAGGCATGGGCCGTGCTCTTGGCCGTGGCATGGTTCTTGCTATGTCTATCTGGAACGATGCTGGCGGCTAC
ATGCAATGGCTTGATGGCGGCGATGCTGGCCCCTTGCAACGCTACAGAAGGCGCTCCTGAATTCATCGAAGAACATACACCTTGGAC
ACGTGTTGTTTTCGAAGATCTTAAATGGGGCGATATCGGCTCTACATTCCAAGCTTGA (SEQ ID NO: 2)

Figure 7A

CdhEZY cellobiose dehydrogenase 2343 bp

ATGCATTCTTTCCTTCGTTCTTTCGCTGCTCTTGTTGCTGCTGGCTCTGATCCTGATACAGGCATCGTTTTCGATACATGGACAGTTGAA
GCTTCTTCTTCTTCTGCTGGCTTCACATTCGGCGTTTCTCTTCCTGAAGATGCTCTTGATACAGATGCTACAGAATTCATCGGCTACCTT
TCTTGCTCTTCTTCTTCTACATCTGAATTCACAGGCTGGTGCGGCCTTTCTATGGGCTCTTCTATGAACTCTAACCTTCTTCTTGTTGCTT
ACGCTCAAGATGATACAGTTCTTACATCTTTCCGTTTCTCTTCTGGCTACGCTATGCCTTCTGTTTACTCTGGCAACGCTACACTTACAC
AAATCTCTTCTACAGTTACAGCTGATAAATTCGAAGTTCTTTTCCGTTGCGAAGAATGCCTTCGTTGGGATCATGAAGGCGTTTCTGGC
TCTGCTACAACATCTGCTGGCCAACTTATCCTTGCTTGGGCTCAAGCTGAAGAATCTCCTACAAACGCTGATTGCCCTGATGATCTTT
CTCTTGTTCAACATGAAGCTCAAGGCATCTGGGTTGGCAAACTTTCTGGCGATGCTGCTACATCTAACTACGAAACATGGGCTGCTCT
TGCTACAAACGTTGTTGATGGCACATGCGGCACAGATGGCGGCGGCGGCGGCGATAACGGCAACGGCACAACACCTGGCGTTCC
TGTTCCTACAAACGTTACATACGATTACATCATCGTTGGCTCTGGCCCTGCTGGCATGGTTCTTGCTGATCGTCTTTCTGAAGCTGGC
GCTAAAACACTTCTTATCGAAAAAGGCCCTCCTTCTATCGGCCTTTGGAACGGCACAATGAAACCTGATTGGCTTAACGGCACAGAT
CTTACACGTTTCGATGTTCCTGGCCTTTGCAACGAAATCTGGAAAAACTCTGATGGCATCGCTTGCCCTGATAACGATCAAATGGCTG
GCTGCCTTGTTGGCGGCGGCACAGCTGTTAACTCTGGCCTTTGGTGGAAACCTTACTCTAAAGATTTCGATGAATCTTTCCCTGAAAC
ATGGAAATACGATGATGTTCGTGATGCTGTTACACGTGTTTTCACACGTATCCCTGGCACAACAACACCTTCTACAGATAACCGTCTTT
ACCTTGCTGAAGGCCCTTCTGTTATCATGAACGGCCTTCTTGCTTCTGGCTGGAAAGGCACAACATTCAACGATGAACCTGAAGAAA
AATACAAATCTGTTGGCTACTCTCCTTACATGTTCTCTCATGGCCAACGTAACGGCCCTATGGCTACATACCTTCTTGATGCTTACCAA
CGTCCTAACTTCGATCTTTGGGTTAACACAGTTGTTCGTCGTGTTGTTCGTGATGGCGCTACAGTTACAGGCGTTGAAGTTGAACCTTT
CAACGATGGCGGCTACGAAGGCTCTCTTCAACTTAACGAAGGCGGCCGTGTTATCCTTTCTGCTGGCGCTTTCGGCACACCTAAAAT
CCTTTTCCGTTCTGGCATCGGCCCTGAAGATCAACTTGCTATCGTTAACGGCTCTGCTTCTGATGGCGAAACAATGATCTCTGAAGAT
CAATGGATCAACCTTCCTGTTGGCGAAAACCTTATGGATCATCCTAACACAGAAATCGTTGTTCAACATCCTGATGTTGTTTTCTACGA
TTACTACGCTGCTTACGATGATCCTATCGAAGCTGATGCTCAATCTTACCTTGTTAACCGTACAGGCCCTCTTGCTCAATCTGCTCCTA
ACGTTAACCCTGTTTTCTTCGATCAAGTTACAGGCTCTGATAACGTTACACGTCAACTTCAATACCAAGCTCGTGTTGAAGGCTCTCAT
AACGTTGCTGATGGCCATACAATCTCTATCTCTCAATACGTTGGCCGTGGCCAAACATCTCGTGGCAAACTTACAATCACATCTGCTC
TTAACACAGTTGTTTCTACACTTCCTTGGCTTCAAGATGATAACGATACAGATGCTGTTATCGCTGGCCTTGAACGTCTTCGTGATTCT
CTTTCTACAATCCAAGGCCTTACATGGGCTTACCCTAAAGCTAACGTTTCTATGGCTGAACATGTTAACTCTATGGCTAAAACAGGCC
GTGGCTCTAACCATTGGATGGGCTCTTGCAAAATGGGCCCTGATGATGGCCGTGATGGCGGCTCTTCTGTTGTTGATCTTAACACAA
AAGTTTACGGCATGGATAACCTTTTCGTTGTTGATGCTTCTATCTTCCCTGGCATGATCTCTACAAACCCTTCTGCTTACATCACAGTTG
TTGCTGAACGTGCTGCTGAACGTATCCTTGCTCTTCAAGGCTGA (SEQ ID NO: 3)

Figure 7B

CbcEZY cellulose 1,4-beta-cellobiosidase 1593 bp

ATGGCTTCTTCTTTCCAACTTTACAAAGCTCTTCTTTTCTTCTCTTCTCTTCTTTCTGCTGTTCAAGCTCAAAAAGTTGGCACACAACAAG
CTGAAGTTCATCCTGGCCTTACATGGCAAACATGCACATCTTCTGGCTCTTGCACAACAGTTAACGGCGAAGTTACAATCGATGCTAA
CTGGCGTTGGCTTCATACAGTTAACGGCTACACAAACTGCTACACAGGCAACGAATGGGATACATCTATCTGCACATCTAACGAAGT
TTGCGCTGAACAATGCGCTGTTGATGGCGCTAACTACGCTTCTACATACGGCATCACAACATCTGGCTCTTCTCTTCGTCTTAACTTC
GTTACACAATCTCAACAAAAAAACATCGGCTCTCGTGTTTACCTTATGGATGATGAAGATACATACACAATGTTCTACCTTCTTAACAAA
GAATTCACATTCGATGTTGATGTTTCTGAACTTCCTTGCGGCCTTAACGGCGCTGTTTACTTCGTTTCTATGGATGCTGATGGCGGCAA
ATCTCGTTACGCTACAAACGAAGCTGGCGCTAAATACGGCACAGGCTACTGCGATTCTCAATGCCCTCGTGATCTTAAATTCATCAAC
GGCGTTGCTAACGTTGAAGGCTGGGAATCTTCTGATACAAACCCTAACGGCGGCGTTGGCAACCATGGCTCTTGCTGCGCTGAAAT
GGATATCTGGGAAGCTAACTCTATCTCTACAGCTTTCACACCTCATCCTTGCGATACACCTGGCCAAACACTTTGCACAGGCGATTCT
TGCGGCGGCACATACTCTAACGATCGTTACGGCGGCACATGCGATCCTGATGGCTGCGATTTCAACTCTTACCGTCAAGGCAACAA
AACATTCTACGGCCCTGGCCTTACAGTTGATACAAACTCTCCTGTTACAGTTGTTACACAATTCCTTACAGATGATAACACAGATACAG
GCACACTTTCTGAAATCAAACGTTTCTACGTTCAAAACGGCGTTGTTATCCCTAACTCTGAATCTACATACCCTGCTAACCCTGGCAAC
TCTATCACAACAGAATTCTGCGAATCTCAAAAAGAACTTTTCGGCGATGTTGATGTTTTCTCTGCTCATGGCGGCATGGCTGGCATGG
GCGCTGCTCTTGAACAAGGCATGGTTCTTGTTCTTTCTCTTTGGGATGATAACTACTCTAACATGCTTTGGCTTGATTCTAACTACCCTA
CAGATGCTGATCCTACACAACCTGGCATCGCTCGTGGCACATGCCCTACAGATTCTGGCGTTCCTTCTGAAGTTGAAGCTCAATACC
CTAACGCTTACGTTGTTTACTCTAACATCAAATTCGGCCCTATCGGCTCTACATTCGGCAACGGCGGCGGCTCTGGCCCTACAACAA
CAGTTACAACATCTACAGCTACATCTACAACATCTTCTGCTACATCTACAGCTACAGGCCAAGCTCAACATTGGGAACAATGCGGCG
GCAACGGCTGGACAGGCCCTACAGTTTGCGCTTCTCCTTGGGCTTGCACAGTTGTTAACTCTTGGTACTCTCAATGCCTTCTTGAAGA
TGGCTGA (SEQ ID NO: 4)

XylEZY xylanase 928 bp

ATGGTTCATCTTAAAACACTTGCTGGCTCTGCTGTTTTCGCTTCTCTTGCTACAGCTGCTGTTCTTCCTCGTCAATCTGCTTCTCTTAAC
GATCTTTTCGTTGCTGCTGGCAAATCTTACTTCGGCACATGCTCTGATCAAGCTCTTCTTCAAAACTCTCAAAACGAAGCTATCGTTGC
TTCTCAATTCGGCGTTATCACACCTGAAAACTCTATGAAATGGGATGCTCTTGAACCTTCTCAAGGCAACTCGGCTGGTCTGGCGCTG
ATTACCTTGTTGATTACGCTACACAACATAACAAAAAAGTTCGTGGCCATACACTTGTTTGGCATTCTCAACTTCCTTCTTGGGTTTCTT
CTATCGGCGATGCTAACACACTTCGTTCTGTTATGACAAACCATATCAACGAAGTTGTTGGCCGTTACAAAGGCAAAATCATGCATTG
GGAGTTGTTAACGAAATCTTCAACGAAGATGGCACATTCCGTAACTCTGTTTTCTACAACCTTCTTGGCGAAGATTTCGTTCGTATCGC
TTTCGAAACAGCTCGTGCTGCTGATCCTGATGCTAAACTTTACATCAACGATTACAACCTTGATTCTGCTTCTTACGCTAAAACACAAG
CTATGGCTTCTTACGTTAAAAAATGGCTTGCTGAAGGCGTTCCTATCGATGGCATCGCTCTTTCTTCTCTTGCTAACACAGGCGTTTCT
GAAGTTGCTATCACAGAACTTGATATCGCTGGCGCTGCTTCTTCTGATTACCTTAACCTTCTTAACGCTTGCCTTAACGAACAAAAATG
CGTTGGCATCACAGTTTGGGGCGTTTCTGATAAAGATTCTTGGCGTGCTTCTGATTCTCCTCTTCTTTTCGATGGCAACTACCAACCTA
AAGATGCTTACAACGCTATCGTTAACGCTCTTTCTTGA (SEQ ID NO: 5)

Figure 7C

RhIEZY rhammnoglacturonan lyase 3126 bp

ATGTTCGCTTCTACACTTCGTAAAACATTCGTTTTCCTTGGCCTTGCTACATACTCTGCTGCTGCTCTTACAACAACATCTAACTCTACACATTACAC
AATCTCTAACTCTCGTTTCTCTGTTGCTGTTGCTAAATCTATAACGGCACAGATTCTACAGGCACACCTTACGTTGGCGTTATCATGACAGATACATA
CGAAACAACAAACCAAACACTTTCTCAATACCTTTTCCTTCGTGGCGAAGAAACAGGCCTTCATGCTTTCTCTCGTGTTACATACTACAACGAATCT
GATTACTTCCTTCGTGGCCTTGGCGAACTTCGTACACTTTTCCGTCCTAACACAAACCTTTGGACACATTTCTCTGGCTCTGAAGGCAACTACGGC
CCTATGCCTCTTTCTTCTACAGAAAAAATCACAGTTCAAGATGCTACAACATACCTTGGCGATACAACAGATGATCCTTACGTTTCTCAATACTCTGA
TTACTTCACAAAATACACACTTACAGAATCTTGGCGTGATCATGATGTTCATGGCCATTTCTCTAACGGCTCTACATCGGCGATGGCAACACATAC
GGCGCTTGGCTTGTTCATAACACACGTGAAACATACTACGGCGGCCCTCTTCATGCTGATCTTGTTGTTGATGGCATCGTTTACAACTACATCGTTT
CTGGCCATTACGGCGCTCCTAACCCTAACCTTACACATGGCTTCGATCGTACATTCGGCCCTCAATACTACCATTTCAACTCTGGCGGCCCTGGC
ACAACACTTGAAGAACTTCGTGCTGATGCTGCTCAATACGCTTCTCCTGAATGGAACGCTGAATTCTACGATTCTATCGCTAAACATATCCCTAACT
ACGTTCCTTCTACAGGCCGTACAACATTCCGTGGCAAAGTTAACCTTCCTAAAGGCGCTAAAAAACCTATCATCGTTCTTTCTGAAAACGAACAAG
ATTTCCAACTTAACGTTTTCAAAAAAGATTCTCTTCAATACTGGGCTGAAATCGATGGCTCTGGCGCTTTCACAATCCCTCGTGTTGTTAAAGGCAC
ATACCGTGTTACAATCTACGCTGATGAAATCTTCGGCTGGTTCATCAAAGATAACGTTAAAGTTATCGGCTCTAACGCTCATACATTCACATGGAAA
GAAGAAACAGCTGGCAAAGAAATCTGGCGTATCGGCGTTCCTGATAAATCTTCTGGCGAATTCCTTCATGGCTACGCTCCTGATACATCTAAACCT
CTTCAACCTGAACAATACCGTATCTACTGGGGCAAATACGATTACCCTTCTGATTTCCCTGAAGGCGTTAACTACCATGTTGGCAAATCTGATCCTG
CTAAAGATCTTAACTACATCCATTGGTCTTTCTTCCCTTCTCAAGGCAACCATCTTCGTAACGAACCTTACTACCAAAACGTTAACAACTGGACAAT
CACATTCGATCTTACAGCTTCTCAACTTCGTAACACAAAAACAGCTACATTCACAGTTCAACTTGCTGGCACACGTAACGCTAACGGCAACTCTAA
ATGGAACCCTGATCCTGCTAAATACAACAACCTTCCTTGGACAGTTAACGTTAACGGCATCTACGAAGATACATGGGAAATCCCTTACTGGCGTTC
TGGCTCTTGCGGCGTTCGTTCTGGCGTTCAATGCCAAAACACAGAACATAAATTCGTTTTCGATGCTGGCAAACTTCGTAAAGGCCGTAACGAATT
CGTTCTTTCTCTTCCTTTCAACGCTACATCTGTTGAAACAGCTCTTCTTCCTAACTCTCTTTACGTTCAAGTTGTTTCTATGGAAGCTGTTTCTGTTTCT
AACGATATGCGTGTTCTTGTTCAAGCTTTCATGCCTCTTGTTACATGGGGCACAGCTGTTGAAAAACGTGTTCTTCTTACAGGCATCGTTTCTGTTTC
TGCTATGGCTAAAGAAGATTACCCTATGATCTCTCGTCCTTGCCCTCGTAAAGGCGGCACACGTCGTCGTAAAAAAGAACGTAAAAAAGAAGGCA
AAAAACAAGGCCGTACAGTTCTTGATGCTCTTCTTCAACGTTCTGAACAAGATTCTTTCTGGTCTCGTTTCTGCCGTTCTCCTATCGAATCTGTTGCT
CAATACGTTTACGGCCAAGGCTCTACAGCTCTTCGTAAAAAAACAACAGATAACCTTGTTCGTGTTGTTTGCGTTTCTGATACACATAACACAAAAC
CTAACCTTCCTGATGGCGATATCCTTATCCATGCTGGCGATCTTACAGAATCTGGCACAAAAGAAGAACTTGAAAACAAATCTACTGGCTTGATT
CTCAACCTCATCGTTACAAAATCGTTATCGCTGGCAACCATGAAACATTCCTTGATCGTAACTACCATTCTCATCATGGCAACGAACGTGTTACAAT
GGATTGGAAATCTCTTATCTACCTTGAAAACACATCTGCTATCCTTGATCTTGGCGCTGGCCATCAACTTAAAGTTTTCGGCTCTCCTTACACACCT
AAACATGGCAACGGCGCTTTCCAATACCCTCGTACAGATACAACAACATGGGAAGAAATCCCTAAAGATACAGATCTTCTTGTTACACATGGCCCT
CCTAAAGCTCATCTTGATCTTGGCCATCTTGGCTGCCGTGTTCTTCGTCAAGCTCTTTGGGAAATGGAATCTCGTCCTCTTCTTCATGTTTTCGGCC
ATATCCATGGCGGCTACGGCAAAGAAGTTGTTTGCTGGGATCTTTGCCAACGTGCTTACGAAGCTATCATGGATGGCGAATCTCGTTGGTGGAAC
CTTTGCGTTCTTTTCTACTGCTGGATCCTTCGTCTTTTCTTCGATTGGACAGCTGATGGCCGTGCTACAGTTCTTGTTAACGCTGCTACAGTTGGCG
GCGTTCGTGATCTTAAACGTCGTGAAGCTATCTGCGTTGATATCCAAGCTGGCTCTAAACGTTTCCTTTCTGGCTGCACATGA (SEQ ID NO: 6)

Figure 7D

RhaEZY rhammnoglacturonan acetylesterase 738 bp

ATGAAATCTATCGCTCTTACATCTCTTTCTCTTCTTCCTTCTGCTCTTGCTCAAACAATCTACCTTGCTGGCGATTCTACAATGGCTTCTT
CTACACCTGGCTGGGGCGATTACATCGCTGATTCTGTTTCTGTTGAAATCTCTAACCAAGCTATCGGCGGCCGTTCTGCTCGTTCTTA
CACACGTGAAGGCCGTTTCCAAGCTATCGCTGATGTTCTTCAAGCTGGCGATTACGTTGTTATCGAATTCGGCCATAACGATGGCGG
CTCTCTTTCTAACGATAACGGCCGTACAGATTGCCCTGGCGATGGCGATGAAACATGCGAAACAGTTTACAACGGCGTTGCTGAAAC
AGTTCTTACATTCCCTGCTTACATCGAAAACGCTGCTCTTCTTTTCCTTGAAAAAGGCGCTAACGTTCTTATCTCTTCTCAAACACCTAA
CAACCCTTGGGAATCTGGCACATTCTCTTACACACCTAACCGTTTCGTTGGCTACGCTGAACTTGCTGCTCAACGTGCTGGCGTTGAT
TACGTTGATCATGGCGCTTACACAGCTTCTATCTTCGAAGCTCTTGGCGCTGATACAGTTAACTCTTTCTACCCTAACGATCATACACA
TACAAACGCTGAAGGCTCTTCTGTTGTTGCTGATGCTTTCCTTAAAGCTGTTGTTTGCTCTGGCGTTGCTCTTAACGATGTTCTTACACG
TACAGATTTCGATGGCGAATGCCTTTGA (SEQ ID NO: 7)

EglEZY endoglucanase 981 bp

ATGCGTTCTCTTGTTCTTCTTTCTTCTGTTCTTGCTCTTGTTGCTCCTTCTAAAGGCGCTTTCACATGGCTTGGCACAAACGAAGCTGGC
GCTGAATTCGGCGAAGGCTCTTACCCTGGCGAACTTGGCACAGAATACATCTGGCCTGATCTTGGCACAATCGGCACACTTCGTAAC
GAAGGCATGAACATCTTCCGTGTTGCTTTCTCTATGGAACGTCTTGTTCCTGATTCTCTTGCTGGCCCTGTTGCTGATGAATACTTCCA
AGATCTTGTTGAAACAGTTAACGGCATCACAGCTCTTGGCGCTTACGCTGTTCTTGATCCTCATAACTACGGCCGTTACTACGGCAAC
ATCATCACATCTACAGATGATTTCGCTGCTTTCTGGACAATCCTTGCTACAGAATTCGCTTCTAACGAACTTGTTATCTTCGATACAAAC
AACGAATACCATACAATGGATCAATCTCTTGTTCTTAACCTTAACCAAGCTGCTATCGATGCTATCCGTGCTTCTGGCGCTACATCTCA
ATACATCTTCGCTGAAGGCAACTCTTGGACAGGCGCTTGGACATGGGTTGATGTTAACGATAACATGAAAGCTCTTACAGATCCTCAA
GATAAACTTATCTACGAAATGCATCAATACCTTGATTCTGATGGCTCTGGCACAAACACAGCTTGCGTTTCTTCTACAATCGGCTCTGA
ACGTGTTACAGCTGCTACAAACTGGCTTCGTGAAAACGGCAAACTTGGCGTTCTTGGCGAATTCGCTGGCGCTAACAACCAAGTTTG
CAAAGATGCTGTTGCTGATCTTCTTGAATACCTTGAAGAAAACTCTGATGTTTGGCTTGGCGCTCTTTGGTGGCTGCTGGCCCTTGG
TGGGGCGATTACATGTTCAACATGGAACCTACATCTGGCATCGCTTACCAAGAATACTCTGAAATCCTTCAACCTTACTTCGTTGGCT
CTCAATGA (SEQ ID NO: 8)

Figure 7E

ManEZY mannanase 1152 bp

ATGAAATTCTCTCAAGCTCTTCTTTCTCTTGCTTCTCTTGCTCTTGCTGCTGCTCTTCCTCATGCTTCTACACCTGTTTACACACCTTCTA
CAACACCTTCTCCTACACCTACACCTTCTGCTTCTGGCTCTTTCGCTACAACATCTGGCATCCAATTCGTTATCGATGGCGAAGCTGG
CTACTTCCCTGGCTCTAACGCTTACTGGATCGGCTTCCTTAAAAACAACTCTGATGTTGATCTTGTTTTCGATCATATGGCTTCTTCTGG
CCTTCGTATCCTTCGTGTTTGGGGCTTCAACGATGTTAACACAGCTCCTACAGATGGCTCTGTTTACTTCCAACTTCATCAAGATGGCA
AATCTACAATCAACACAGGCAAAGATGGCCTTCAACGTCTTGATTACGTTGTTCATTCTGCTGAAAAACATGGCATCAAACTTATCATC
AACTTCGTTAACTACTGGGATGATTACGGCGGCATGAACGCTTACATGCGTGCTTACGCGGCGGCGATAAAGCTGATTGGTTCGAA
AACGAAGGCATCCAAGCTGCTTACCAAGCTTACGTTGAAGCTGTTGTTAAACGTTACATCAACTCTACAGCTGTTTTCGCTTGGGAAC
TTGCTAACGAACCTCGTTGCACAGGCTGCGAACCTTCTGTTCTTCATAACTGGATCGAAAAACATCTGCTTTCATCAAAGGCCTTGAT
GAAAAACATCTTGTTTGCATCGGCGATGGCTCTGATGGCTCTTACCCTTTCCAATACACAGAAGGCTCTGATTTCGCTGCTGCTCTTA
CAATCGATACAATCGATTTCGGCACATTCCATCTTTACCCTGATTCTTGGGGCACAAACAACGATTGGGGCAAACTTTGGATCACATC
TCATGCTGCTGCTTGCGCTGCTGCTGGCAAACCTTGCCTTTTCGAAGAATACGGCGTTACATCTAACCATTGCGCTATCGAAAAACAA
TGGCAAAACGCTGCTCTTAACGCTACAGGCATCGCTGCTGATCTTTACTGGCAATACGGCGATACACTTTCTTCTGGCCCTTCTCCTG
ATGATGGCAACACATTCTACTACGGCTCTGAAGAATTCGAATGCCTTGTTACAAACCATGTTGAAACAATCGAACGTTCTGCTAAATG
A (SEQ ID NO: 9)

CbhEZY cellobiohydrolase 1353 bp

ATGCATTACTCTGCTTCTGGCCTTGCTCTTGCTTTCCTTCTTCCTGCTATCCAAGCTCAACAAACACTTTACGGCCAATGCGGCGGCTC
TGGCTGGACAGGCGCTACATCTTGCGTTGCTGGCGCTGCTTGCTCTACACTTAACCAATGGTACGCTCAATGCCTTCCTGCTGCTAC
AACAACATCTACAACACTTACAACAACAACATCTTCTGTTACAACAACATCTAACCCTGGCTCTACAACAACAACATCTTCTGTTACAG
TTACAGCTACAGCTTCTGGCAACCCTTTCTCTGGCTACCAACTTTACGTTAACCCTTACTACTCTTCTGAAGTTCAATCTATCGCTATCC
CTTCTCTTACAGGCACACTTTCTTCTCTTGCTCCTGCTGCTACAGCTGCTGCTAAAACACGTGATGTTGCTGCTAAAGTTCCTACAATG
GCTACATACCTTGCTGATATCCGTTCTCAAAACGCTGCTGGCGCTAACCCTCCTATCGCTGGCCAATTCGTTGTTTACGATCTTCCTG
ATCGTGATTGCGCTGCTCTTGCTTCTAACGGCGAATTCGCTATCTCTGATGGCGGCGTTCAACATTACAAAGATTACATCGATTCTATC
CGTGAAATCCTTGTTGAATACTCTGATGTTCATGTTATCCTTGTTATCGAACCTGATTCTCTTGCTAACCTTGTTACAAACCTTAACGTTG
CTAAATGCGCTAACGCTCAATCTGCTTACCTTGAATGCACAAACTACGCTGTTACACAACTTAACCTTCCTAACGTTGCTATGTACCTT
GATGCTGGCCATGCTGGCTGGCTTGGCTGGCCTGCTAACCTTCAACCTGCTGCTAACCTTTACGCTGGCGTTTACTCTGATGCTGGC
TCTCCTGCTGCTCTTCGTGGCCTTGCTACAAACGTTGCTAACTACAACGCTTGGGCTATCGATACATGCCCTTCTTACACACAAGGCA
ACTCTGTTTGCGATGAAAAAGATTACATCAACGCTCTTGCTCCTCTTCTTCGTGCTCAAGGCTTCGATGCTCATTTCATCACAGATACA
GGCCGTAACGGCAAACAACCTACAGGCCAACAAGCTTGGGGCGATTGGTGCAACGTTATCGGCACAGGCTTCGGCGCTCGTCCTT
CTACAAACACAGGCGATTCTCTTCTTGATGCTTTCGTTTGGGTTAAACCTGGCGGCGAATCTGATGGCACATCTGATACATCTGCTGC
TCGTTACGATGCTCATTGCGGCTACTCTGATGCTCTTCAACCTGCTCCTGAAGCTGGCACATGGTTCCAAGCTTACTTCGTTCAACTTC
TTCAAAACGCTAACCCTTCTTTCTGA (SEQ ID NO: 10)

CutEZY cutinase 774 bp

ATGCATTTCAAACTTCTTTCTCTTGCTGCTCTTGCTGGCCTTTCTGTTGCTTCTCCTCTTAACCTTGATGAACGTCAACATGCTGTTGGC
TCTTCTTCTGGCAACGATCTTCGTGATGGCGATTGCAAACCTGTTACATTCATCTTCGCTCGTGCTTCTACAGAACCTGGCCTTCTTGG
CATGTCTACAGGCCCTGCTGTTTGCAACGATCTTAAAGCTGATGCTTCTCTTGGCGGCGTTGCTTGCCAAGGCGTTGGCCCTAAATA
CACAGCTGGCCTTGCTGAAAACGCTCTTCCTCAAGGCACATCTTCTGCTGCTATCAACGAAGCTAAAGAACTTTTCGAACTTGCTGCT
TCTAAATGCCCTGATACACGTATCGTTGCTGGCGGCTACTCTCAAGGCACAGCTGTTATGCATGGCGCTATCCCTGATCTTTCTGATG
AAATCAAAGATAAAATCGCTGGCGTTGTTCTTTTCGGCGATACACGTAACAAACAAGATGGCGGCCAAATCAAAAACTTCCCTAAAGA
TAAAATCAAAATCTACTGCGCTACAGGCGATCTTGTTTGCGATGGCACACTTGTTGTTACAGCTGCTCATTTCACATACGTTGCTAACA
CAGGCGAAGCTTCTAAATGGCTTGAACAACAACTTGCTTCTATGCCTGCTTCTACATCTACATCTTCTTCTTCTTCTTCTTCTTCTGC
TCCTGCTTCTCAAACATCTCAATCTTCTGGCCTTTCTTCTTGGTTCTCTGGCCTTGGCAACTGA (SEQ ID NO: 11)

RhgEZY rhamnogalacturonase 1554 bp

ATGTACGTTTCTCGTCTTCTTCTTTTCCTTGCTCCTCTTCTTGTTAAAGGCCAACTTTCTGGCTCTGTTGGCCCTCTTACATCTGTTTCTT
CTAAATCTCAAACAAAAACATGCAACGTTCTTGATTACGGCGCTGTTGCTGATAAATCTACAGATATCGGCCCTGCTCTTTCTTCTGCT
TGGGATGAATGCGCTGATGGCGGCGTTGTTCATATCCCTCCTGGCGATTACGCTATCGAAACATGGGTTAAACTTTCTGGCGGCAAA
GCTTGCGCTATCCAACTTGATGGCATCATCTACCGTACAGGCACAGATGGCGGCAACATGATCATGATCGAACATACATCTGATTTC
GAATTCTTCTCTTCTACATCTAAAGGCGCTTTCCAAGGCTACGGCTACGAATTCCATGCTAAAGGCTCTTCTGATGGCCCTCGTATCCT
TCGTCTTTACGATGTTTCTGATTTCTCTGTTCATGATGTTGCTCTTGTTGATTCTCCTCTTTTCCATTTCTCTATGGATACATGCTCTAACG
GCGAAGTTTACAACATGGCTATCCGTGGCGGCAACATGGGCGGCCTTGATGGCATCGATGTTTGGTCTACAAACGTTTGGATCCATG
ATGTTATCCATGCTGAACATTCTCCTTTCGATGCTCGTTCTGATCGTCTTCAATCTCCTTCTAAAAACATCCTTGTTGAAAACATCTACTG
CAACTGGTCTGGCGGCTGCGCTATGGGCTCTCTTGGCACAGATACAGATATCTCTGATATCGTTTACCGTAACGTTTACACATGGAAA
TCTAACCAAATGTACATGGTTAAATCTAACGGCGGCTCTGGCACAGTTTCTAACCTTGTTCTTGAAAACTTCATCGCTCGTGCTGATTC
TAAAGGCCATGGCAACGCTTACTCTCTTGATATCGATTCTGCTTGGTCTTCTATGTCTACAATCGAAGGCGATGGCGTTGAACTTAAAA
ACGTTACAATCCGTAACTGGAAAGGCACAGAAGCTGATGGCTCTCAACGTGGCCCTATCAAAGTTAAATGCGCTTCTGGCGCTCCTT
GCACAGATGTTACAGTTGAAGATTTCGCTATGTGGACAGAATCTGGCGATGAACAAACATACGTTTGCGAAAACGCTTTCGGCGATG
GCTTCTGCCTTGCTGATGGCGATGGCACATCTACATTCACAACAACACTTACAGCTTCTGCTGCTCCTTCTGGCTACTCTGCTCCTTCT
ATGGATGCTGATCTTGAAACAGCTTTCGGCACAGATTCTGAAATCCCTATCCCTACAATCCCTACATCTTTCTACCCTGGCGCTACAC
CTTACTCTGCTCTTGCTGGCGCTTCTGTTTCTTCTTCTCAAGTTCCTGCTGCTTCTTCTTCTGCTGAAGCTAAATTCGTTGCTTCTCCTGC
TACATCTTCTCCTACAGCTACATCTACAGCTATCTCTTCTGTTGATCCTGTTTCTGCTGCTACAACAACAGCTACATCTCATGGCCATG
CAAATCTCATCATAAACATCAATGCCGTGCTCATCGTCATTGA (SEQ ID NO: 12)

Figure 7G

GluEZY glucosidase 1857 bp

ATGCGTGTTGATTCTACAGTTCTTGCTCTTGTTGCTCTTGCTACAGATTGCCTTGGCCTTGCTATCAAATCTAACGAACCTGAACTTCTT
CGTCGTGATGCTCTTCCTATCTACAAAAACGCTTCTTACTGCGTTGATGAACGTGTTCGTGATCTTCTTTCTCGTATGACACTTGAAGA
AAAAGCTGGCCAACTTTTCCATAAACAACTTTCTGAAGGCCCTCTTGATGATGATTCTTCTGGCAACTCTACAGAAACAATGATCGGC
AAAAAACATATGACACATTTCAACCTTGCTTCTGATATCACAAACGCTACACAAACAGCTGAATTCATCAACCTTATCCAAAAACGTGC
TCTTCAAACACGTCTTGGCATCCCTATCACAATCTCTACAGATCCTCGTCATTCTTTCACAGAAAACGTTGGCACAGGCTTCCAAGCT
GGCGTTTTCTCTCAATGGCCTGAATCTCTTGGCCTTGCTGCTCTTCGTGATCCTCAACTTGTTCGTGAATTCGCTGAAGTTGCTCGTGA
AGAATACCTTGCTGTTGGCATCCGTGCTGCTCTTCATCCTCAAGTTGATCTTTCTACAGAACCTCGTTGGGCTCGTATCTCTGGCACAT
GGGGCGAAAACTCTACACTTACATCTGAACTTATCGTTGAATACATCAAAGGCTTCCAAGGCGAAGGCAAACTTGGCCCTAAATCTGT
TAAAACAGTTACAAAACATTTCCCTGGCGGCGGCCCTATGGAAAACGGCGAAGATTCTCATTTCTACTACGGCAAAAACCAAACATC
CCTGGCAACAACATCGATGAACATCTTATCCCTTTCAAAGCTGCTCTTGCTGCTGGCGCTACAGAAATCATGCCTTACTACTCTCGTC
CTATCGGCACAAACTGGGAAGCTGTTGGCTTCTCTTTCAACAAAGAAATCGTTACAGATCTTCTTCGTGGCGAACTTGGCTTCGATGG
CATCGTTCTTACAGATTGGGGCCTTATCACAGATACATACATCGGCAACCAATACATGCCTGCTCGTGCTTGGGGCGTTGAATACCTT
CTGAACTTCAACGTGCTGCTCGTATCCTTGATGCTGGCTGCGATCAATTCGGCGGCGAAGAACGTCCTGAACTTATCGTTCAACTTGT
TCGTGAAGGCACAATCTCTGAAGATCGTATCGATGTTTCTGTTGCTCGTCTTCTTAAAGAAAAATTCCTTCTTGGCCTTTTCGATAACCC
TTTCGTTAACGCTTCTGCTGCTAACAACATCGTTGGCAACGAACATTTCGTTAACCTTGGCCGTGATGCTCAACGTCGTTCTTACACAC
TTCTTACAAACAACCAAACAATCCTTCCTCTTGCTAAACCTGGCGAAGGCACACGTTTCTACATCGAAGGCTTCGATTCTGCTTTCATG
TCTGCTCGTAACTACACAGTTGTTAACACAACAGAAGAAGCTGATTTCGCTCTTCTTCGTTACAACGCTCCTTACGAACCTCGTAACG
GCACATTCGAAGCTAACTTCCATGCTGGCTCTCTTGCTTTCAACGCTACAGAAAAAGCTCGTCAAGCTAAAATCTACTCTTCTCTTCCT
ACAATCGTTGATATCATCCTTGATCGTCCTGCTGTTATCCCTGAAGTTGTTGAACAAGCTCAAGCTGTTCTTGCTTCTTACGGCTCTGAT
TCTGAAGCTTTCCTTGATGTTGTTTTCGGCGTTTCTAAACCTGAAGGCAAACTTCCTTTCGATCTTCCTCGTTCTATGGATGCTGTTGAA
GCTCAAGCTGAAGATCTTCCTTTCGATACAGAAAACCCTGTTTTCCGTTACGGCCATGGCCTTGAATACGAAGATAACTGA (SEQ ID NO: 13)

Figure 7H

PelEZY pectin lyase 1140 bp

ATGCGTCTTCATGCTCCTATCCTTTCTCTTCTTGCTGCTGCTGCTTCTACATCTGCTGCTGGCGTTACAGGCTCTGCTGAAGGCTTCGCTAAAGGC
GTTACAGGCGGCGGCTCTGCTACACCTGTTTACCCTTCTACAACAGCTGAACTTGTTTCTTACCTTGGCGATTCTTCTGCTCGTGTTATCGTTCTTA
CAAAAACATTCGATTTCACAGGCACAGAAGGCACAACAACAGAAACAGGCTGCGCTCCTTGGGGCACAGCTTCTGCTTGCCAAGTTGCTATCAA
CAAAAACGATTGGTGCACAAACTACCAACCTAACGCTCCTTCTGTTTCTGTTACATACGATAACGCTGGCGTTCTTGGCATCACAGTTAAATCTAAC
AAATCTCTTGTTGGCGAAGGCTCTTCTGGCGTTATCAAAGGCAAAGGCCTTCGTATCGTTTCTGGCGCTTCTAACGTTATCATCCAAAACATCGCTA
TCACAGATCTTAACCCTAAATACGTTTGGGGCGGCGATGCTATCACACTTGATAACGCTGATATGGTTTGGATCGATCATGTTACAACAGCTCGTA
TCGGCCGTCAACATCTTGTTCTTGGCACATCTGCTTCTAACCGTGTTACAGTTTCTAACTCTTACTTCAACGGCGTTACATCTTACTCTGCTACATGC
GATGGCTACCATTACTGGGGCATCTACCTTACAGGCTCTAACGATATGGTTACACTTAAAGGCAACTACATCTACCATATGTCTGGCCGTTCTCCT
AAAGTTGGCGGCAACACACTTCTTCATGCTGTTAACAACTACTGGTACGATTCTTCTGGCCATGCTTTCGAAATCGATTCTGGCGGCTACGTTCTTG
CTGAAGGCAACGTTTTCCAAAACATCCCTACAGTTATCGAAGGCACAGTTGGCGGCCAACTTTTCACATCTCCTGATTCTTCTACAAACGCTATCT
GCTCTACATACCTTGGCCATACATGCCAAGTTAACGGCTTCGGCTCTTCTGGCACATTCAAACAAGCTGATACAGCTTTCCTTGTTAACTTCCAAG
GCAAAAACATCGCTTCTGCTTCTGCTTACACAGTTGCTCAATCTTCTGTTCCTTCTAACGCTGGCCAAGGCAAACTTTGA (SEQ ID NO: 14)

GalEZY galactosidase 2253 bp

ATGTTCCGTTCTACAGCTACAGTTGCTGCTGCTACAGCTATGGGCCTTCTTACAGCTACAGGCCATGGCTCTCTTGCTATCGCTCAAGGCACAACA
GGCTCTAACGCTGTTGTTGTTGATGGCACAAACTTCGCTCTTAACGGCGCTTCTATGTCTTACGTTTTCCATGCTAACTCTACAACAGGCGATCTTG
TTTCTGATCATTTCGGCGCTACAATCTCTGGCGCTATCCCTGCTCCTAAAGAACCTGCTGTTAACGGCTGGGTTGGCATGCCTGGCCGTATCCGT
CGTGAATTCCCTGATCAAGGCCGTGGCGATTTCCGTATCCCTGCTGTTCGTATCCGTCAAACAGCTGGCTACACAGTTTCTGATCTTCAATACCAA
GGCCATGAAGTTGTTGATGGCAAACCTGCTCTTCCTGGCCTTCCTGCTACATTCGGCGAAGCTGGCGATGTTACAACACTTGTTGTTCATCTTTAC
GATAACTACTCTGCTGTTGCTGCTGATCTTTCTTACTCTGTTTTCCCTGAATTCGATGCTGTTGTTCGTTCTGTTAACGTTACAAACAAAGGCAAAGG
CAACATCACAATCGAAAACCTTGCTTCTCTTTCTGTTGATTTCCCTCTTGAAGATCTTGATCTTGTTTCTCTTCGTGGCGATTGGGCTCGTGAAGCTA
ACCGTGAACGTCGTCGTGTTGAATACGGCATCCAAGGCTTCGGCTCTTCTACAGGCTACTCTTCATCTTCATAACCCTTTCTTCGCTCTTGTTCA
TCCTTCTACAACAGAATCTCAAGGCGAAGCTTGGGGCTTCAACCTTGTTTACACAGGCTCTTTCTCTGCTCAAGTTGAAAAAGGCTCTCAAGGCCT
TACACGTGCTCTTATCGGCTTCAACCCTGATCAACTTTCTTGGAACCTTGGCCCTGGCGAAACACTTACATCTCCTGAATGCGTTTCTGTTTACTCT
AAAGATGGCATCGGCGGCATGTCTCGTAAATTCCATCGTCTTTACCGTAAACATCTTATCCGTTCTAAATTCGCTACATCTGATCGTCCTCCTCTTCT
TAACTCTTGGGAAGGCGTTTACTTCGATTTCAACCAATCTTCTATCGAAACACTTGCTGAACAATCTGCTGCTCTTGGCATCCGTCTTTTCGTTATGG
ATGATGGCTGGTTCGGCGATAAATACCCTCGTACATCTGATAACGCTGGCCTTGGCGATTGGACACCTAACCCTGATCGTTTCCCTAACGGCCTT
GAACCTGTTGTTGAAGAAATCACAAACCTTACAGTTAACGATACATCTGCTGAAAAACTTCGTTTCGGCATCTGGGTTGAACCTGAAATGGTTAACC
CTAACTCTTCTCTTTACCGTGAACATCCTGATTGGGCTCTTCATGCTGGCGCTTACGCTCGTACAGAACGTCGTAACCAACTTGTTCTTAACCTTGC
TCTTCCTGAAGTTCAAGAATACATCATCGATTTCATGACAGATCTTCTTAACTCTGCTGATATCTCTTACATCAAATGGGATAACAACCGTGGCATCC
ATGAAGCTCCTTCTCCTTCTACAGATCATGAATACATGCTTGGCGTTTACCGTGTTTTCGATACACTTACAGCTCGTTTCCCTGATGTTCTTTGGGAA
GGCTGCGCTTCTGGCGGCGGCCGTTTCGATGCTGGCGTTCTTCATTACTTCCCTCAAATCTGGACATCTGATAACACAGATGGCGTTGATCGTGT
TACAATCCAATTCGGCACATCTCTTGCTTACCCTCCTTCTGCTATGGGCGCTCATCTTTCTGCTGTTCCTAACCATCAAACAGGCCGTACAGTTCCT
CTTGAATTCCGTGCTCATGTTGCTATGATGGGCGGCTCTTTCGGCCTTGAACTTGATCCTGCTACACTTCAAGATGATCCTGATGTTCCTGAACTTA
TCCAAATGGCTGAAAAAGTTAACCCTCTTGTTCTTAACGGCGATCTTTACCGTCTTCGTCTTCCTGAAGAATCTCAATGGCCTGCTGCTCTTTTCGTT
GCTGAAGATGGCTCTCAAGCTGTTCTTTTCTACTTCCAACTTTCTCCTAACGTTAACCATGCTGCTCCTTGGGTTCGTCTTCAAGGCCTTGATCCTG
AAGCTTCTTACACAGTTGATGGCGATAAAACATACACAGGCGCTACACTTATGAACCTTGGCCTTCAATACACATTCGATACAGAAACGGCTCTAA
AGTTGTTTTCCTTGAACGTCAATGA (SEQ ID NO: 15)

EpgEZY polygalacturnoase 1143 bp

ATGTTCTACGCTCTTGGCCCTCTTGCTCTTTTCGCTTTCGCTACAGAAGTTATGGCTACACCTGTTGCTTACCCTATGACAACAGCTTC
TCCTACACTTGCTAAACGTGATTCTTGCACATTCTCTGGCTCTGATGGCGCTGCTTCTGCTTCTCGTTCTCAAACAGATTGCGCTACAA
TCACACTTTCTGATATCACAGTTCCTTCTGGCACAACACTTGATCTTTCTGATCTTGAAGATGATACAACAGTTATCTTCGAAGGCACAA
CATCTTGGGAATACGAAGAATGGGATGGCCCTCTTCTTCAAATCAAAGGCAACGGCATCACAATCAAAGGCGCTGATGGCGCTAAA
CTTAACCCTGATGGCTCTCGTTGGTGGGATGGCGAAGGCTCTAACGGCGGCGTTACAAAACCTAAATTCTTCTACGCTCATGATCTTA
CAGATTCTACAATCCAAAACCTTTACATCGAAAACACACCTGTTCAAGCTGTTTCTATCAACGGCTGCGATGGCCTTACAATCACAGAT
ATGACAATCGATAACTCTGCTGGCGATGATGCTGGCGGCCATAACACAGATGGCTTCGATATCGGCGAATCTTCTAACGTTGTTATCA
CAGGCGCTAAAGTTTACAACCAAGATGATTGCGTTGCTGTTAACTCTGGCACATCTATCACATTCTCTGGCGGCACATGCTCTGGCG
GCCATGGCCTTTCTATCGGCTCTGTTGGCGGCCGTGATGATAACACAGTTGATACAGTTACATTCAAAGATTCTACAGTTTCTAACTCT
GTTAACGGCATCCGTATCAAAGCTAAATCTGGCGAAACAGGCGAAATCAAAGGCGTTACATACTCTGGCATCTCTCTTGAATCTATCT
CTGATTACGGCATCCTTATCGAACAAAACTACGATGGCGGCGATCTTGATGGCGAAGTTACATCTGGCATCCCTATCACAGATCTTAC
AATCGAAAACATCTCTGGCTCTGGCGCTGTTGATTCTGATGGCTACAACATCGTTATCGTTTGCGGCGATGATGCTTGCTCTAACTGG
ACATGGTCTGATGTTGAAGTTACAGGCGGCGAAGATTACGGCTCTTGCGAAAACGTTCCTTCTGTTGCTTCTTGCTCTACATGA (SEQ ID NO: 16)

Pmo1EZY monooxygenase 1 1305 bp

ATGTCTGTTGCTCGTACAGCTGGCTTCGCTCTTGCTTCTGCTGCTATCGTTGCTGGCCATGGCTACGTTACAGGCATCGTTGCTGATG
GCACATACTACGGCGGCTACCTTGTTAACCAATACCCTTACTCTAACGATCCTCCTGCTGTTGTTGGCTGGGCTGAAGATGCTACAGA
TCTTGGCTTCGTTGATGGCTCTGGCTACACATCTGGCGATATCATCTGCCATAAAGATGCTACAAACGCTCAAGCTTCTGCTACAGTT
GCTGCTGGCGGCACAGTTGAACTTCAATGGACAGAATGGCCTGAATCTCATCATGGCCCTGTTATCGATTACATCGCTTCTTGCAAC
GGCGATTGCACAACAGTTGATAAAACAACACTTGAATGGGTTAAAATCTCTGAATCTGGCCTTGTTGATGGCTCTTCTGCTCCTGGCA
CATGGGCTTCTGATAACCTTATCTCTAACAACAACTCTTGGACAGTTACAATCCCTTCTTCTCTTGCTGCTGGCGGCTACGTTCTTCGT
CATGAAATCATCGCTCTTCATTCTGCTGGCAACGAAAACGGCGCTCAAAACTACCCTCAATGCGTTAACCTTGAAGTTACAGGCGGC
GGCTCTGCTTCTCCTTCTGGCACAGTTGGCACAGAACTTTACACACCTACAGATCCTGGCATCCTTGTTAACATCTACACATCTCTTGA
TTCTTACACAATCCCTGGCCCTGCTCTTTGGGATGGCGCTTCTTCTTCTGGCGGCAACTCTGGCTCTGGCTCTGCTTCTTCTTCTGCTG
CTGCTACATCTACACCTACAACACCTTCTGTTTCTGTTCCTGTTATCCCTACAGCTTCTTCTGGCGCTTCTTCTACACCTCTTGTTCCTA
CACCTTCTGCTCCTGCTGTTACACCTTCTGTTCCTGCTGGCAACCAAGCTCCTCAACCTACATACACATCTACATACATCGAAACAGA
AACACTTCCTGGCCAAACAGTTACATCTACAACAACAGAATACGCTTCTGAACCTACACAACCTGCTGTTGAAACACAAGTTGCTCAA
CCTTCTGAAACAGAAGCTGCTACATCTACATCTACAGTTACAGAAACAGCTTCTGCTACAGCTGCTCCTACAGGCTCTTCTGGCTCTT
CTTCTGGCTCTGGCTCTTCTTCTACAGAACTTCCTACAGATTCTTCTCTCTTTCTGATTACTTCTCTTCTCTTTCTGCTGAAGAATTCCTT
AACCTTCTTAAAGAAACACTTAAATGGCTTGTTACAGATAAAGTTCATGCTCGTTCTCTTCATTGA (SEQ ID NO: 17)

Pmo2EZY monooxygenase 2 864 bp

ATGAAACTTTCTCTTCTTGCTGCTGCTGCTATCGCTCCTATGGTTTCTGCTCATTACTTCTTCGATACACTTGTTATCGATGGCCAAGAA
ACAACACCTAACCAATACGTTCGTTCTAACACACGTCCTGAAAAATACAACCCTACAAAATGGGTTAACACACGTGATGATATGACAC
CTGATATGCCTGATTTCCGTTGCAACAAAGGCTCTTTCACATTCGCTGGCCAAACAGATACAGCTGAAGTTAAAGCTGGCTCTAAACT
TGCTATGAAACTTGGCGTTGGCGCTACAATGCAACATCCTGGCCCTGGCCTTGTTTACATGTCTAAAGCTCCTGGCGCTGCTAACCA
ATACGAAGGCGATGGCGATTGGTTCAAAATCCATGAAGAAGGCATCTGCGATACATCTAAAGATATCAAAACAGATGCTTGGTGCAC
ATGGGATAAAGATCGTATCGAATTCACAATCCCTGCTGATCTTCCTGATGGCGAATACCTTATCCGTTCTGAACATATCGGCGTTCAT
GGCGCTCATGATGGCCAAGCTGAATTCTACTACGAATGCGCTCAAGTTAAAGTTACAGGCGGCGGCAACGGCAACCCTCAAGATAC
AATCAAATTCCCTGGCGGCTACCAAAAAGATGATCCTTCTTTCAACTTCTCTGTTTGGGGCGGCATGAAAGATTACCCTATGCCTGGC
CCTGCTGTTTACACAGGCGGCTCTGGCTCTTCTACAGGCTCTTACAACGAATCTAACGCTGAAGATTCTAACGAATACCCTTACCAAA
AAGAATCTGGCACATGCCAATCTAACTTCTACCGTCGTGAACATGCTCGTGATTTCTCTCATCGTCGTGCTTGA (SEQ ID NO: 18)

Pmo3EZY monooxygenase 3 696 bp

ATGAAATCTGGCCTTCTTTTCACAACAGCTTCTCTTGCTCTTACAGCTTCTGCTCATTACGTTTTCCCTGCTCTTGTTCAAGATGGCGCT
GCTACAGGCGATTGGAAATACGTTCGTGATTGGACAGGCTCTTACGGCAACGGCCCTGTTGAAGATGTTACATCTCTTGATATCCGTT
GCAACAAAGATGCTTCTACAAACGGCAACGCTACAGAAACACTTCCTGTTAAAGCTGGCGAAGAAATCGGCTTCACAGTTCGTACAA
ACATCGGCCATCCTGGCCCTCTTCTTGCTTACATGGCTAAAGCTCCTGGCGATGCTTCTGATTTCGATGGCGATGGCCAAGTTTGGTT
CAAAATCTACGAAGATGGCCCTACAGTTACAGATGATGGCCTTACATGGCCTTCTGATGGCGCTACAAACGTTAACTTCACAATCCCT
TCTTCTCTTCCTGATGGCGATTACCTTCTTCGTGTTGAACATATCGCTCTTCATGGCGCTGGCACAGAAGGCGGCGCTCAATTCTACC
TTTCTTGCGGCCAAGTTCTGTTACAGGCGGCGGCAACGGCGATCCTGCTCCTCTTGTTGCTTTCCCTGGCGCTTACGATCCTACAG
ATCCTGGCATCCTTATCAACATCTACTGGCCTGTTCCTACAAACTACACACCTCCTGGCCCTAAAGTTTGGTCTGGCTGA (SEQ ID
NO: 19)

Figure 7K

Pmo4EZY monooxygenase 4 1209 bp

ATGTCTCGTCTTGTTTCTTTCGCTTCTCTTCTTGCTGCTGTTAACGCTCATGGCTACGTTCAAAACATCGTTGTTAACGGCGTTTACTAC

TCTGGCTGGGAAATCAACACATACCCTTACATGACAGATCCTCCTGTTGTTGCTGCTTGGCAAATCCCTAACTCTAACGGCCCTGTTG

ATGTTTCTAACGGCTACACAACAGAAGATATCATCTGCAACCTTAACGCTACAAACGCTGCTGGCTACGTTGAAGTTGCTGCTGGCG

ATAAAATCAACCTTCAATGGTCTGCTTGGCCTGATACACATCATGGCCCTGTTATCTCTTACCTTGCTGATTGCGGCGATGATTGCACA

ACAGTTGATAAAACAACACTTGAATTCTTCAAAATCGATGCTGTTGGCCTTGTTGATGATTCTACAGTTCCTGGCACATGGGGCGATG

ATGAACTTATCGAAAACAACAACTCTTGGATGGTTGAAATCCCTACATCTATCGCTCCTGGCAACTACGTTCTTCGTCATGAAATCATC

GCTCTTCATTCTGCTGGCACAGAAGGCGGCGCTCAAAACTACCCTCAATGCTTCAACCTTAAAGTTACAGGCTCTGGCACAGATTCT

CCTGCTGGCACACTTGGCACAGAACTTTACAACCTTGATGATCCTGGCATCCTTGTTAACATCTACGCTTCTCTTTCTACATACGTTAT

CCCTGGCCCTACACTTTACTCTGGCGCTACATCTATCGCTCAAGCTACATCTGCTATCACAGCTACAGGCTCTGCTACATCTGGCGCT

GGCGGCGCTGCTGCTACAGGCTCTTCTGCTGCTACAACAACAGCTGCTGCTGCTTCTACAACAGCTACACCTACAACAGCTGCTGC

TCAAACAGCTAAATCTGCTTCTGCTCCTTCTTCTGCTGCTACAGGCTCTGTTCCTGCTGCTCCTACAACAGCTACAGTTTCTACAACAA

CATCTATCGCTACATCTGTTGGCACAACACTTACACGTACAACACTTGCTACAACAACAACAGCTGCTGCTGCTGAACCTTCTGCTTC

TGCTCCTGCTCCTTCTGGCAACTCTGCTTCTGGCTCTAACCCTCTTTACGCTCAATGCGGCGGCCTTAACTTCAAAGGCGCTTCTGGC

TGCGTTGCTGGCGCTACATGCAAAAAAATGAACCCTTACTACTCTCAATGCGTTTCTGCTTGA (SEQ ID NO: 20)

Figure 7L

FaeEZY feruloyl esterase 249 aa GI:67538194
ANSPGCGKQPTLTNGVNQINGREYVLKIPDGYDPSKPHHLIFGLHWRGGNMYNVVNGDSIQPWYGLEARAQGSAIFV
APNGLNAGWANTNGEDVAFIDAIMEQVEDDLCVDQASRFATGFSWGGGMSYALACARAAEFRAVSVLSGGLISGCD
GGNDPIAYLGIHGINDPVLPLDGGVTLANTFVSNNGCQPTDIGQPASGSGGSVRTDFSGCSHPVSFIAYDGGHDGAPL
GVGSSLAPDATWEFFMAA (SEQ ID NO: 21)

CelEZY cellulase 413 aa GI:67525921
QQIGTPEIRPRLTTYHCTSANGCTEQNTSVVLDAATHPIHDASNPSVSCTTSNGLNPALCPDKQTCADNCVIDGITDYAA
HGVETHGSRLTLTQYRNVNGALSSVSPRVYLVDESDPDEQEYRALSLLAQEFTFTVNVSALPCGMNGALYLSEMSPSGG
RSALNPAGASYGTGYCDAQCYVNPWINGEGNINGYGACCNEMDIWEANSRTGFTPHACLYEPEETEGRGVYECASE
DECDSAGENDGICDKWGCGFNPYALGNTEYYGRGQGFEVDTKEPFTVVTQFLTDDGTSTGALTEIRRLYIQNGQVIEA
VVSSGADSLTDSLCASTASWFDSYGGMEGMGRALGRGMVLAMSIWNDAGGYMQWLDGGDAGPCNATEGAPEFIE
EHTPWTRVVFEDLKWGDIGSTFQA (SEQ ID NO: 22)

CdhEZY cellobiose dehydrogenase 779 aa GI:67900486
HSFLRSFAALVAAGSDPDTGIVFDTWTVEASSSSAGFTFGVSLPEDALDTDATEFIGYLSCSSSSTSEFTGWCGLSMGSS
MNSNLLLVAYAQDDTVLTSFRFSSGYAMPSVYSGNATLTQISSTVTADKFEVLFRCEECLRWDHEGVSGSATTSAGQLIL
AWAQAEESPTNADCPDDLSLVQHEAQGIWVGKLSGDAATSNYETWAALATNVVDGTCGTDGGGGGDNGNGTTPG
VPVPTNVTYDYIIVGSGPAGMVLADRLSEAGAKTLLIEKGPPSIGLWNGTMKPDWLNGTDLTRFDVPGLCNEIWKNSD
GIACPDNDQMAGCLVGGGTAVNSGLWWKPYSKDFDESFPETWKYDDVRDAVTRVFTRIPGTTTPSTDNRLYLAEGPS
VIMNGLLASGWKGTTFNDEPEEKYKSVGYSPYMFSHGQRNGPMATYLLDAYQRPNFDLWVNTVVRRVVRDGATVT
GVEVEPFNDGGYEGSLQLNEGGRVILSAGAFGTPKILFRSGIGPEDQLAIVNGSASDGETMISEDQWINLPVGENLMDH
PNTEIVVQHPDVVFYDYYAAYDDPIEADAQSYLVNRTGPLAQSAPNVNPVFFDQVTGSDNVTRQLQYQARVEGSHNV
ADGHTISISQYVGRGQTSRGKLTITSALNTVVSTLPWLQDDNDTDAVIAGLERLRDSLSTIQGLTWAYPKANVSMAEHV
NSMAKTGRGSNHWMGSCKMGPDDGRDGGSSVVDLNTKVYGMDNLFVVDASIFPGMISTNPSAYITVVAERAAERIL
ALQG (SEQ ID NO: 23)

CbcEZY cellulose 1,4-beta-cellobiosidase 507 aa GI:67516425
QKVGTQQAEVHPGLTWQTCTSSGSCTTVNGEVTIDANWRWLHTVNGYTNCYTGNEWDTSICTSNEVCAEQCAVDG
ANYASTYGITTSGSSLRLNFVTQSQQKNIGSRVYLMDDEDTYTMFYLLNKEFTFDVDVSELPCGLNGAVYFVSMDADG
GKSRYATNEAGAKYGTGYCDSQCPRDLKFINGVANVEGWESSDTNPNGGVGNHGSCCAEMDIWEANSISTAFTPHP
CDTPGQTLCTGDSCGGTYSNDRYGGTCDPDGCDFNSYRQGNKTFYGPGLTVDTNSPVTVVTQFLTDDNTDTGTLSEIK
RFYVQNGVVIPNSESTYPANPGNSITTEFCESQKELFGDVDVFSAHGGMAGMGAALEQGMVLVLSLWDDNYSNML
WLDSNYPTDADPTQPGIARGTCPTDSGVPSEVEAQYPNAYVVYSNIKFGPIGSTFGNGGGSGPTTTVTTSTATSTTSSA
TSTATGQAQHWEQCGGNGWTGPTVCASPWACTVVNSWYSQCLLEDG (SEQ ID NO: 24)

Figure 8A

XylEZY xylanase 290 aa GI:259487165
AVLPRQSASLNDLFVAAGKSYFGTCSDQALLQNSQNEAIVASQFGVITPENSMKWDALEPSQGNFGWSGADYLVDYA
TQHNKKVRGHTLVWHSQLPSWVSSIGDANTLRSVMTNHINEVVGRYKGKIMHWDVVNEIFNEDGTFRNSVFYNLLG
EDFVRIAFETARAADPDAKLYINDYNLDSASYAKTQAMASYVKKWLAEGVPIDGIALSSLANTGVSEVAITELDIAGAASS
DYLNLLNACLNEQKCVGITVWGVSDKDSWRASDSPLLFDGNYQPKDAYNAIVNALS (SEQ ID NO: 25)

RhlEZY rhammnoglacturonan lyase 1020 aa GI:67527724
ALTTTSNSTHYTISNSRFSVAVAKSNGHVVDANLDGQDLLGPLSGNSGKGPYLDCSCTPEGFWTPGAEPALVNGTDST
GTPYVGVIMTDTYETTNQTLSQYLFLRGEETGLHAFSRVTYYNESDYFLRGLGELRTLFRPNTNLWTHFSGSEGNYGPM
PLSSTEKITVQDATTYLGDTTDDPYVSQYSDYFTKYTLTESWRDHDVHGHFSNGSTSGDGNTYGAWLVHNTRETYYGG
PLHADLVVDGIVYNYIVSGHYGAPNPNLTHGFDRTFGPQYYHFNSGGPGTTLEELRADAAQYASPEWNAEFYDSIAKHI
PNYVPSTGRTTFRGKVNLPKGAKKPIIVLSENEQDFQLNVFKKDSLQYWAEIDGSGAFTIPRVVKGTYRVTIYADEIFGW
FIKDNVKVIGSNAHTFTWKEETAGKEIWRIGVPDKSSGEFLHGYAPDTSKPLQPEQYRIYWGKYDYPSDFPEGVNYHVG
KSDPAKDLNYIHWSFFPSQGNHLRNEPYYQNVNNWTITFDLTASQLRNTKTATFTVQLAGTRNANGNSKWNPDPAK
YNNLPWTVNVNGIYEDTWEIPYWRSGSCGVRSGVQCQNTEHKFVFDAGKLRKGRNEFVLSLPFNATSVETALLPNSLY
VQVVSMEAVSVSNDMRVLVQAFMPLVTWGTAVEKRVLLTGIVSVSAMAKEDYPMISRPCPRKGGTRRRKKERKKEG
KKQGRTVLDALLQRSEQDSFWSRFCRSPIESVAQYVYGQGSTALRKKTTDNLVRVVCVSDTHNTKPNLPDGDILIHAGD
LTESGTKEELEKQIYWLDSQPHRYKIVIAGNHETFLDRNYHSHHGNERVTMDWKSLIYLENTSAILDLGAGHQLKVFGSP
YTPKHGNGAFQYPRTDTTTWEEIPKDTDLLVTHGPPKAHLDLGHLGCRVLRQALWEMESRPLLHVFGHIHGGYGKEV
VCWDLCQRAYEAIMDGESRWWNLCVLFYCWILRLFFDWTADGRATVLVNAATVGGVRDLKRREAICVDIQAGSKRFL
SGCT (SEQ ID NO: 26)

RhaEZY rhammnoglacturonan acetylesterase 228 aa GI:67524141
QTIYLAGDSTMASSTPGWGDYIADSVSVEISNQAIGGRSARSYTREGRFQAIADVLQAGDYVVIEFGHNDGGSLSNDN
GRTDCPGDGDETCETVYNGVAETVLTFPAYIENAALLFLEKGANVLISSQTPNNPWESGTFSYTPNRFVGYAELAAQRA
GVDYVDHGAYTASIFEALGADTVNSFYPNDHTHTNAEGSSVVADAFLKAVVCSGVALNDVLTRTDFDGECL
(SEQ ID NO: 27)

EglEZY endoglucanase 307 aa GI:67521656
AFTWLGTNEAGAEFGEGSYPGELGTEYIWPDLGTIGTLRNEGMNIFRVAFSMERLVPDSLAGPVADEYFQDLVETVNG
ITALGAYAVLDPHNYGRYYGNIITSTDDFAAFWTILATEFASNELVIFDTNNEYHTMDQSLVLNLNQAAIDAIRASGATS
QYIFAEGNSWTGAWTWVDVNDNMKALTDPQDKLIYEMHQYLDSDGSGTNTACVSSTIGSERVTAATNWLRENGKL
GVLGEFAGANNQVCKDAVADLLEYLEENSDVWLGALWWAAGPWWGDYMFNMEPTSGIAYQEYSEILQPYFVGSQ
(SEQ ID NO: 28)

ManEZY mannanase 365 aa GI:67525801
LPHASTPVYTPSTTPSPTPTPSASGSFATTSGIQFVIDGEAGYFPGSNAYWIGFLKNNSDVDLVFDHMASSGLRILRVWG
FNDVNTAPTDGSVYFQLHQDGKSTINTGKDGLQRLDYVVHSAEKHGIKLIINFVNYWDDYGGMNAYMRAYGGGDKA
DWFENEGIQAAYQAYVEAVVKRYINSTAVFAWELANEPRCTGCEPSVLHNWIEKTSAFIKGLDEKHLVCIGDGSDGSYP
FQYTEGSDFAAALTIDTIDFGTFHLYPDSWGTNNDWGKLWITSHAAACAAAGKPCLFEEYGVTSNHCAIEKQWQNAA
LNATGIAADLYWQYGDTLSSGPSPDDGNTFYYGSEEFECLVTNHVETIERSAK (SEQ ID NO: 29)

Figure 8B

CbhEZY cellobiohydrolase 431 aa GI:67538224
QQTLYGQCGGSGWTGATSCVAGAACSTLNQWYAQCLPAATTTSTTLTTTTSSVTTTSNPGSTTTTSSVTVTATASGNP
FSGYQLYVNPYYSSEVQSIAIPSLTGTLSSLAPAATAAAKTRDVAAKVPTMATYLADIRSQNAAGANPPIAGQFVVYDLP
DRDCAALASNGEFAISDGGVQHYKDYIDSIREILVEYSDVHVILVIEPDSLANLVTNLNVAKCANAQSAYLECTNYAVTQL
NLPNVAMYLDAGHAGWLGWPANLQPAANLYAGVYSDAGSPAALRGLATNVANYNAWAIDTCPSYTQGNSVCDEK
DYINALAPLLRAQGFDAHFITDTGRNGKQPTGQQAWGDWCNVIGTGFGARPSTNTGDSLLDAFVWVKPGGESDGTS
DTSAARYDAHCGYSDALQPAPEAGTWFQAYFVQLLQNANPSF (SEQ ID NO: 30)

CutEZY cutinase 240 aa GI:67901108
SPLNLDERQHAVGSSSGNDLRDGDCKPVTFIFARASTEPGLLGMSTGPAVCNDLKADASLGGVACQGVGPKYTAGLAE
NALPQGTSSAAINEAKELFELAASKCPDTRIVAGGYSQGTAVMHGAIPDLSDEIKDKIAGVVLFGDTRNKQDGGQIKNF
PKDKIKIYCATGDLVCDGTLVVTAAHFTYVANTGEASKWLEQQLASMPASTSTSSSSSSSSSAPASQTSQSSGLSSWFSG
LGN (SEQ ID NO: 31)

RhgEZY rhamnogalacturonase 500 aa GI:67901108
QLSGSVGPLTSVSSKSQTKTCNVLDYGAVADKSTDIGPALSSAWDECADGGVVYIPPGDYAIETWVKLSGGKACAIQLD
GIIYRTGTDGGNMIMIEHTSDFEFFSSTSKGAFQGYGYEFHAKGSSDGPRILRLYDVSDFSVHDVALVDSPLFHFSMDTC
SNGEVYNMAIRGGNMGGLDGIDVWSTNVWIHDVIHAEHSPFDARSDRLQSPSKNILVENIYCNWSGGCAMGSLGTD
TDISDIVYRNVYTWKSNQMYMVKSNGGSGTVSNLVLENFIARADSKGHGNAYSLDIDSAWSSMSTIEGDGVELKNVTI
RNWKGTEADGSQRGPIKVKCASGAPCTDVTVEDFAMWTESGDEQTYVCENAFGDGFCLADGDGTSTFTTTLTASAA
PSGYSAPSMDADLETAFGTDSEIPIPTIPTSFYPGATPYSALAGASVSSSQVPAASSSAEAKFVASPATSSPTATSTAISSVD
PVSAATTTATSHGHGKSHHKHQCRAHRH (SEQ ID NO: 32)

GluEZY glucosidase 599 aa GI:67522695
LAIKSNEPELLRRDALPIYKNASYCVDERVRDLLSRMTLEEKAGQLFHKQLSEGPLDDDSSGNSTETMIGKKHMTHFNLA
SDITNATQTAEFINLIQKRALQTRLGIPITISTDPRHSFTENVGTGFQAGVFSQWPESLGLAALRDPQLVREFAEVAREEYL
AVGIRAALHPQVDLSTEPRWARISGTWGENSTLTSELIVEYIKGFQGEGKLGPKSVKTVTKHFPGGGPMENGEDSHFYY
GKNQTYPGNNIDEHLIPFKAALAAGATEIMPYYSRPIGTNWEAVGFSFNKEIVTDLLRGELGFDGIVLTDWGLITDTYIG
NQYMPARAWGVEYLSELQRAARILDAGCDQFGGEERPELIVQLVREGTISEDRIDVSVARLLKEKFLLGLFDNPFVNASA
ANNIVGNEHFVNLGRDAQRRSYTLLTNNQTILPLAKPGEGTRFYIEGFDSAFMSARNYTVVNTTEEADFALLRYNAPYEP
RNGTFEANFHAGSLAFNATEKARQAKIYSSLPTIVDIILDRPAVIPEVVEQAQAVLASYGSDSEAFLDVVFGVSKPEGKLPF
DLPRSMDAVEAQAEDLPFDTENPVFRYGHGLEYEDN (SEQ ID NO: 33)

PelEZY pectin lyase 360 aa GI:67524223
AGVTGSAEGFAKGVTGGGSATPVYPSTTAELVSYLGDSSARVIVLTKTFDFTGTEGTTTETGCAPWGTASACQVAINKN
DWCTNYQPNAPSVSVTYDNAGVLGITVKSNKSLVGEGSSGVIKGKGLRIVSGASNVIIQNIAITDLNPKYVWGGDAITLD
NADMVWIDHVTTARIGRQHLVLGTSASNRVTVSNSYFNGVTSYSATCDGYHYWGIYLTGSNDMVTLKGNYIYHMSGR
SPKVGGNTLLHAVNNYWYDSSGHAFEIDSGGYVLAEGNVFQNIPTVIEGTVGGQLFTSPDSSTNAICSTYLGHTCQVNG
FGSSGTFKQADTAFLVNFQGKNIASASAYTVAQSSVPSNAGQGKL (SEQ ID NO: 34)

Figure 8C

GalEZY galactosidase 729 aa GI:74593086
HGSLAIAQGTTGSNAVVVDGTNFALNGASMSYVFHANSTTGDLVSDHFGATISGAIPAPKEPAVNGWVGMPGRIRRE
FPDQGRGDFRIPAVRIRQTAGYTVSDLQYQGHEVVDGKPALPGLPATFGEAGDVTTLVVHLYDNYSAVAADLSYSVFPE
FDAVVRSVNVTNKGKGNITIENLASLSVDFPLEDLDLVSLRGDWAREANRERRRVEYGIQGFGSSTGYSSHLHNPFFALV
HPSTTESQGEAWGFNLVYTGSFSAQVEKGSQGLTRALIGFNPDQLSWNLGPGETLTSPECVSVYSKDGIGGMSRKFHR
LYRKHLIRSKFATSDRPPLLNSWEGVYFDFNQSSIETLAEQSAALGIRLFVMDDGWFGDKYPRTSDNAGLGDWTPNPD
RFPNGLEPVVEEITNLTVNDTSAEKLRFGIWVEPEMVNPNSSLYREHPDWALHAGAYARTERRNQLVLNLALPEVQEYI
IDFMTDLLNSADISYIKWDNNRGIHEAPSPSTDHEYMLGVYRVFDTLTARFPDVLWEGCASGGGRFDAGVLHYFPQIW
TSDNTDGVDRVTIQFGTSLAYPPSAMGAHLSAVPNHQTGRTVPLEFRAHVAMMGGSFGLELDPATLQDDPDVPELIQ
MAEKVNPLVLNGDLYRLRLPEESQWPAALFVAEDGSQAVLFYFQLSPNVNHAAPWVRLQGLDPEASYTVDGDKTYTG
ATLMNLGLQYTFDTEYGSKVVFLERQ (SEQ ID NO: 35)

EpgEZY polygalacturnoase 361 aa GI:67902680
TPVAYPMTTASPTLAKRDSCTFSGSDGAASASRSQTDCATITLSDITVPSGTTLDLSDLEDDTTVIFEGTTSWEYEEWDG
PLLQIKGNGITIKGADGAKLNPDGSRWWDGEGSNGGVTKPKFFYAHDLTDSTIQNLYIENTPVQAVSINGCDGLTITD
MTIDNSAGDDAGGHNTDGFDIGESSNVVITGAKVYNQDDCVAVNSGTSITFSGGTCSGGHGLSIGSVGGRDDNTVDT
VTFKDSTVSNSVNGIRIKAKSGETGEIKGVTYSGISLESISDYGILIEQNYDGGDLDGEVTSGIPITDLTIENISGSGAVDSDG
YNIVIVCGDDACSNWTWSDVEVTGGEDYGSCENVPSVASCST (SEQ ID NO: 36)

Pmo1EZY monooxygenase 1 415 aa GI:67517718
HGYVTGIVADGTYYGGYLVNQYPYSNDPPAVVGWAEDATDLGFVDGSGYTSGDIICHKDATNAQASATVAAGGTVEL
QWTEWPESHHGPVIDYIASCNGDCTTVDKTTLEWVKISESGLVDGSSAPGTWASDNLISNNNSWTVTIPSSLAAGGYV
LRHEIIALHSAGNENGAQNYPQCVNLEVTGGGSASPSGTVGTELYTPTDPGILVNIYTSLDSYTIPGPALWDGASSSGGN
SGSGSASSSAAATSTPTTPSVSVPVIPTASSGASSTPLVPTPSAPAVTPSVPAGNQAPQPTYTSTYIETETLPGQTVTSTTT
EYASEPTQPAVETQVAQPSETEAATSTSTVTETASATAAPTGSSGSSSGSGSSSTELPTDSSSLSDYFSSLSAEEFLNLLKET
LKWLVTDKVHARSLH (SEQ ID NO: 37)

Pmo2EZY monooxygenase 2 270 aa GI:67525177
HYFFDTLVIDGQETTPNQYVRSNTRPEKYNPTKWVNTRDDMTPDMPDFRCNKGSFTFAGQTDTAEVKAGSKLAMKL
GVGATMQHPGPGLVYMSKAPGAANQYEGDGDWFKIHEEGICDTSKDIKTDAWCTWDKDRIEFTIPADLPDGEYLIRS
EHIGVHGAHDGQAEFYYECAQVKVTGGGNGNPQDTIKFPGGYQKDDPSFNFSVWGGMKDYPMPGPAVYTGGSGSS
TGSYNESNAEDSNEYPYQKESGTCQSNFYRREHARDFSHRRA (SEQ ID NO: 38)

Pmo3EZY monooxygenase 3 213 aa GI:67540516
HYVFPALVQDGAATGDWKYVRDWTGSYGNGPVEDVTSLDIRCNKDASTNGNATETLPVKAGEEIGFTVRTNIGHPGP
LLAYMAKAPGDASDFDGDGQVWFKIYEDGPTVTDDGLTWPSDGATNVNFTIPSSLPDGDYLLRVEHIALHGAGTEGG
AQFYLSCGQVSVTGGGNGDPAPLVAFPGAYDPTDPGILINIYWPVPTNYTPPGPKVWSG (SEQ ID NO: 39)

Figure 8D

Pmo4EZY monooxygenase 4 386 aa GI:75859132
HGYVQNIVVNGVYYSGWEINTYPYMTDPPVVAAWQIPNSNGPVDVSNGYTTEDIICNLNATNAAGYVEVAAGDKINL
QWSAWPDTHHGPVISYLADCGDDCTTVDKTTLEFFKIDAVGLVDDSTVPGTWGDDELIENNNSWMVEIPTSIAPGNY
VLRHEIIALHSAGTEGGAQNYPQCFNLKVTGSGTDSPAGTLGTELYNLDDPGILVNIYASLSTYVIPGPTLYSGATSIAQAT
SAITATGSATSGAGGAAATGSSAATTTAAAASTTATPTTAAAQTAKSASAPSSAATGSVPAAPTTATVSTTTSIATSVGT
TLTRTTLATTTTAAAAEPSASAPAPSGNSASGSNPLYAQCGGLNFKGASGCVAGATCKKMNPYYSQCVSA (SEQ ID
NO: 40)

Figure 8E

SYSTEMS AND METHODS FOR PRODUCTION AND USE OF FUNGAL GLYCOSYL HYDROLASES

CROSS REFERENCE TO RELATED APPLICATIONS

This application claims the benefit of U.S. Provisional Patent Application Ser. No. 62/006,410 filed on Jun. 2, 2014, and incorporates said provisional application by reference into this document as if fully set out at this point.

STATEMENT REGARDING FEDERAL SPONSORED RESEARCH OR DEVELOPMENT

This invention was made with U.S. Government support under USDA/NIFA Grant No. 2007-35504-18244 awarded by the Department of Agriculture. The Government has certain rights in this invention.

SEQUENCE LISTING

This application includes as the Sequence Listing the complete contents of the accompanying text file "Sequence.txt", created Jun. 2, 2015, containing 115,881 bytes, hereby incorporated by reference.

TECHNICAL FIELD

This invention generally relates to the production and use of glycosyl hydrolases from fungi to digest biomass. In particular, enzymes from *Aspergillus nidulans* and *Phanerochaeie chrysosporium* have been isolated and characterized, and synergistic mixtures of the enzymes have been produced and used to generate simple sugars from biomass without the need to pretreat the biomass before digestion.

INTRODUCTION

Lignocellulose, a major structural component of woody and non-woody plants, is abundant in nature and has great potential for bioconversion to many useful products, including simple sugars, e.g. for the production of biofuel. The major challenge to accessing the lignocellulose components e.g. by enzymatic digestion, is the recalcitrance of lignocellulose due to the complexity of the network of lignin, hemicelluloses and cellulose and the crystallinity of cellulose (FIGS. 1A and B).

Through millions of years of evolution, plant saprophytic fungi have optimized their lignocellulose degrading ability. They produce arrays of enzymes capable of breaking down each component polymer and have regulatory systems to ensure the production of only those enzymes needed for efficient conversion of the available substrate to usable sugars. Fungi typically secrete two types of biomass-degrading extracellular enzymes (hydrolytic and ligninolytic) and thus are of special interest to the biofuels and biotechnology industry. Lignocellulose degrading fungi are now used on an industrial scale for production of enzymes such as xylanases and cellulases. The production costs of microbial enzymes are tightly connected with the productivity of the enzyme-producing strain and the final activity yield in a fermentation broth.

Current industrial methods that employ such enzymes to degrade lignocellulosic materials typically involve the use of pre-treated biomass to render the cellulose more accessible to the enzymes that are currently available. Pre-treatment entails, for example, steam explosion, hydrothermolysis and/or chemical treatments with various acids, alkali, organic solvents and $FeCl_3$. These processes and agents are expensive and have numerous limitations such as a lack of reaction specificity, the generation of enzyme inhibitors which slow or eliminate the desired reactions, and the use harsh chemicals, which makes these procedures expensive and environmentally unfriendly. It would be beneficial to have available enzymes, especially groups or arrays of enzymes, which function together in a coordinated manner to digest biomass without the need for pretreatment. The hydrolytic efficiency of a multi-enzyme complex depends on properties of the individual enzymes, the synergies among them, and their ratio in multi-enzyme blends. Therefore, the discovery and characterization of highly efficient enzymes, and enzymes whose activities complement one another, is necessary so as to successfully access and digest the cellulose in biomass.

Thus, there exists a clear emerging and ongoing need to identify, isolate and characterize biomass-degrading enzymes with improved efficacy and greater yield to further advance the commercialization of biomass bioconversion processes. In particular, it would be of benefit to have available enzymes and/or mixtures of enzymes (enzyme systems) which function in a complementary manner to release simple sugars from biomass without the need for pre-treatment of the biomass.

Accordingly, it should now be recognized, as was recognized by the present inventors, that there exists, and has existed for some time, a very real need for an invention that would address and solve the above-described problems.

Before proceeding to a description of the present invention, however, it should be noted and remembered that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

SUMMARY OF THE INVENTION

The present disclosure describes the discovery, molecular engineering, production and characterization of a comprehensive set of enzymes isolated from two different lead fungi, *Aspergillus nidulans* and *Phanerochaete chrysosporium*. *A. nidulans* is a producer of hemicellulases, cellulases, and pectinases whereas *P. chrysosporium* produces a suite of enzymes for degradation of hemicellulose, cellulose, and lignin. Enzymes of several different types (e.g. cellulases, hemicellulases, pectinases, carbohydrate esterases, chitinases, etc.) from these two fungi have been characterized and purposefully selected for maximal activity and efficiency. Significantly, mixtures ("cocktails") of the enzymes have been designed to efficiently and synergistically catalyze the complete degradation of lignin and cellulose in biomass into simple sugars in a cooperative, complementary manner, obviating the need for pretreatment of the biomass before degradation, and decreasing the production of enzyme inhibitors. In some aspects, the enzyme cocktails may be, for example, a fermentation broth of recombinant fungal cells which produce two or more or the enzymes described herein, and/or a cell free broth containing two or more purified recombinant enzymes. The GenBank deposit numbers of nucleic acids encoding enzymes suitable for use in the invention, as available Jun. 2, 2014, are presented in Tables 1-12. Exemplary nucleotide sequences of synthetic cloned nucleic acids corresponding to those sequences are set forth in SEQ ID NOS: 1-20, and the exemplary amino acid sequences of proteins encoded by SEQ ID NOS: 1-20 are set forth in SEQ ID NOS: 21-40.

In some aspects, the lignocellulose is broken down to products suitable for biofuel production, e.g. simple sugars such as glucose. However, the enzyme blends and the products obtained using the enzyme blends also have various other commercial applications outside of the biofuel industry e.g., in the food industry, for the treatment of agricultural waste, in the manufacture of animal feed, in pulp and paper production, for extraction of various plant products, and in cleaning agents, to name a few representative examples. Products comprising the enzymes described herein, or combinations thereof, and/or products comprising products made from the enzymes described herein are also encompassed by the invention.

The enzymes and enzyme blends can be used to hydrolyze hemicelluloses and cleave linkages between lignin and hemicelluloses in any type of biomass. In some aspects, the biomass is sorghum stover.

The foregoing has outlined in broad terms some of the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

BRIEF DESCRIPTION OF THE DRAWINGS

These and further aspects of the invention are described in detail in the following examples and accompanying drawings.

FIG. 1A contains a schematic depiction of a plant cell wall and FIG. 1B contains a summary of the different kinds of aromatic ester and ether cross links between carbohydrate and lignin.

FIG. 7A-L. Nucleotide sequences of SEQ ID NOS: 1-20.

FIG. 8A-E. Amino acid sequences of SEQ ID NOS: 21-40, showing the sequences and the GenInfo identifying deposit number.

DETAILED DESCRIPTION

Figure 2:
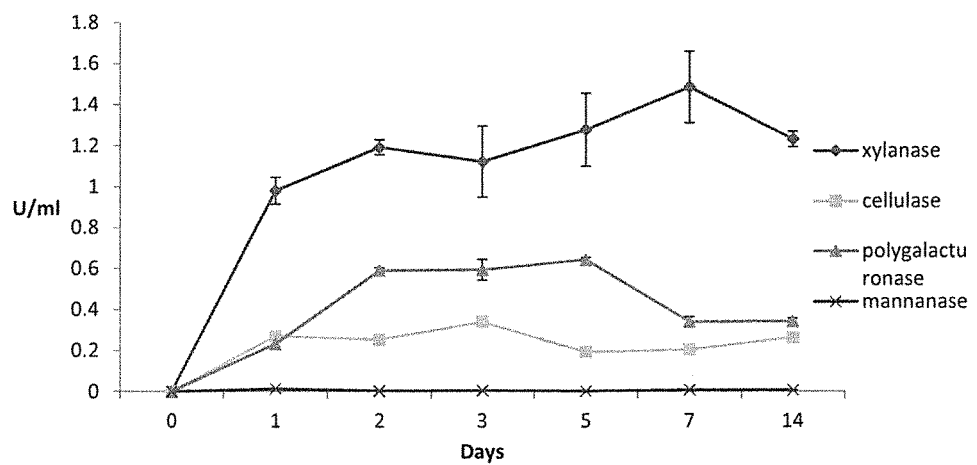
FIG. 2 contains a graph of the estimation of enzyme activities. The enzyme activities of xylanase, cellulase, polygalacturonase and mannanase in *A. nidulans* grown on sorghum for 1, 2, 3, 5, 7 and 14 days under solid state cultivation were assessed. Enzyme activities were measured by quantitating the released reducing sugars using the 3, 5-dinitrosalicylic acid (DNS) method, and are expressed as U/ml. One unit of enzyme activity is defined as the amount of enzyme releasing 1 µmol of product per minute. Data represent mean±SE and the error bars specify standard deviation.
Figure 3:
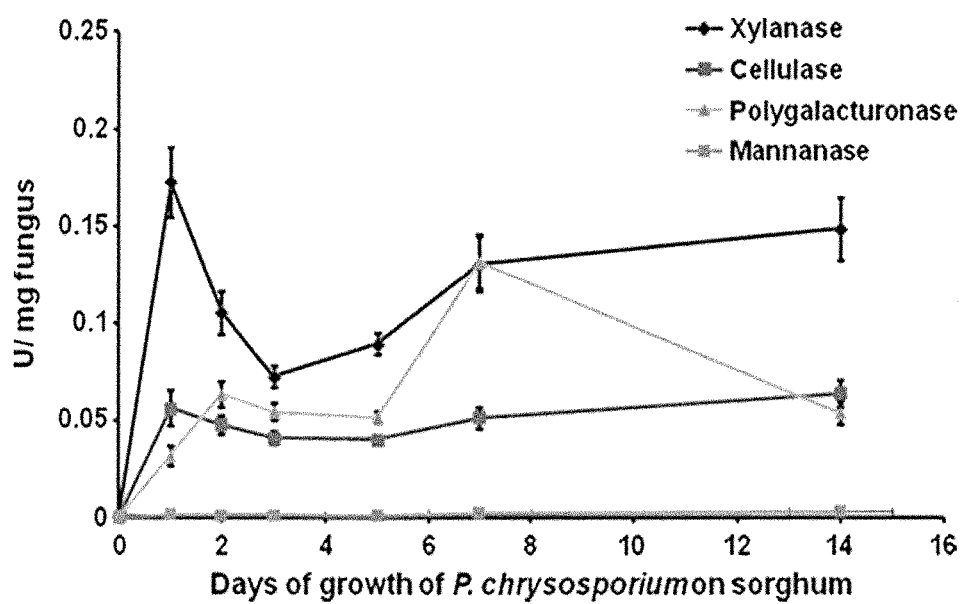
FIG. 3 contains a plot of xylanase, cellulase, polygalacturonase, and mannanase activities of *Phanerochaete chrysosporium* grown on sorghum for 1, 2, 3, 5, 7, and 14 days. On the y-axis, units of enzyme activity per milligram fungus are shown. One unit of enzyme activity was defined as the amount of enzyme liberating 1 µmol of product per minute. Data represent mean-SE (n=3)
Figure 4:
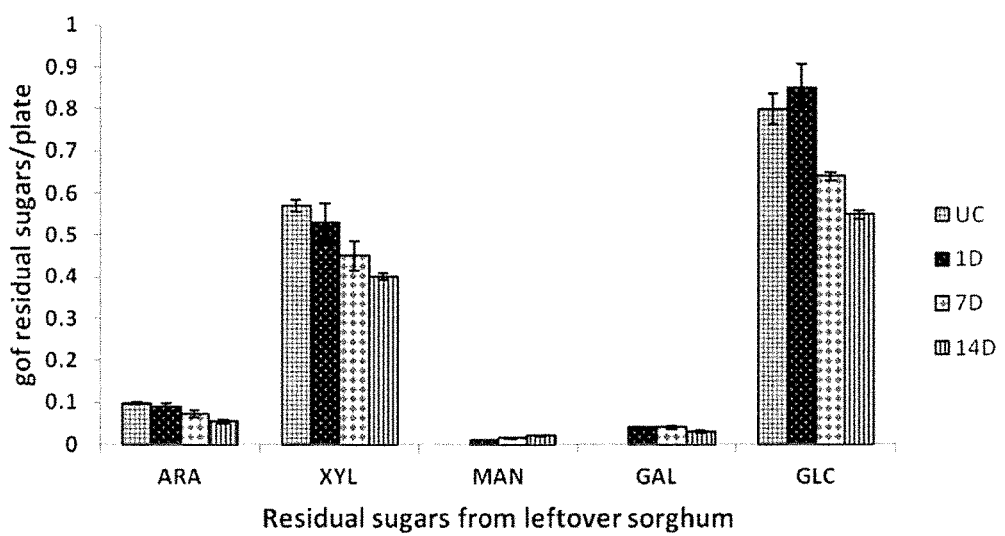
FIG. 4 contains a plot of an estimate of residual sugars of sorghum collected from *A. nidulans* grown on sorghum. The sugar quantities were estimated using Saeman hydrolysis. The results depict residual sugars of sorghum after fungi had utilized sorghum sugars for 1, 7 and 14 days. The utilization of sugars was calculated by subtracting the values in g of total sugars each day from g of sugars from uninoculated controls. On the X-axis the different residual sugars left behind on the plates after fungal growth for the aforementioned days are shown, and on the Y-axis the amount of sugars are represented as g of sugars/plate. Controls are designated as UC, which represents sorghum samples treated in the same way but without any fungal inoculation. Data represent mean±SE and the error bars show the standard deviation.
Figure 5:
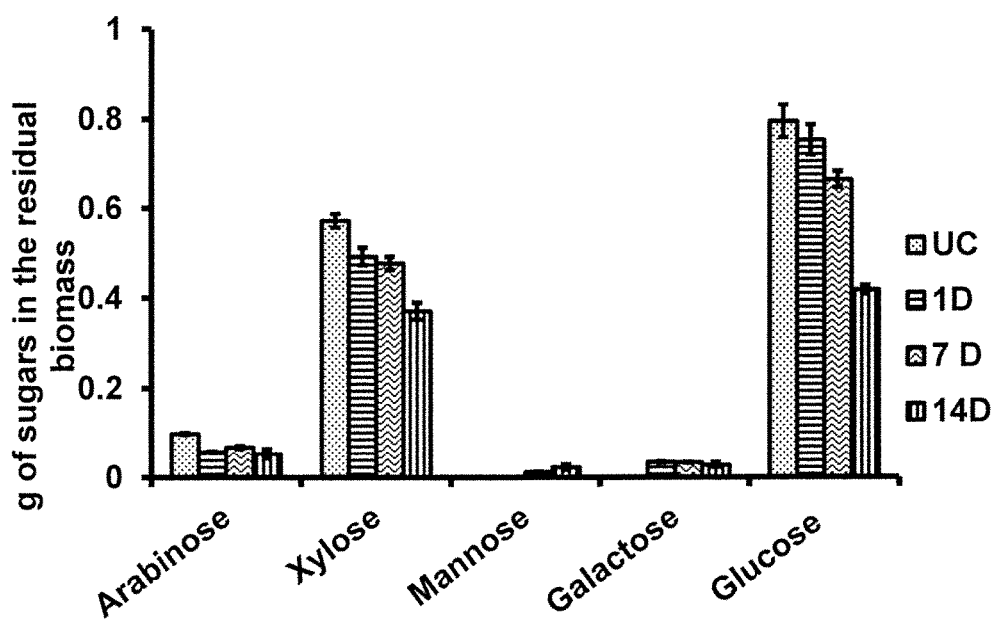
FIG. 5 contains a graph that illustrates an estimate of the amount of each sugar type remaining after growth of *Phanerochaete chrysosporium* on 3 g of sorghum for 1, 7, and 14 days. Utilization of sugars is calculated by subtracting the values in grams of total sugars on each day from grams of sugars in uninoculated controls. Data represent mean±SE (n=3)

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

The invention generally provides cost effective biocatalysts for the hydrolysis of lignocellulosic biomass, leading to the production of lower cost feedstocks for the manufacture of industrial bio-based products such as biofuels. To that end, genomic and proteomic studies of two fungal species, *Aspergillus nidulans* and *Phanerochaete chrysosporium*, have been carried out, and a wide repertoire of enzymes suitable for complete breakdown of polysaccharides and efficient production of simple sugars from biomass have been identified. Especially when used together as a mixture, the enzyme activities render the cellulose in biomass more accessible to cellulases and allow recovery of simple sugars without pretreatment of the biomass, and thus with minimal production of fermentation inhibitors (a problem with most pretreatments) and reducing the costs associated with pretreatment.

Briefly, custom microarrays were utilized to determine the expression levels of *A. nidulans* and *P. chrysosporium* enzymes active in polysaccharide and lignin degradation during growth on untreated sorghum stover, and to determine the components of stover that are degraded or modified (and to what extent) during the growth of the fungi. An exemplary set of enzymes that were identified and their physical properties are shown in Tables 1-6 (for *A. nidulans*) and in Tables 7-12 (for *P. chrysosporium*). As can be seen, a total of 98 polypeptide/nucleic acid sequences from *Asper-*

*gillus nidulans* and 125 polypeptide/nucleic acid sequences from *Phanerochaete chrysosporium* were identified and characterized. These include cellulases, hemicellulases, pectinases, carbohydrate esterases, chitinases, other classes of polypeptides having cell wall modifying activity, as well as many other proteins associated with hydrolysis of lignocelluloses. Crude cell extracts containing selected enzymes were shown to degrade approximately ⅓ of the cellulose and hemicellulose in untreated sorghum biomass. The activities of enzymes present in the crude cell extracts and mixtures containing multiple enzymes were comparable to or more effective than commercial enzyme preparations containing cellulases and xylanases. In some embodiments, no pretreatment of the biomass is required. This reduces the cost, environmental hazards and inhibitor production that are otherwise involved in pretreatment. (However, in some aspects, one or more steps of pre-treatment may be incorporated into the methods described herein.) This disclosure describes mixtures or blends of these enzymes which are designed to efficiently and synergistically catalyze the breakdown of all or substantially all the crosslinkages of lignocellulosic material. That is, a greater-than-additive effect is observed with the blends. For example, enzymes which degrade lignin and thus disentrap cellulose are combined with enzymes which degrade cellulose. Thus, the longstanding problem of difficulties in freeing cellulose from the crystalline lignocellulosic network, to make it accessible to digestion, is solved, without resorting to harsh pretreatment measures.

TABLE 1

Identified hemicellulose-degrading proteins and spectrum counts on 1, 3, 7, and 14 days.

| Accession number[a] | GH Family[a] | Identified proteins[a] | MW (kDa)[b] | Spectrum Count[c] | | | | SignalP[d] |
|---|---|---|---|---|---|---|---|---|
| | | | | Day 1 | Day 3 | Day 7 | Day 14 | |
| AN8401 | GH3 | beta-1,4-xylosidase | 82 | 60 | 98 | 107 | 132 | Y |
| AN2217 | GH3 | beta 1,4-Xylosidase | 83 | 39 | 48 | 58 | 79 | Y |
| AN2359 | GH3 | beta-xylosidase | 87 | 53 | 115 | 57 | 0 | Y |
| AN1818 | GH10 | beta-1,4-endoxylanase | 34 | 101 | 142 | 576 | 720 | Y |
| AN7401 | GH10 | beta-1,4-endoxylanase | 38 | 0 | 4 | 11 | 31 | Y |
| AN3613 | GH11 | beta-1,4-endoxylanase A precursor | 24 | 188 | 174 | 194 | 140 | Y |
| AN7152 | GH27 | alpha-1,4-galactosidase | 69 | 67 | 138 | 124 | 121 | Y |
| AN8138 | GH36 | alpha-1,4-galactosidase | 82 | 0 | 0 | 27 | 24 | Y |
| AN7117 | GH39 | Xylosidase | 50 | 0 | 9 | 13 | 12 | Y |
| AN8007 | GH43 | Endoarabinase | 34 | 6 | 29 | 20 | 19 | Y |
| AN2533 | GH43 | alpha N-arabinofuranosidase | 36 | 0 | 13 | 10 | 7 | Y |
| AN7781 | GH43 | arabinosidase, putative | 38 | 32 | 74 | 52 | 60 | Y |
| AN2534 | GH43 | Endoarabinase | 41 | 0 | 13 | 12 | 7 | Y |
| AN10919 | GH43 | 1,4-endoxylanase D precursor | 42 | 2 | 39 | 50 | 48 | Y |
| AN7313 | GH43 | alpha L-arabinofuranosidase C | 52 | 0 | 5 | 0 | 0 | Y |
| AN7275 | GH43 | Putative xylosidase | 55 | 0 | 0 | 0 | 24 | Y[e] |
| AN8477 | GH43 | Xylosidase/arabinofuranosidase | 60 | 37 | 69 | 64 | 97 | N[f] |
| AN5727 | GH53 | beta-1,4-endogalactanase | 41 | 11 | 19 | 16 | 18 | Y |
| AN1571 | GH54 | alpha-arabinofuranosidase | 53 | 45 | 98 | 80 | 96 | Y |
| AN2632 | GH62 | Arabinoxylan/arabinofuranohydrolase | 33 | 13 | 30 | 29 | 21 | Y |
| AN7908 | GH62 | Arabinoxylan/arabinofuranohydrolase | 36 | 27 | 106 | 90 | 113 | Y |
| AN9286 | GH67 | alpha-glucuronidase | 94 | 14 | 17 | 69 | 104 | Y |
| AN5061 | GH74 | xyloglucanase | 88 | 0 | 0 | 0 | 7 | Y |
| AN2060 | GH93 | exo-arabinanase | 43 | 17 | 24 | 24 | 27 | Y |
| AN6093 | CE1 | Acetyl xylan esterase | 34 | 0 | 9 | 6 | 4 | Y |
| AN1320 | | beta-14-endoxylanase B | 28 | 10 | 36 | 46 | 55 | Y |
| AN6673 | | alpha-fucosidase | 92 | — | — | 30 | 31 | Y |
| AN9380 | | Bifunctional xylanase/deacetylase | 26 | 10 | 6 | 9 | 14 | Y |

[a] Accession numbers along with protein information and glycosyl hydrolase (GH) family information was obtained from Pedant (website located at pedant.gsf.de)
[b] Hypothetical molecular weight of the proteins.
[c] Quantifying changes in protein abundance between samples from different time points was done using the spectral count method, yielding a semiquantitative analysis.
[d] SignalP was used to predict secretion signals (Pedant Database, website located at pedant.gsf.de).
[e] SignalP as reported at *Aspergillus* genome database (wesite located at aspergillusgenome.org)
[f] Not found by SignalP (N-terminal may be incorrectly annotated, a novel signal peptide may be present, or the protein is normally intracellular but was released by autolysis).

TABLE 2

Identified cellulose-degrading proteins and spectrum counts on 1, 3, 7, and 14 days.

| Accession number[a] | GH Family[a] | Identified proteins[a] | MW (kDa)[b] | Spectrum Count[a] | | | | SignalP[d] |
|---|---|---|---|---|---|---|---|---|
| | | | | Day 1 | Day 3 | Day 7 | Day 14 | |
| AN9183 | GH1 | beta-1,4-glucosidase | 66 | 11 | 14 | 22 | 14 | Y |
| AN2227 | GH3 | beta-1,4-glucosidase | 92 | 9 | 0 | 0 | 0 | N[f] |
| AN2828 | GH3 | beta-1,4-glucosidase | 78 | 33 | 144 | 131 | 156 | Y |
| AN4102 | GH3 | beta glucosidase | 92 | 78 | 222 | 204 | 215 | Y |

TABLE 2-continued

Identified cellulose-degrading proteins and spectrum counts on 1, 3, 7, and 14 days.

| Accession number[a] | GH Family[a] | Identified proteins[a] | MW (kDa)[b] | Spectrum Count[c] Day 1 | Day 3 | Day 7 | Day 14 | SignalP[d] |
|---|---|---|---|---|---|---|---|---|
| AN5976 | GH3 | beta glucosidase | 89 | 53 | 105 | 22 | 0 | Y |
| AN7396 | GH3 | beta glucosidase | 84 | 0 | 116 | 107 | 59 | Y |
| AN1804 | GH3 | beta-1,4-glucosidase | 68 | 4 | 4 | 49 | 31 | Y |
| AN10482 | GH3 | beta-1,4-glucosidase | 94 | 0 | 9 | 21 | 10 | Y |
| AN1285 | OHS | beta-1,4-endoglucanase | 36 | 21 | 49 | 38 | 42 | Y |
| AN8068 | GHS | Putative endoglucanase | 63 | 0 | 20 | 46 | 28 | Y |
| AN9166 | GHS | cellulase family protein | 45 | 0 | 9 | 0 | 5 | Y |
| AN1273 | GH6 | Cellobiohydrolase | 41 | 12 | 37 | 23 | 39 | Y |
| AN5282 | GH6 | Cellobiohydrolase | 47 | 0 | 15 | 49 | 54 | Y |
| AN0494 | GH7 | Cellobiohydrolase | 56 | 15 | 33 | 58 | 80 | Y |
| AN5176 | GH7 | Cellobiohydrolase | 48 | 63 | 142 | 195 | 234 | Y |
| AN3418 | GH7 | beta-1,4-endoglucanase | 46 | 65 | 82 | 76 | 88 | Y |
| AN2664 | GH43 | beta-glucanase, putative | 55 | 0 | 0 | 0 | 7 | Y |
| AN3046 | GH61 | endoglucanase, putative | 32 | 44 | 0 | 0 | 0 | Y |
| AN3860 | GH61 | Endoglucanase IV precursor | 26 | 5 | 0 | 14 | 17 | Y |
| AN10419 | GH61 | beta-1,4-endoglucanase | 29 | 0 | 10 | 10 | 16 | Y |
| AN6428 | GH61 | endoglucanase 4 | 24 | 2 | 0 | 5 | 7 | Y |
| AN5282 | | cellobiohydrolase | | | | | | |

[a]Accession numbers along with protein information and glycosyl hydrolase (GH) family information was obtained from Pedant (website located at pedant.gsf.de)
[b]Hypothetical molecular weight of the proteins.
[c]Quantifying changes in protein abundance between samples from different time points was done using the spectral count method, yielding a semiquantitative analysis.
[d]SignalP was used to predict secretion signals (Pedant Database; website located at pedant.gsf.de)
[e]SignalP as reported at *Aspergillus* genome database (wesite located at aspergillusgenome.org)
[f]Not found by SignalP (N-terminal may be incorrectly annotated, a novel signal peptide may be present, or the protein is normally intracellular but was released by autolysis).

TABLE 3

Identified pectin-degrading proteins and spectrum counts on 1, 3, 7, and 14 days.

| Accession number[a] | GH Family[a] | Identified proteins[a] | MW (kDa)[b] | Spectrum Count[b] Day 1 | Day 3 | Day 7 | Day 14 | SignalP[d] |
|---|---|---|---|---|---|---|---|---|
| AN2463 | GH2 | beta-galactosidase | 115 | 0 | 0 | 50 | 96 | N[f] |
| AN2395 | GH2 | beta-galactosidase/mannosidase | 69 | 25 | 70 | 83 | 81 | Y |
| AN8761 | GH28 | Exopolygalaturonase | 48 | 49 | 38 | 18 | 0 | Y |
| AN8891 | GH28 | Exopolygalaturonase | 49 | 30 | 20 | 0 | 0 | Y |
| AN10274 | GH28 | exo-polygalacturonase, putative | 46 | 0 | 4 | 0 | 0 | Y |
| AN0980 | GH35 | beta-galactosidase | 109 | 2 | 14 | 8 | 25 | Y |
| AN0756 | GH35 | beta-galactosidase | 109 | 0 | 5 | 2 | 8 | Y |
| AN7151 | GH78 | alpha-rhamnosidase | 100 | 4 | 14 | 64 | 83 | N[f] |
| AN7828 | GH88 | Unsaturated rhamnogalacturonan hydrolase | 44 | 11 | 0 | 0 | 0 | Y |
| AN9383 | GH105 | unsaturated rhamnogalacturonan hydrolase | 43 | 92 | 54 | 60 | 39 | Y |
| AN0741 | PL1 | Pectate lyase precursor | 35 | 7 | 41 | 28 | 41 | Y |
| AN2331 | PL1 | Pectin lyase A precursor | 41 | 17 | 0 | 0 | 0 | Y |
| AN2569 | PL1 | Pectin lyase A precursor | 39 | 32 | 29 | 47 | 31 | Y |
| AN7646 | PL1 | Pectate lyase A | 35 | 4 | 3 | 19 | 18 | Y |
| AN6106 | PL3 | Pectate lyase C | 26 | 6 | 22 | 20 | 23 | Y |
| AN8453 | PL3 | Pectate lyase C | 28 | 10 | 0 | 5 | 3 | Y |
| AN7135 | PL4 | rhamnogalaturonan lyase | 56 | 13 | 71 | 71 | 80 | Y |
| AN4139 | PL4 | rhamnogalaturonan lyase | 117 | 6 | 15 | 3 | 5 | Y |
| AN3390 | CE8 | pectin methylesterase | 35 | 0 | 19 | 11 | 16 | Y |
| AN4860 | CE8 | pectin methylesterase | 42 | 27 | 3 | 0 | 0 | Y |
| AN2528 | CE12 | rhamnogalaturonan acetyl esterase | 26 | 4 | 0 | 16 | 16 | Y |
| AN2537 | | exopolygalacturonate lyase | 44 | 4 | 12 | 6 | 5 | Y |

[a]Accession numbers along with protein information and glycosyl hydrolase (GH) family information was obtained from Pedant (website located at pedant.gsf.de).
[b]Hypothetical molecular weight of the proteins.
[c]Quantifying changes in protein abundance between samples from different time points was done using the spectral count method, yielding a semiquantitative analysis.
[d]SignalP was used to predict secretion signals.
[e]SignalP as reported at *Aspergillus* genome database (wesite located at aspergillusgenome.org)
[f]Not found by SignalP (N-terminal may be incorrectly annotated, a novel signal peptide may be present, or the protein is normally intracellular but was released by autolysis).

TABLE 4

Identified starch degrading proteins and spectrum counts on 1, 3, 7, and 14 days.

| Accession number[a] | GH Family[a] | Identified proteins[a] | MW (kDa)[b] | Spectrum Count[c] Day 1 | Day 3 | Day 7 | Day 14 | SignalP[d] |
|---|---|---|---|---|---|---|---|---|
| AN3388 | GH13 | alpha amylase | 50 | 33 | 0 | 49 | 41 | Y |
| AN3402 | GH13 | alpha amylase | 69 | 11 | 0 | 0 | 0 | Y |
| AN7402 | GH15 | glucoamylase | 71 | 7 | 43 | 24 | 15 | Y[e] |
| AN2017 | GH31 | alpha-1,4-glucosidase | 110 | 5 | 12 | 5 | 6 | Y |
| AN8953 | GH31 | alpha-1,4-glucosidase B | 108 | 85 | 117 | 95 | 121 | Y |
| AN0941 | GH31 | alpha-1,4-glucosidase | 94 | 23 | 24 | 2 | 5 | Y |

[a]Accession numbers along with protein information and glycosyl hydrolase (GH) family information was obtained from Pedant Database (website located at pedant.gsf.de).
[b]Hypothetical molecular weight of the proteins.
[c]Quantifying changes in protein abundance between samples from different time points was done using the spectral count method, yielding a semiquantitative analysis.
[d]SignalP was used to predict secretion signal (Pedant Database, website located at pedant.gsf.de)
[e]SignalP as reported at *Aspergillus* genome database (wesite located at aspergillusgenome.org)

TABLE 5

Identified fungal cell wall degradation/remodeling proteins and spectrum counts on 1, 3, 7, and 14 days.

| Accession number[a] | GH Family[a] | Identified proteins[a] | MW (kDa)[b] | Spectrum Count[c] Day 1 | Day 3 | Day 7 | Day 14 | SignalP[d] |
|---|---|---|---|---|---|---|---|---|
| AN0933 | GH16 | Extracellular cell wall glucanase | 42 | 18 | 35 | 11 | 7 | Y |
| AN0245 | GH16 | Beta-1,3(4)-endoglucanase, putative | 37 | 0 | 33 | 15 | 29 | Y |
| AN6620 | GH16 | Beta-1,3(4)-endoglucanase, putative | 42 | 4 | 0 | 0 | 0 | Y |
| AN6819 | GH16 | Endo-1,3 (4)-glucanase | 32 | 9 | 7 | 8 | 7 | Y |
| AN7950 | GH17 | Cell wall beta-1,3-endoglucanase | 47 | 17 | 32 | 32 | 26 | Y |
| AN4871 | GH18 | Protein similar to class V chitinase A | 44 | 5 | 224 | 277 | 317 | N[f] |
| AN8241 | GH18 | class III Chi A chitinase | 97 | 0 | 5 | 2 | 0 | Y |
| AN1502 | GH20 | Protein similar to N-acetylglucosaminidase | 68 | 11 | 101 | 124 | 176 | Y |
| AN0779 | GH55 | Putative beta-1,3-exoglucanase | 84 | 0 | 19 | 19 | 15 | Y |
| AN4825 | GH55 | Glucan 1,3-beta glucosidase precursor | 97 | 0 | 102 | 108 | 135 | Y |
| AN9042 | GH71 | putative alpha 1,3- glucanase | 69 | 0 | 51 | 55 | 60 | Y |
| AN7657 | GH72 | 1,3-beta-glucanosyltransferase | 49 | 14 | 37 | 0 | 4 | Y |
| AN0472 | GH81 | Putative beta-1,3-endoglucanase | 98 | 0 | 102 | 99 | 146 | Y |
| AN9339 | | Catalase B precursor | 79 | 58 | 111 | 109 | 108 | Y |
| AN4390 | | GPI-anchored cell wall organization protein Ecm33 | 41 | 4 | 7 | — | — | Y |
| AN2385 | | GPI anchored beta-1,3(4)-endoglucanase, putative | 65 | 3 | — | — | — | Y |

[a]Accession numbers along with protein information and glycosyl hydrolase (GH) family information was obtained from Pedant (website located at pedant.gsf.de).
[b]Hypothetical molecular weight of the proteins.
[c]Quantifying changes in protein abundance between samples from different time points was done using the spectral count method, yielding a semiquantitative analysis.
[d]SignalP was used to predict secretion signals (Pedant Database, website located at pedant.gsf.de)
[e]SignalP as reported at *Aspergillus* genome database (wesite located at aspergillusgenome.org).
[f]Not found by SignalP (N-terminal may be incorrectly annotated, a novel signal peptide may be present, or the protein is normally intracellular but was released by autolysis).

TABLE 6

Identified proteins involved in various plant cell wall modifications and spectrum counts on 1, 3, 7, and 14 days.

| Accession number[a] | GH Family[a] | Identified proteins[a] | MW (kDa)[b] | Spectrum Count[c] Day 1 | Day 3 | Day 7 | Day 14 | SignalP[d] |
|---|---|---|---|---|---|---|---|---|
| AN1772 | CE1 | feruloyl esterase type B | 58 | 105 | 148 | 154 | 142 | Y |
| AN5267 | | feruloyl esterase | 28 | 21 | 12 | 56 | 65 | Y |

TABLE 6-continued

Identified proteins involved in various plant cell wall modifications and spectrum counts on 1, 3, 7, and 14 days.

| Accession number[a] | GH Family[a] | Identified proteins[a] | MW (kDa)[b] | Spectrum Count[c] Day 1 | Day 3 | Day 7 | Day 14 | Signal P[d] |
|---|---|---|---|---|---|---|---|---|
| AN5311 | | Putative tyrosinase | 42 | 14 | 10 | 19 | 19 | Y |
| AN7230 | | Cellobiose dehydrogenase | 83 | 0 | 17 | 39 | 77 | Y |

[a]Accession numbers along with protein information and glycosyl hydrolase (GH) family information was obtained from Pedant (website located at pedant.gsf.de)
[b]Hypothetical molecular weight of the proteins.
[c]Quantifying changes in protein abundance between samples from different time points was done using the spectral count method, yielding a semiquantitative analysis.
[d]SignalP was used to predict secretion signals (Pedant Database, website located at pedant.gsf.de)

TABLE 7

Identified cellulose degrading proteins and spectrum counts on 1D, 7D and 14D.

| Identified proteins[a] | Accession no.[a] | M. Wt.[b] | Spectrum count[c] 1D | 7D | 14D | SignalP[d] |
|---|---|---|---|---|---|---|
| Endoglucanase | phch_06389 | 36 kDa | 2 | 25 | 32 | Yes |
| Endoglucanase | phch_09443 | 28 kDa | 14 | 13 | 18 | Yes |
| Endoglucanase (GH5) | phch_05701 | 86 kDa | 7 | 39 | 38 | Yes |
| Endoglucanase (GH5) | phch_08142 | 40 kDa | 5 | 56 | 61 | Yes |
| Endoglucanase (GH12) | phch_08801 | 27 kDa | 16 | 21 | 22 | Yes |
| Endoglucanase (GH12) | phch_10406 | 26 kDa | 17 | 11 | 6 | Yes |
| Endoglucanase (GH45) | phch_10120 | 15 kDa | 0 | 14 | 15 | Yes |
| Endoglucanase (GH61) | phch_01789 | 24 kDa | 60 | 46 | 46 | Yes |
| Endoglucanase (GH61) | phch_04629 | 32 kDa | 4 | 9 | 11 | Yes |
| Endoglucanase (GH61) | phch_06067 | 26 kDa | 25 | 14 | 5 | Yes |
| Endoglucanase (GH61) | phch_06115 | 33 kDa | 2 | 10 | 11 | Yes |
| Endoglucanase (GH61) | phch_06068 | 25 kDa | 12 | 11 | 8 | Yes |
| Endoglucanase (GH61) | phch_04595 | 21 kDa | 0 | 3 | 8 | Yes |
| Endoglucanase (GH61) | phch_07005 | 44 kDa | 0 | 3 | 0 | Yes |
| Endoglucanase (GH74) | phch_03254 | 79 kDa | 34 | 46 | 42 | Yes |
| Endoglucanase (GH74) | phch_08477 | 86 kDa | 8 | 91 | 117 | Yes |
| Cellobiohydrolase | phch_04333 | 23 kDa | 4 | 9 | 12 | Yes |
| Cellobiohydrolase II (GH6) | phch_00596 | 48 kDa | 19 | 48 | 66 | Yes |
| Cellobiohydrolase (GH7) | phch_02696 | 54 kDa | 18 | 89 | 97 | Yes |
| Cellobiohydrolase (GH7) | phch_09634 | 63 kDa | 21 | 100 | 81 | Yes |
| Cellobiose dehydrogenase | phch_08874 | 81 kDa | 61 | 72 | 70 | Yes |
| β-glucosidase (GH3) | phch_08014 | 22 kDa | 0 | 7 | 6 | Yes |
| β-glucosidase (GH3) | phch_08013 | 51 kDa | 5 | 8 | 8 | Yes |
| β-glucosidase (GH3) | phch_01322 | 99 kDa | 11 | 24 | 10 | Yes |
| β-glucosidase | phch_09956 | 94 kDa | 18 | 70 | 67 | Yes |
| Expansin | phch_08274 | 34 kDa | 11 | 3 | 1 | Yes |

TABLE 8

Identified hemicellulose degrading proteins and spectrum counts on 1D, 7D and 14D.

| Identified proteins[a] | Accession no.[a] | M. wt.[b] | Spectrum count[c] 1D | 7D | 14D | SignalP[d] |
|---|---|---|---|---|---|---|
| β-xylosidase (GH3) | phch_02332 | 84 kDa | 0 | 28 | 38 | Yes |
| β-xylosidase (GH3) | phch_11331 | 82 kDa | 7 | 71 | 51 | Yes |
| Putative Xylanase (GH5) | phch_07139 | 52 kDa | 0 | 24 | 21 | Yes |
| β-mannanase (GH5) | phch_1 0660 | 49 kDa | 0 | 10 | 11 | Yes |
| β-mannanase (GH5) | phch_06575 | 46 kDa | 14 | 14 | 14 | Yes |
| Endo-1,4-6-xylanase (GH10) | phch_09716 | 38 kDa | 0 | 8 | 0 | Yes |
| Endo-1,4-β-xylanase (GH10) | phch_08796 | 39 kDa | 25 | 52 | 52 | Yes |
| Endo-1,4-β-xylanase (GH11) | phch_04974 | 30 kDa | 0 | 15 | 12 | Yes |
| Endo-1,4-β-xylanase (GH43) | phch_01155 | 34 kDa | 0 | 12 | 1 | Yes |
| Acetylxylan esterase | phch_09006 | 38 kDa | 17 | 28 | 26 | Yes |
| Acetylxylan esterase | phch_06569 | 39 kDa | 16 | 25 | 28 | Yes |
| α-L-arabino-furanosidase | phch_04260 | 64 kDa | 2 | 30 | 41 | Yes |
| Glucuronoyl esterase | phch_10701 | 49 kDa | 15 | 27 | 24 | Yes |
| Glucuronoyl esterase | phch_08173 | 44 kDa | 0 | 22 | 9 | Yes |
| β-mannosidase | phch_11132 | 106 kDa | 0 | 36 | 23 | Yes |
| α-fucosidase | phch_08741 | 132 kDa | 0 | 3 | 4 | Yes |

TABLE 9

Identified pectin degrading proteins and spectrum counts on 1D, 7D and 14D.

| Identified proteins[a] | Accession no.[a] | M. wt.[b] | Spectrum count[c] 1D | 7D | 14D | SignalP[d] |
|---|---|---|---|---|---|---|
| Endo-polygalacturonase (GH28) | phch_04434 | 45 kDa | 34 | 78 | 59 | Yes |
| Rhamnogalacturonan hydrolase (GH28) | phch_09702 | 65 kDa | 0 | 43 | 45 | Yes* |
| Exo-polygalacturonase (GH28) | phch_04422 | 40 kDa | 0 | 18 | 10 | Yes |
| Galactan 1,3-β-galactosidase (GH43) | phch_00342 | 35 kDa | 8 | 18 | 14 | Yes |
| β-glucuronidase (GH79) | phch_02342 | 63 kDa | 0 | 6 | 5 | Yes |
| Pectinmethylesterase | phch_06938 | 37 kDa | 0 | 6 | 4 | Yes |
| Pectinmethylesterase | phch_10539 | 38 kDa | 0 | 7 | 14 | Yes |
| α-L-rhamnosidase B | phch_06967 | 66 kDa | 0 | 12 | 10 | Yes |

TABLE 10

Identified lignin degrading proteins and spectrum counts on 1D, 7D and 14D.

| Identified proteins [a] | Accession no.[a] | M. Wt.[b] | Spectrum count[c] 1D | 7D | 14D | SignalP[d] |
|---|---|---|---|---|---|---|
| Cellobiose dehydrogenase | phch_08874 | 81 kDa | 61 | 72 | 70 | Yes |
| Glyoxaloxidase 1 | phch_08719 | 82 kDa | 4 | 17 | 5 | Yes |
| Aryl alcohol oxidase | phch_07802 | 63 kDa | 20 | 4 | 1 | Yes |
| Lignin peroxidase | phch_10892 | 40 kDa | 0 | 18 | 4 | Yes |
| Lignin peroxidase | phch_07353 | 39 kDa | 0 | 11 | 0 | Yes |
| Lignin peroxidase | phch_04179 | 52 kDa | 0 | 18 | 7 | Yes |
| Glyoxal oxidase | phch_10903 | 92 kDa | 0 | 2 | 5 | Yes |
| Mannose 6 phosphatase | phch_03961 | 38 kDa | 0 | 75 | 52 | Yes |

TABLE 11

Identified fungal cell wall turnover/remodeling proteins and spectrum counts on 1D, 7D and 14D.

| Identified proteins [a] | Accession no.[a] | M. wt.[b] | Spectrum count[c] 1D | 7D | 14D | SignalP[d] |
|---|---|---|---|---|---|---|
| Glycophospholipid-anchored surface glycoprotein (GH5) | phch_08115 | 76 kDa | 1 | 10 | 8 | Yes |
| O-glucosyl hydrolase (GH5) | phch_01650 | 40 kDa | 15 | 0 | 0 | Yes |
| Chitinase (GH18) | phch_08872 | 49 kDa | 0 | 19 | 24 | Yes |
| Chitinase (GH18) | phch_03794 | 50 kDa | 0 | 2 | 0 | Yes |
| Chitinase (GH18) | phch_04825 | 60 kDa | 8 | 12 | 9 | Yes |
| β-1,6-glucanase (GH30) | phch_11061 | 64 kDa | 0 | 14 | 12 | Yes |
| α-glucosidase (GH31) | phch_07957 | 106 kDa | 28 | 61 | 60 | Yes |
| Trehalase (GH37) | phch_10486 | 81 kDa | 3 | 15 | 9 | Yes |
| α-1,2-mannosidase (GH47) | phch_05897 | 125 kDa | 0 | 23 | 6 | Yes |
| α 1,2 mannosidase (GH92) | phch_04016 | 78 kDa | 0 | 61 | 77 | Yes |
| α-1,2-mannosidase (GH92) | phch_02266 | 84 kDa | 0 | 23 | 12 | Yes |
| Endo-1,3(4)-β-glucanase (Laminarinase) (fungal cell wall) | phch_05048 | 34 kDa | 32 | 35 | 29 | Yes |
| Endo-1,3(4)-β-glucanase | phch_09494 | 33 kDa | 5 | 21 | 22 | Yes |
| Endo-1,3(4)-β-glucanase | phch_03076 | 36 kDa | 20 | 0 | 0 | Yes |
| Chitin deacetylase | phch_03098 | 51 kDa | 14 | 0 | 0 | Yes |
| Glyco-mannoprotein | phch_06172 | 41 kDa | 0 | 3 | 2 | Yes |
| Mannoprotein | phch_06352 | 39 kDa | 0 | 7 | 0 | Yes |

TABLE 12

Identified miscellaneous proteins and spectrum counts on 1D, 7D and 14D.

| Identified proteins [a] | Accession no.[b] | M. wt.[b] | Spectrum count[c] 1D | 7D | 14D | SignalP[d] |
|---|---|---|---|---|---|---|
| Glutaminase A | phch_01769 | 76 kDa | 48 | 61 | 53 | Yes |
| Aldose 1-epimerase | phch_03451 | 42 kDa | 29 | 27 | 20 | Yes |
| Cathepsin d (lysosomal aspartyl protease) | phch_10408 | 44 kDa | 0 | 8 | 1 | Yes |
| Aspartyl protease | phch_10410 | 44 kDa | 0 | 26 | 25 | Yes |
| Aspartyl protease | phch_03957 | 42 kDa | 0 | 10 | 5 | Yes |
| Aspartyl protease | phch_01483 | 44 kDa | 0 | 7 | 15 | Yes |
| Aspartate protease | phch_10409 | 45 kDa | 0 | 21 | 16 | Yes |
| Subtilisin-like serine protease | phch_04912 | 93 kDa | 0 | 10 | 7 | Yes |
| Protease inhibitor | phch_08575 | 22 kDa | 0 | 5 | 0 | Yes |
| Tripeptidyl-peptidase I | phch_11653 | 67 kDa | 0 | 9 | 1 | Yes |
| Tripeptidyl-peptidase I | phch_01173 | 59 kDa | 0 | 28 | 19 | Yes |
| Tripeptidyl-peptidase I | phch_02919 | 57 kDa | 3 | 13 | 6 | Yes |
| Peptidase S41 family protein | phch_03902 | 73 kDa | 2 | 10 | 2 | Yes |
| Aspartic proteinase | phch_09076 | 42 kDa | 0 | 9 | 0 | Yes |
| Aspartic proteinase | phch_05555 | 54 kDa | 0 | 2 | 0 | Yes |
| Acid proteinase | phch_04703 | 27 kDa | 0 | 17 | 2 | Yes |
| Triacylglycerol lipase | phch_11043 | 33 kDa | 1 | 5 | 7 | Yes |
| Lipase/acylhydrolase | phch_05097 | 35 kDa | 0 | 9 | 1 | Yes |
| Lipase/acylhydrolase | phch_03623 | 43 kDa | 0 | 12 | 22 | Yes |
| Lipase/acylhydrolase | phch_07244 | 47 kDa | 18 | 18 | 13 | Yes |
| Lipase/acylhydrolase | phch_00684 | 31 kDa | 17 | 7 | 3 | Yes |
| Lipase | phch_02961 | 31 kDa | 13 | 5 | 5 | Yes |
| Lipase 2 | phch_09208 | 52 kDa | 0 | 30 | 4 | Yes |
| Lipase 2 | phch_10475 | 59 kDa | 0 | 3 | 0 | Yes |
| Ribonuclease T1 | phch_08818 | 15 kDa | 0 | 4 | 0 | Yes |
| Ribonuclease M | phch_09080 | 39 kDa | 1 | 3 | 0 | Yes |
| Serine/threonine-protein kinase | phch_08823 | 78 kDa | 0 | 4 | 0 | Yes |
| Polysaccharide lyase family 8 | phch_08449 | 85 kDa | 0 | 8 | 6 | Yes |
| Expansin | phch_08274 | 34 kDa | 11 | 3 | 1 | Yes |
| Alpha-amylase A | phch_00789 | 59 kDa | 19 | 0 | 0 | Yes |
| Glucoamylase precursor | phch_06589 | 61 kDa | 2 | 8 | 24 | Yes |
| Alpha-amylase | phch_07004 | 58 kDa | 0 | 6 | 1 | Yes |

TABLE 12-continued

Identified miscellaneous proteins and spectrum counts on 1D, 7D and 14D.

| Identified proteins [a] | Accession no.[b] | M. wt.[b] | Spectrum count [c] | | | SignalP[d] |
|---|---|---|---|---|---|---|
| | | | 1D | 7D | 14D | |
| Hexose transport-related protein | phch_06673 | 113 kDa | 2 | 5 | 0 | Yes |
| Malate dehydrogenase | phch_02383 | 29 kDa | 0 | 8 | 1 | Yes |
| Glycoside hydrolase family 5 | phch_07139 | 52 kDa | 0 | 24 | 21 | Yes |
| Glycoside hydrolase family 79 | phch_02342 | 63 kDa | 0 | 6 | 5 | Yes |
| Acid phosphatase | phch_07186 | 34 kDa | 0 | 17 | 13 | Yes |
| Alpha-galactosidase | phch_05754 | 37 kDa | 0 | 11 | 12 | Yes |
| Alpha-galactosidase | phch_08025 | 76 kDa | 0 | 12 | 21 | Yes |
| Carboxypeptidase 2 | phch_03930 | 46 kDa | 0 | 7 | 2 | Yes |
| Nuclease Le3 | phch_10984 | 34 kDa | 0 | 17 | 12 | Yes |
| SnodProt1 | phch_10120 | 15 kDa | 0 | 14 | 15 | Yes |
| Hypothetical protein | phch_07324 | 52 kDa | 0 | 4 | 0 | Yes |
| Hypothetical protein | phch_01640 | 54 kDa | 0 | 21 | 23 | Yes |
| Hypothetical protein | phch_10764 | 99 kDa | 0 | 26 | 21 | Yes |
| Hypothetical protein | phch_01136 | 33 kDa | 0 | 23 | 18 | Yes |
| Hypothetical protein | phch_04262 | 40 kDa | 0 | 12 | 4 | Yes |
| Hypothetical protein | phch_02529 | 15 kDa | 2 | 5 | 4 | Yes |
| Hypothetical protein | phch_07380 | 108 kDa | 3 | 31 | 15 | Yes |
| Hypothetical protein | phch_04700 | 14 kDa | 28 | 40 | 27 | Yes |

[a]Accession numbers along with protein information and glycoside hydrolase family information was obtained from Pedant (website located at pedant.gsf.de/).
[b]Molecular weight of the proteins was determined theoretically.
[c]Quantifying changes in protein abundance between samples from different time points was done using the spectral count method, yielding a semi-quantitative analysis.
[d]SignalP was used to predict secretion signals (see the website located at www.cbs.dtu.dk/services/SignalP/). Additional information for the presence of a signal peptide was obtained by accessing the following URL with the model number, e.g. genome.jgi-psf.org/cgi-bin/dispGeneModel?db=Phchr1&id=3651

The following definitions are used throughout:

Biomass is biological material derived from living, or recently living organisms. In the context of energy production, biomass refers to plant based material.

Lignocellulose: any of several closely related substances constituting the essential part of woody cell walls of plants and consisting of cellulose intimately associated with lignin.

Synthetic medium: a medium or carrier that is formulated so as to be suitable for delivering enzymes or microorganisms encoding enzymes to biomass for digestion. Synthetic media may contain nutrients, stabilizing agents, buffering agents, salts, etc. and may be liquid (solutions, dispersions, suspensions, etc.) or solid (the enzymes and/or microorganisms may be lyophilized).

In some aspects, this disclosure provides compositions comprising enzyme blends ("cocktails") of two or more of the enzymes as disclosed herein for efficient and cost effective methods of degrading lignocelluloses, especially lignocellulose that has not been pretreated. The GenBank Accession numbers corresponding to the enzymes are provided in Tables 1-12. The enzymes in a mixture may all be from the same fungus, or the enzymes may be a mix of enzymes from the two different fungi, P. chrysosporium and A. nidulans. Exemplary cloned nucleic acids sequences encoding the enzymes are presented in SEQ ID NOS: 1-20 and exemplary amino acid sequences of the encoded enzymes are presented in SEQ ID NOS: 21-40. Derivatives of those enzymes, as described in detail below, are also encompassed.

In some aspects, the mixtures are those which are produced when an organism (or organisms) synthesize(s) the enzymes and secretes them into surrounding growth media e.g. the mixtures are extracellular filtrates, (ECFs), or modifications thereof. Such a "mixture" can be of any suitable form. For example, the mixture may be or may comprise one or more ECFs from a microorganism that produces the enzymes of interest (e.g. a native or recombinant organism that produces several enzymes of interest), or may comprise a mixture of ECFs from multiple microorganisms, either native or recombinant, that collectively produce the enzymes, (e.g. a mixture of ECFs from A. nidulans and P. chrysosporium). Such extracts are produced, for example, by growing a suitable microorganism or a plurality of microorganisms that synthesize at least two of the enzymes described herein, and which generally secrete the at least two enzymes into the growth medium or broth. One microorganism may produce all of the at least two enzymes, or only one or the enzymes of the at least two enzymes, or only a few of the at least two enzymes. Generally, the organisms themselves are removed from the extract prior to use, e.g. by centrifugation, filtration, etc. leaving the enzymes in the extract, and the extract may be concentrated and supplemented or modified as needed. ECFs generally include various media components such as salts, buffering agents, vitamins, minerals, etc. and other components. Glycerol may be added, i.e. glycerol stocks of ECF can be prepared to increase shelf life, and/or preservatives such as sodium azide, dithiothreitol (DTT), metal chelators such as EDTA, etc. can be added to an ECF to make it more stable and to preserve or maintain the enzymes in an active form. ECFs may be lyophilized and reconstituted in appropriate buffer for use in biomass digestion reactions. Such extracts may be packaged, shipped and sold for use in the methods described herein.

In other aspects, the enzymes are removed from the medium in which they are produced, i.e. the enzymes are substantially "purified" or "isolated" or partially purified or isolated, so that the proteins are removed or separated from cells, cellular debris, extraneous or unwanted proteins, other macromolecules such as lipids and nucleic acids, and other components of the broth in which they were grown. The proteins are then combined with one of more other biomass-degrading proteins to form a mixture. In these cases, mixtures containing a plurality of (two or more) enzymes are formed by deliberately selecting and mixing together a synthetic "cocktail" with a desired complement or range of enzyme activities. Such mixtures comprise from about 2 to about 20 enzymes, and generally from about 5 to about 15 enzymes. In other words, in some aspects, about 2, 3, 4, 5, 6, 7, 8, 9, 10, 11, 12, 13, 14, 15, 16, 17, 18, 19, or about 20 or more enzymes are combined. The selection of enzymes is generally based on their activity, e.g. on both the substrate specificity and the efficiency and/or other properties (e.g. stability, etc.) of the enzyme, and it is desirable to combine enzymes that are able to digest multiple types of chemical bonds in the biomass so as to digest the biomass as completely as possible.

Exemplary general and specific enzyme combinations are presented below.

Exemplary combinations of types of enzymes based on activity and/or origin:

1) Cellulase+hemicellulase+oxidases from *P. chrysosporium*
2) Cellulase+hemicellulose+pectinase from *A. nidulans*
3) A combination of 1)+2)
4) Cellulases+Hemicellulases+carbohydrate esterases+polysaccharide Lyases
5) Cellulases+Hemicellulases+carbohydrate esterases+polysaccharide Lyases+Lignin Oxidases
6) Cellulases+Hemicellulases+carbohydrate esterases+polysaccharide Lyases+Lignin Oxidases+Lignin degrading auxiliary enzymes
7) Cellulases+Hemicellulases+carbohydrate esterases+polysaccharide Lyases+Lignin Oxidases+Lignin degrading auxiliary enzymes+cellulose degrading auxiliary enzymes Exemplary combinations of particular enzymes; numbers are as presented in Tables 1-12.

1. Endogucanase (GH61)-(phch_01789)+Cellobiohydrolase-(phch_09634)+β-glucosidase (GH3) (phch_01322)+Cellobiose dehydrogenase (phch_08874)
2. Glucuronoyl esterase (phch_10701)+Endo-1,4-β-xylanase (GHI0) (phch_08796)+Acetylxylan esterase (phch_09006)
3. Endo-polygalacturonase (GH28) (phch_04434)+Exo-polygalacturonase (GH28) (phch_04422)+Pectinmethylesterase (phch_06938)
4. Lignin peroxidase (phch_10892)+Glyoxal oxidase (phch_10903)+Cellobiose dehydrogenase (phch_08874)
5. Combinations of (1)+(2)
6. Combinations of (1)+(2)+(4)
7. Combinations of (1)+(2)+(3)+(4).
8. Endo-β(1,4)-xylanase (AN1818)+Cellobiohydrolase-(AN5282)+Feruloyl esterase (AN5267)+LPMO (6428)
9. Endo-β(1,4)-glucanase (AN 1285)+Endo-β(1,4)-glucanase (AN 3418)+Cellobiose dehydrogenase (AN 7230)+Endo-β(1,4)-xylanase (AN1818)+Glucuronoyl esterase (phch_10701)+Lignin peroxidase (phch_10892)+Glyoxal oxidase (phch_10903)
10. Endo-β(1,4)-xylanase (AN1818)+Cellobiohydrolase-(AN5282)+Feruloyl esterase (AN5267)+Pectin lyase (AN2569)+Cellobiose dehydrogenase (phch_08874)+Lignin peroxidase (phch_10892)
11. Endo-β(1,4)-xylanase (AN1818)+Cellobiohydrolase-(AN5282)+Feruloyl esterase (AN5267)+LPMO (6428)+Endo-β(1,4)-glucanase (AN 1285)+Endopolygalacturonase (AN 8327)

Exemplary lignin degrading auxiliary enzymes include but are not limited to aryl alcohol oxidase, glyoxal oxidase, etc. (see Table 4). Exemplary cellulose degrading auxiliary enzymes but are not limited to expansin, monooxygenase, etc. (see Tables 7 and 12). In some aspects, at least a first enzyme from Tables 1-6 and at least a second enzyme from Tables 7-12 are included, but additional enzymes may also be present as described herein, e.g. a third, fourth, fifth, etc. enzyme, up to about 15, or possibly more.

Such mixtures are advantageous in that unnecessary enzymes present in ECFs are not present, and the concentrations and ratios of the enzymes can be adjusted as needed. Those of skill in the art are familiar with protein isolation and purification techniques, e.g. using heat, centrifugation, filtration, size exclusion and affinity chromatography, various protein tags, etc. and will vary depending on whether the enzymes are synthesized naturally from a native source, or as recombinant enzymes from a genetically engineered host. Any suitable technique for isolating the enzymes in an active form may be used, such as those described in the Examples section below. The selected enzymes are combined in a blend or "cocktail" of enzymes and placed in a suitable medium for storage, packaging, shipping, sale, and eventual use by an end-user of the product. The forms of the enzymes may be, for examples, as a liquid or agar stab shipped on dry ice or as a stabilized lyophilized powder.

In further embodiments, an ECF, or a mixture of ECFs, may be supplemented by the addition of one or more isolated lignocellulytic enzymes, isolated either from a native source, or from a recombinant host. For example, one or more recombinant enzymes may be added to an ECF preparation to increase the level of activity of at least one enzyme that is made in a relatively low amount by the organism(s) that produce it.

In other aspects, compositions are provided which comprise one or more microorganisms (e.g. bacteria, fungi, or other hosts, as described below) that produce one or more of the enzymes described herein. The microorganisms may be recombinant and may be genetically engineered to overexpress one or more than one of the enzymes of interest. Alternatively, the organisms may be naturally occurring, e.g. the mixture may comprise *A. nidulans* and *P. chrysosporium*, which are substantially purified, i.e. no other fungi or microorganisms are present in the mixture, so that the mixture is free of other microorganisms, or free of other microorganisms that do not produce at least one of the enzymes described herein. Such compositions differ substantially from natural products, since these two fungi do not grow or occur together in nature, especially not in a synthetic medium such as a liquid suspension, lyophilized solid, etc. and the ratios and/or concentrations of the fungi provided in the mixtures are not found in nature, nor are the media components found in the same form and/or combinations and/or concentrations and/or ratios, or are not found in a form that is free of other extraneous molecules or macromolecules. The compositions comprise synthetic medium suitable to maintain the organisms during packaging, shipping, and storage prior to sale and use. Exemplary media and media components include those described above.

In some aspects, the enzymes and/or the microorganisms that produce them are recombinant, i.e. they are the result of manipulation by genetic engineering techniques. In this aspect, generally the nucleic acid sequences encoding an enzyme (e.g. the gene sequence that encodes an enzyme) is removed from its natural source (the organism in which it occurs in nature) e.g. by cloning, and is introduced into a host organism (e.g. an expression vector) in which it does not occur in nature (a heterologous host from a different species), or in which it is in a different form than that in which it occurs in nature (the host may be homologous host from the same species but the enzyme, and thus the host, is recombinant). For example, genetic sequences encoding the enzymes may be introduced into host organisms such as: a bacterial host such as *Escherichia coli*; various *Bacillus* species (e.g. *B. subtilus*, etc.); *Clostridia* species (e.g. *C. straminisolvens, C. thermocellum*, etc.), various Thermobacilli (e.g. *T. xylanolyticus* etc.), or a yeast such as a Saccharomycete (e.g. *Pichia pastoris*), etc.

In some aspects, fungi (e.g. filamentous fungi) are the preferred recombinant hosts for production of the proteins. They have traditionally been used in a variety of industrial processes and, compared to bacterial and yeast hosts, they can grow on simple and inexpensive substrates and simultaneously produce and secrete a large array of proteins and enzymes, which are considered GRAS (generally regarded as safe). In one aspect, the recombinant host cell is a filamentous fungus, examples of which include but are not limited to: *Aspergillus* species (e.g. *A. niger, A. awamori, A. oryzae, A. nidulans, A. fumigatus*, etc.); *Fusarium* species (e.g. *F. venenatum*, etc.); *Trichodermes* (e.g. *T. reesei* and *T. harzianum*, etc.); *Myceliophthora* (e.g. *M. thermophila*, etc.), *Neurospora* species (e.g. *N. crassa*), *Phanerochaete* species (e.g. *P. chrysosporium*, etc.), and the like. Other suitable host systems include but are not limited to insect cells, plant cells mammalian cells, etc. In addition, a "host" cell need not always be an expression vector but may be a host in which it is useful to place the nucleic acid for some other purpose, e.g. for storage, for ease of manipulation during genetic engineering manipulations, etc.

In some embodiments, the host may be the natural host of the enzyme(s), such as *A. nidulans* and *P. chrysosporium*. However, in such cases, genetic manipulation of the host and/or of the gene encoding the enzyme, may have been performed, e.g. to overexpress the enzyme by, for example, introducing multiple copies of the gene; and/or by placing the gene under control of a different and more powerful or efficient transcriptional control region or promoter; and/or by deleting competing or deleterious sequences from the host, e.g. by deleting sequences encoding proteases that might digest the enzyme; or by introducing a sequence that encodes two or more enzymes in tandem, e.g. as a chimeric or fusion polypeptide; or by some other means for some other goal.

A recombinant host may be genetically engineered to produce 1, 2, 3, 4, or any number of enzymes.

Exemplary synthetic recombinant nucleic acids that are encompassed by the invention include those of SEQ ID NOS: 1-20; exemplary synthetic recombinant proteins that are encompassed by the invention include those of SEQ ID NOS: 21-40;

In some aspects, the at least two enzymes of interest are produced by their natural, native hosts and so are not "recombinant". However, the composition that is used to digest biomass is a composition that is not found in nature in that it comprises a plurality of isolated, at least partially purified, and then combined enzymes which are generally present in a ratio or at concentrations that do not occur in nature, and in a synthetic medium. For example, each of the enzymes may be present at a concentration that is at least 2, 5 or 10-fold or more (e.g. 25, 50, 75, 100-fold or more) higher than occurs in nature, i.e. in either of the two species. In some aspects, at least two of the enzymes are produced by different organisms, e.g. one is produced by *A. nidulans* and the other is produced by *P. chrysosporium*. Thus, the mixture is also not a natural product. Further, the enzymes may be concentrated and/or purified or partially purified, and placed in an artificial growth or other (e.g. a preserving) medium, so that the final composition differs substantially from any composition found in nature.

The invention also encompasses vectors which contain nucleic acid sequences encoding the polypeptides of the invention. Those of skill in the art are familiar with the many types of vectors which are available, including but not limited to, for example: plasmids, cosmids, various expression vectors, viral vectors, etc. These vectors may be used, for example, during genetic manipulation of the sequences, and/or to transform or transfect a host so as to introduce a sequence of interest into the host. In addition, the vector themselves may be made available for sale.

Exemplary amino acid primary sequences of the enzymes and exemplary nucleotide sequences which encode them are described herein. However, one of skill in the art will recognize that the sequences that are used in the practice of the invention need not conform precisely to these sequences. Rather, variants and derivatives of the sequences may be use, so long as the variant/derivative has the desired level of enzyme activity to carry out the function or activity described herein. Exemplary acceptable modifications of the sequences include but are not limited to: for the nucleic acids, due to the redundancy of the genetic code, different triplet codons may be utilized to encode the same amino acid, e.g. to optimize the codon for transcription and translation by a particular host organism; or to introduce or add convenient restriction enzyme cleavage sites (e.g. to facilitate cloning), etc. In general, the resulting variant nucleotide sequence is at least about 75, 80, 85, 90, 95, 96, 97, 98, or 99% homologous to the parent (native) sequence, or at least to the segment of the native sequence that encodes the enzyme of interest. In some aspects, described below, the identity of an amino acid may also be changed. Those of skill in the art will recognize that when the gene sequences are cloned, various other nucleotide sequences may be associated with, usually adjacent to, the 5' or 3' end of the gene, as appropriate, e.g. a transcriptional control region comprising a promoter, a translational initiation signal, a signal for peptide secretion, various enhancer sequences, various poly A and transcription termination signals, etc. While the nucleotide sequences of the genes are provided herein, the invention also encompasses other types of nucleic acids which encode the sequences of interest, e.g. cDNA, mRNA, etc. corresponding to (e.g. complementary to) the sequences.

Exemplary amino acid sequences of the enzymes are presented herein. However, one of skill in the art will recognize that certain changes to the sequences may be made without being detrimental to the practice of the invention. For example, conservative amino acid substitutions that are well-known in the art may be made. Various insertions and deletions (e.g. especially deletions from the amino and/or carboxyl termini of from about 1-10 or more amino acids) may be made and variants generated in this manner are also encompassed by the invention, so long as they retain at least about 50, 60, 70, 80, 90 or 100% or more of the activity of the parent molecule. In other words, enzymatically active fragments or segments of the enzymes are also encompassed. The variant may be more active than the parent molecule. The sequences may also be modified, e.g. to remove or introduce protease digestion sites, to increase or decrease solubility, to include a leader sequence, to include a detectable label or a sequence that is useful for capturing and purifying the enzyme (e.g. His tags, glutathione-S transferase tags, etc.), or for any other suitable reason. The resulting variant amino acid sequence is generally at least about 75, 80, 85, 90, 95, 96, 97, 98, or 99% identical to the parent (native) sequence, e.g. to the portion of the native sequence that represents the enzyme per se. In addition, the invention encompasses the use of corresponding enzymes from different strains or mutants of *A. nidulans* and/or *P. chrysosporium*, or from related fungi with suitable biomass degrading enzyme activities.

The amount of enzyme or effective enzyme activity in blends may vary depending on the particular enzymes that are combined, the desired usage, the activity level, etc. However, generally the amount of enzyme in a blend is in the range of from at least about 0.1 to about 1 unit of activity, e.g. from about 0.1, 0.2, 0.3, 0.4, 0.5, 0.6, 0.7, 0.8, 0.9 or 1.0 units of activity (or more if desired). Typically, about 0.3 to about 0.6 units are utilized. The blends are typically provided as concentrates and when added to a reaction mixture, are diluted to a final desired concentration. Generally from about 1 to about 1000 µl of a blend is used, e.g. about 10 to about 750 µl, or from about 50 to 500 µl, etc. Any suitable amount may be used to attain a desired rate or level of biomass digestion. For example, an exemplary enzyme blend is: 0.5 U xylanase+0.5 U cellobiohydrolase+0.5 U Feruloyl esterase+0.3 U LPMO, the enzymes being present in a ratio of 1:1:1:1.

The general procedures that can be used for generating fungal clones comprising the enzymes described herein are as follows: condia (spores) from the host fungus are germinated to afford young germling mycelia. Cell walls of the mycelia are removed (e.g. using a lytic enzyme) to form protoplasts, which are osmotically fragile. DNA encoding the gene to be transformed and usually encoding a selectable marker is mixed with $CaCl_2$ and polyethylene glycol (PEG) and the protoplasts are exposed to the mixture. The protoplasts are plated on osmotically stable media to regenerate (e.g. minimal media and 1.2M sucrose plus an agent that causes selection) and transformants which grow successfully are selected.

This disclosure describes the production of enzymes and/or enzyme blends that have applications in the cost-effective production of sugars and other breakdown products from biomass. The enzymes and enzyme systems may be used for the breakdown (catalysis) of cellulose in biomass from a wide variety of sources. Biomass comes in many different types, which may be grouped into four main categories: (1) wood residues (including sawmill and paper mill discards); (2) municipal paper waste; (3) agricultural residues (including corn stover, sugarcane bagasse and sorghum stover); and (4) dedicated energy crops, which are mostly composed of fast growing tall, woody grasses. Many types of hemicellulosic materials may be treated in accordance with this invention, including but not limited to lignocellulosic biomass such as agricultural residues (straws, hulls, stems, stalks), corn fiber, wood, municipal solid wastes (paper, cardboard, yard trash, and wood products), wastes from the pulp and paper industry, and herbaceous crops. Furthermore, the cellulose of many red algae contains a significant amount of mannose, e.g. the so-called α-cellulose from *Porphyra* is pure mannan. Exemplary sources include but are not limited to: plant biomass, e.g., corn, grains, grasses, woods, corn stover, sorghum stover, miscanthus, switchgrass, etc. Any type of lignan and cellulose-containing biomass from any source may be digested by the enzymes and mixtures thereof described herein.

The invention also provides methods of use of the enzymes disclosed herein. Such methods generally involve combining a blend as described herein with a suitable substrate (biomass) under conditions that allow, promote or result in catalysis of the substrate by the enzyme(s). Generally, the reaction will be carried out at a temperature in the range of from about 30 to about 50° C., and the length of time for a reaction will be in the range of from about one hour to about six days. Reactions are carried out in media such as aqueous media buffered to a suitable pH, e.g. in the range of from about pH 4 to about pH 9. Mixtures of biomass and two or more of the enzymes described herein are also encompassed by the invention.

Thereafter, the desired products (e.g. saccharides, bleached or treated pulp, etc.) may be harvested from the broth for various applications, or the reaction products may be further processed. For example, for the production of ethanol, fermentation of sugars produced by the digestion may be carried out by known conventional batch or continuous fermentation processes, usually using yeast. Ethanol may be recovered by known stripping or extractive distillation processes.

Such reactions may be carried out in order to obtain valuable breakdown products such as various fermentable sugars generated by hemicellulose catalysis. Alternatively, enzymes are also useful for various pretreatments of e.g. kraft pulp for other purposes such as for bleaching pulp that is used to make paper. In addition, a variety of non-pulp applications exist for the enzymes. For example, the enzymes may be useful as animal feeds additives; in clarifying juice and wine; for extracting coffee, plant oils and starch; for the production of food thickeners; for altering texture in bakery products (e.g., to improve the quality of dough, to help bread rise); for fruit and vegetable processing; for the processing of wheat and corn for starch production; as components of detergents and other cleaning compositions; in breaking down agricultural waste, in textile manufacture, etc.

The breakdown of biomass may or may not be complete, depending on the desired end products, and the precise activity of the enzyme or enzymes that are used to carry out the process. Any desired grouping of the enzymes of the invention may be utilized to generate any desired end product that the enzymes are capable of producing from a suitable substrate. In one embodiment of the invention, a "system" could further include a yeast or other organism capable of fermenting sugars produced by the enzymes, e.g. to produce ethanol or other valuable fermentation products, e.g. in the same media as that in which the digestion takes place.

Many useful products are produced by digesting biomass using the mixtures described herein and/or contain one or more of the enzymes described herein. The products include but are not limited to: sugars such as glucose, arabinose, xylose, mannose, galactose, etc.; paper products, animal feed, textiles, starch, detergents and other cleaning agents, bakery products, fruits and vegetables, juices, wine, ethanol, biofuel, etc. All such products made using the enzymes and enzyme combinations or containing the enzymes are encompassed by the present invention.

The sugars produced by the methods described herein can be used for a wide variety of applications and products. Exemplary applications/products include but are not limited to: detergents, the paper industry, the food industry, in animal feed, etc. In one aspect, the sugars are used for biofuel production. The invention thus provides a method of making biofuel, comprising digesting biomass with a blend to enzymes as described herein; obtaining glucose as a breakdown product of the digestion; fermenting glucose with a suitable organism (e.g. yeast) to produce ethanol.

U.S. Pat. No. 9,040,263 to Anton, et al. and U.S. Pat. No. 8,847,031 to Prade, et al. and US published patent applications 20150004670 to Mueller et al. and 20150147796 to Bonde describe various techniques for cloning organisms to treat biomass and the treatment of biomass to obtain one or more products of interest, such as biofuel. The complete contents of each of these are hereby incorporated by referenced in entirety.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

For purposes of the instant disclosure, the term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Still further, additional aspects of the instant invention may be found in one or more appendices attached hereto and/or filed herewith, the disclosures of which are incorporated herein by reference as if fully set out at this point.

EXAMPLES

This disclosure describes the discovery, molecular engineering, production and characterization of a comprehensive set of enzymes or enzyme blends isolated from two different lead fungi, *Aspergillus nidulans* and *Phanerochaete chrysosporium* that are capable of breaking down celluloses, hemicelluloses and pectin into simple sugars. *A. nidulans* is a producer of hemicellulases, cellulases, and pectinases whereas *P. chrysosporium* produces a suit of enzymes for degradation of hemicellulose, cellulose, and lignin. A blend of enzymes from these two fungi breaks down the complex matrix of untreated sorghum cell walls rather than needing pretreatment for efficient hydrolysis of the biomass. The enzyme blends comprise two or more enzymes from the same fungus or two different fungi, *P. chrysosporium* and *A. nidulans*, for efficient and cost effective methods of complete degradation of lignocelluloses Methods to characterize the performance of the enzymes and their variants based on their hemicellulase, cellulase and pectinase activity have also been developed. Successful cloning and production of enzymes for e.g endopolygalacturonases, glucoronyl esterases and cellobiohydrolases have been carried out in an expression system developed for that purpose. The cloned enzymes showed high enzymatic activities when measured by enzyme assays and capillary zone electrophoresis. This successful cloning and production of enzymes with high enzyme activities permits the production of large quantities of enzymes and enzyme cocktails for commercial applications.

Example 1

A total of 98 polypeptides/nucleic acid sequences from *Aspergillus nidulans* and 125 polypeptides/nucleic acid sequences from *Phanerochaete chrysosporium*, were identified. The enzymes include cellulases, hemicellulases, pectinases, carbohydrate esterases, chitinases, other classes of polypeptides having cell wall modifying activity, and many proteins of unknown function associated with hydrolysis of lignocelluloses. This significant and comprehensive set of enzymes with their physical properties are shown in Tables 1-6.

The performance of the enzymes based on their hemicellulase, cellulase and pectinase activity was determined. Importantly, recently we achieved successful cloning and production of few of these enzymes for e.g endopolygalacturonases, glucoronyl esterases and cellobiohydrolases in the expression system developed in our lab by using their nucleic acid sequences. Above mentioned cloned enzymes showed high enzymatic activities when measured by enzyme assays and capillary zone electrophoresis (unpublished data). This successful cloning and production of enzymes in our lab with high enzyme activities will allow us to produce large quantities of enzymes or enzyme cocktails for commercial applications in future.

The activities of enzymes from *A. nidulans* and *P. chrysosporium* secreted in crude cell extract were compared to commercial enzyme preparation (containing 20-30% cellulases by weight and less than 5% of xylanases by weight) on sorghum stover. The simple sugars released from sorghum stover after treatment were measured at different time points. Enzymes from *A. nidulans* released 142 mg/g of dry biomass after 48 hours and enzymes from *P. chrysosporium* produced 196 mg/g of dry biomass on day 14, whereas treatment with the commercial enzyme preparation released only 125 mg/g of dry biomass after 48 hours.

Example 2. *Pichia pastoris* Clones

Recombinant *Pichia pastoris* clones expressing enzymes from *A. nidulans* and *P. chrysosporium* that are involved in the disentrapment of cellulose have been prepared, and used to degrade lignocellulose in untreated and hot water pretreated sorghum stover.

Example 3. Preparation and Testing of Exemplary Enzyme Blends

Media, Strains, Cultivation and Solutions.
*A. nidulans* was incubated at 37° C. Vegetative cultures and spore production were prepared by inoculation of conidia in minimal medium as described in Clutterbuck (Clutterbuck 1992) and Pontecorvo (Pontecorvo, Roper et al. 1953). 20× Clutterbuck salts (Clutterbuck 1992): 120 g of NaNO$_3$, 10.4 g of KCl, 10.4 g of MgSO$_4$.7H$_2$O and 30.4 g of KH$_2$PO4 in 1,000 ml. 1000× Vitamins: 10 mg of each vitamin in vitamin kit (Sigma Aldrich V-1) in 1,000 ml. 1000× Trace Elements: 2.2 g of ZnSO$_4$.7H$_2$O, 1.1 g of H$_3$BO$_3$, 0.5 g of MnCl$_2$.4H$_2$O, 0.5 g of FeSO$_4$.7H$_2$O, 0.16 g of CoCl$_2$.5H$_2$O, 0.16 g of CuSO$_4$.5H$_2$O, 0.11 g of Na$_2$MoO$_4$.4H$_2$O and 5 g of Na$_2$EDTA in 100 ml. *A. nidulans* strain A773 (pyrG89; wA3; pyroA4) was purchased from the Fungal Genetics Stock Center (FGSC, St Louis, Mo.) and media supplemented with pyridoxine (1 mg/L), uracil/uridine (2.5 mg/L each) or as needed.

5-fluorotic acid (5-FOA) was purchased from Oakwood Products Inc (NC9639762), zeocin (phleomycin) from Invitrogen (ant-zn-1) and all other chemicals from Sigma Aldrich, Megazyme and Fisher Scientific. pEXPYR plasmid was used throughout this work and its molecular features were reported elsewhere (Segato, Damasio et al. 2012).

Construction of pEXPYR-Client Protein Plasmids.
PCR-amplified gene-fragments were used as primers of genes. Amplicons were digested with NotI and XbaI, isolated by gel excision of a thin-slice from a 0.8% agarose electrophoresis gel, purified with QIAquick Gel Extraction kit (Quiagen), ligated onto NotI/XbaI digested pEXPYR plasmid with T4-fast ligase (Promega, Wis.) and transformed into Ca$^+$ competent *Escherichia coli* TOP 10F' cells (Invitrogen, CA). Random ampicillin-resistant colonies were selected and grown in 5 ml LB-ampicillin broth, plasmids purified (Sambrook, Fritsch et al. 1987), restricted with NotI/XbaI and insert size verified by 1% agarose gel electrophoresis (Sambrook, Fritsch et al. 1987). Plasmids with the correct insert size DNA were fully sequenced at the Oklahoma State University Core Facility and clones with the correct DNA sequence used for transformation.

DNA mediated transformation was based on the methods described for *A. awamori* and *A. nidulans* by Punt (Punt and van den Hondel 1992) and Yelton (Yelton, Hamer et al. 1984), respectively. DNA mediated transformation was done as follows; a young mycelium was grown overnight at 30° C. (*A. awamori*) or 37° C. (*A. nidulans*) 180 rpm in minimal medium with supplements, harvested by filtration (Whatman filter paper), washed with 0.6 M MgSO$_4$, suspended in 5 ml DSPS (1.1 M KCl, 0.1 M citric acid, pH 5.8) with 100 mg of lysing enzymes from *Trichoderma harzianum* (Sigma L1412), 100 mg of lysozyme from chicken egg white (Sigma L7651) and 100 mg of albumin bovine fraction V (Sigma A4503). The slurry was incubated at 30° C., 100 rpm for 1-2 hours and protoplasts harvested by filtration through a one layer Miracloth, washed by centrifugation 4,500 g, 4° C., 10 min, twice with 50 ml STC (1.2 M Sorbitol, 50 mM CaCl$_2$, 50 mM TRIS pH 7.5). The final pellet was suspended in 1 ml STC and stored at 4° C. until further use. In a falcon tube 10 mg of pEXPYR plasmid DNA was added onto 100 ul STC (final volume) along with additional 150 ul of protoplasts (~10$^8$), incubated at RT for 10-15 minutes prior to the addition of 1 ml of 60% PEG solution (60% PEG4000 in STC). The transforming mixture was mixed carefully by swirling and incubated at room temperature for 10-15 minutes, 8 ml of STC was added and 1 ml poured onto protoplast-recovery (1.2 M sorbitol) and transformant-selection (no uracil, uridine or 5-FOA) basic medium plates (medium without yeast extract or vitamins). Plates were incubated at 30° C. or 37° C. for one day and then inverted. Transformants were harvested during a two to three day period, plated and purified through a single spore condition cycle (Pontecorvo, Roper et al. 1953; Clutterbuck 1992). Recombinants were further selected by zeocin resistance (up to 500 ug/ml) and heritable genomic integration validated by PCR amplification of a hybrid pEXPYR-flank and client-insert DNA fragment. The enzymes that were cloned in this manner are listed in Table 13.

TABLE 13

Molecular engineered enzymes for making blends.

| SEQ ID NO: | GenInfo Identifier (GI) deposit number | Function | Name | Corresponding native enzyme from Tables 1-12 |
|---|---|---|---|---|
| 21 | GI: 67538194 | feruloyl esterase | FaeEZY | AN5267 |
| 22 | GI: 67525921 | cellulase | CelEZY | AN3418 |
| 23 | GI: 67900486 | cellobiose dehydrogenase | CdhEZY | AN7230 |
| 24 | GI: 67516425 | cellulose 1,4-beta-cellobiosidase | CbcEZY | AN0494 |
| 25 | GI: 259487165 | xylanase | XylEZY | AN1818 |
| 26 | GI: 67527724 | rhammnoglacturonan lyase | RhlEZY | AN4139 |
| 27 | GI: 67524141 | rhammnoglacturonan acetylesterase | RhaEZY | AN2528 |

TABLE 13-continued

Molecular engineered enzymes for making blends.

| SEQ ID NO: | GenInfo Identifier (GI) deposit number | Function | Name | Corresponding native enzyme from Tables 1-12 |
|---|---|---|---|---|
| 28 | GI: 67521656 | endoglucanase | EglEZY | AN1285 |
| 29 | GI: 67525801 | mannanase | ManEZY | AN3358 |
| 30 | GI: 67538224 | cellobiohydrolase | CbhEZY | AN5282 |
| 31 | GI: 67901108 | cutinase | CutEZY | AN7541 |
| 32 | GI: 67901108 | rhamnogalacturonase | RhgEZY | AN9134 |
| 33 | GI: 67522695 | glucosidase | GluEZY | AN1804 |
| 34 | GI: 67524223 | pectin lyase | PelEZY | AN2569 |
| 35 | GI: 74593086 | galactosidase | GalEZY | AN8138 |
| 36 | GI: 67902680 | polygalacturnoase | EpgEZY | AN8327 |
| 37 | GI: 67517718 | monooxygenase 1 | Pmo1EZY | AN1041 |
| 38 | GI: 67525177 | monooxygenase 2 | Pmo2EZY | AN3046 |
| 39 | GI: 67540516 | monooxygenase 3 | Pmo3EZY | AN6428 |
| 40 | GI: 75859132 | monooxygenase 4 | Pmo4EZY | AN9524 |

Production and Secretion of Client Proteins.

$10^7$-$10^8$ spores/ml were inoculated in liquid minimal medium supplemented with 0.5 to 15% of maltose, distributed onto dishes (10 ml in 60 mm, 20 ml in 150 mm Petri-dishes and 500 ml onto cafeteria trays) and incubated (stationary) at 37° C. (*A. nidulans*) or 30° C. (*A. awamori*) for 2-3 days. The mycelial mat was lifted with spatula and discarded and the medium collected by filtration, centrifuged at 10,000 g for 10 minutes prior to concentration by ultra-filtration (5,000 dalton cutoff, Amicon), quantified by the Bradford method (Marshall and Williams 1992), validated for purity by SDS PAGE (Shapiro, Vinuela et al. 1967) and used for biochemical studies.

Purification.

After growth, enzymes were concentrated 10× using a 10 kDa polyethersulfone ultrafiltration membrane and stored until purification. Enzymes were purified using a Ni-NTA column for or a DEAE anion exchange column.

Standard Enzyme Activity Assays.

Enzymatic activity on cellulosic, hemicellulosic substrates was determined by adding 10 ul of enzyme to 50 ul of 1% (wt/vol) substrate in 100 mM phosphate buffer, pH 6.0 (or as specified) and incubating with agitation at 45° C., or as specified for 30 to 60 minutes. The reaction was terminated by addition of 60 ul of dinitrosalicyclic acid (DNS) and incubated in a boiling (95° C.) water bath for 5 min. The enzymatic release of reducing sugars, which react with DNS was spectrophotometrically quantified at 575 nm with a Multimode Infinite M200 Reader (Tecan, S.C.) and compared with glucose and cellobiose standard curves. This method was partially based on the DNS method described by Miller (Miller 1959). Assays were carried out on sealed 96-well microtiter plates, or in 96-well-format assembled 8-strip 0.2 ml tubes, with attached hinged caps. All incubations were carried out in a Thermal Cycler (MJ Research) or under agitation in a rotating hybridization oven (Thermo Scientific). Specific activity was defined as U per mg protein at 45° C. whereas U is the amount of enzyme that produces one mmole of reducing sugar (glucose or cellobiose) per minute.

Blend Assembly.

After determining individual U/ml, appropriate amounts of selected enzymes were mixed together and an enzyme assay was carried out on an exemplary mixture or "cocktail" of enzymes, referred to as blend 1. The components of the blend were: enzymes LPMO (AN3046)+cellobiohydrolase (CBH) (AN0494). Enzyme activities were measured at 30 minutes, 2 hour and 24 hours, and blend activities were compared with individual respective enzyme activities. The quantitative determinations of the enzyme activities were carried out using the DNS method. Assay mixtures to calculate blend activities contained phosphoric acid swollen cellulose or carboxymethyl cellulose as the substrate and an appropriate aliquot of each selected concentrated enzymes in 50 mM buffer of optimal pH. The mixture was incubated 10-60 minutes at optimal temperature. The reaction was terminated after collection of the supernatant, the addition of DNS reagent, and heating for 5 minutes at 100° C. Enzyme activity was determined spectrophotometrically by measuring the release of reducing groups from respective polysaccharides. This reaction was then repeated with 20 mg of sorghum for the substrate and the supernatant was assayed for the final activity calculations. The remaining collected supernatant was then used for gas chromatography.

Gas Chromatography.

An appropriate amount of the collected supernatant was then used for menthanolysis to determine how the substrates (phosphoric acid swollen cellulose, CMC, and sorghum) were degraded by the blend. Twenty-five microliters of extracellular extracts were mixed with 100 nmol of inositol (internal standard) and dried. Two hundred microliters of 1.5 M HCl in methanol was added to each sample followed by 100 µl of methyl acetate and heated at 80° C. for a minimum of 3 h, which converted the sugars to methyl glycosides (Komalavilas and Mort 1989). The vials were cooled, followed by addition of a few drops of t-butanol followed by the evaporation of the solvents under a stream of nitrogen at room temperature. Twenty-five microliters of a 1:1:5 mixture of hexamethyldisilazane:trimethylchlrosilane:pyridine was added, and the samples were incubated for at least 15 min. The samples were evaporated under nitrogen gas and dissolved in 50 µl isooctane, out of which 1 µl was injected in the gas chromatograph (Agilent, Santa Clara, Calif., USA). The amount of each sugar in the sample was calculated by using the formula: area of sugar peak in sample/area of inositol peak in the sample/area of sugar peak in the standards/area of inositol in standards×100=number of nanomoles in the sample.

Figure 6:
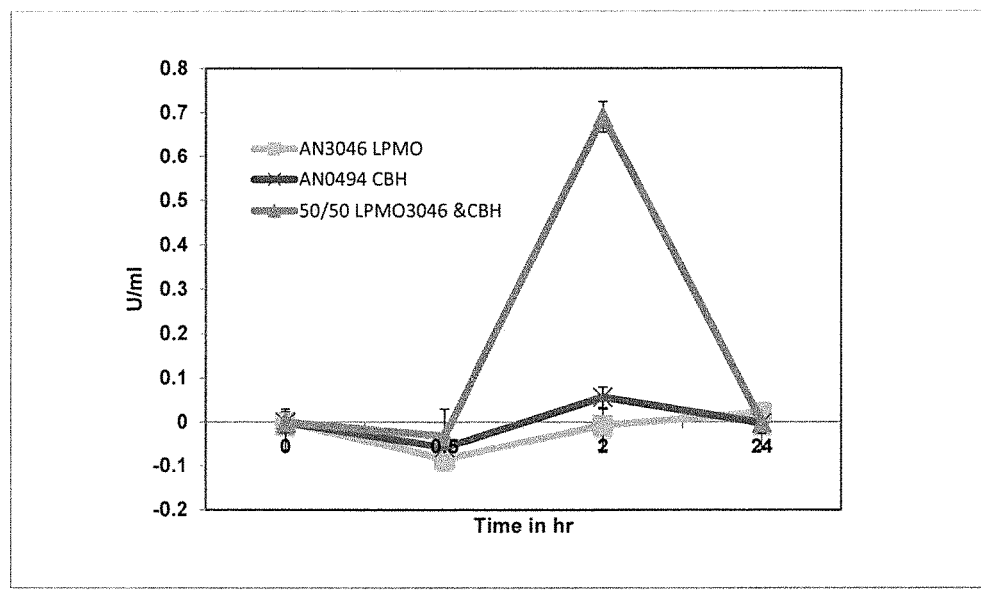
FIG. 6. Activity of blend 1. Lytic polysaccharide monooxygenase (LPMO) (3046)+cellobiohydrolase (CBH) (AN0494). Blend activities were compared with individual respective enzyme activities. A synergistic effect was observed in the blend compared to individual enzyme activities alone. Enzyme activities were measured at 30 minutes, 2 hour and 24 hours.

The results are presented in FIG. 6. As can be seen, a synergistic effect was observed in the exemplary blend as compared to individual enzyme activities alone.

REFERENCES

Clutterbuck, A. J. (1992). "Sexual and parasexual genetics of *Aspergillus* species." Biotechnology (Reading, Mass. 23: 3-18.

Marshall, T. and K. M. Williams (1992). "Coomassie blue protein dye-binding assays measure formation of an insoluble protein-dye complex." Anal Biochem 204(1): 107-109.

Miller, G. L. (1959). "Use of dintirosalicilic acid reagent for determination of reducing sugar." Analytical Chemistry 31: 426-428.

Pontecorvo, G., J. A. Roper, et al. (1953). "The genetics of *Aspergillus nidulans*." Advances in genetics 5: 141-238.

Punt, P. J. and C. A. van den Hondel (1992). "Transformation of filamentous fungi based on hygromycin B and phleomycin resistance markers." Methods Enzymol 216: 447-457.

Sambrook, J., E. F. Fritsch, et al. (1987). Molecular cloning: A laboratory manual, Cold Spring Harber.

Segato, F., A. R. Damasio, et al. (2012). "High-yield secretion of multiple client proteins in *Aspergillus*." Enzyme Microb Technol 51(2): 100-106.

Shapiro, A. L., E. Vinuela, et al. (1967). "Molecular weight estimation of polypeptide chains by electrophoresis in SDS-polyacrylamide gels." Biochem Biophys Res Commun 28(5): 815-820.

Yelton, M. M., J. E. Hamer, et al. (1984). "Transformation of *Aspergillus nidulans* by using a trpC plasmid." Proceedings of the National Academy of Sciences of the United States of America 81(5): 1470-1474.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. A composition for digesting lignocellulosic biomass that is or comprises at least one extracellular filtrate (ECF) that comprises at least two recombinant fungal glycosyl hydrolase enzymes: recombinant lytic polysaccharide monooxygenase (LPMO) 3046 and recombinant cellobiohydrolase (CBH) AN0494, wherein the amino acid sequence of the recombinant lytic polysaccharide monooxygenase (LPMO) 3046 is set forth in SEQ ID NO: 38 and amino acid sequence of the recombinant cellobiohydrolase (CBH) AN0494 is set forth in SEQ ID NO: 24.

2. The composition of claim 1, wherein the composition comprises a synthetic medium.

3. The composition of claim 2, wherein the synthetic medium comprises one or more of a nutrient, a stabilizing agent, a buffering agent or a salt.

* * * * *

SEQUENCE LISTING

```
<160> NUMBER OF SEQ ID NOS: 40

<210> SEQ ID NO 1
<211> LENGTH: 813
<212> TYPE: DNA
<213> ORGANISM: Artificial Sequence
<220> FEATURE:
<223> OTHER INFORMATION: Synthetic nucleic acid sequence encoding a
      feruloyl esterase

<400> SEQUENCE: 1
atgcttcgtg ctgttcttct tcctacactt cttgctttcg gcgctttcac acctgttcat      60
ggcgctaact ctcctggctg cggcaaacaa cctacactta caaacggcgt taaccaaatc     120
aacggccgtg aatacgttct taaaatccct gatggctacg atccttctaa acctcatcat     180
cttatcttcg gccttcattg gcgtggcggc aacatgtaca acgttgttaa cggcgattct     240
atccaacctt ggtacggcct tgaagctcgt gctcaaggct ctgctatctt cgttgctcct     300
aacggcctta acgctggctg ggctaacaca aacggcgaag atgttgcttt catcgatgct     360
atcatggaac aagttgaaga tgatctttgc gttgatcaag cttctcgttt cgctacaggc     420
ttctcttggg gcggcggcat gtcttacgct cttgcttgcg ctcgtgctgc tgaattccgt     480
gctgtttctg ttctttctgg cggccttatc tctggctgcg atggcggcaa cgatcctatc     540
gcttaccttg gcatccatgg catcaacgat cctgttcttc ctcttgatgg cggcgttaca     600
cttgctaaca cattcgtttc taacaacggc tgccaaccta cagatatcgg ccaacctgct     660
tctggctctg gcggctctgt tcgtacagat ttctctggct gctctcatcc tgtttctttc     720
atcgcttacg atggcggcca tgatggcgct cctcttggcg ttggctcttc tcttgctcct     780
gatgctacat gggaattctt catggctgct tga                                  813

<210> SEQ ID NO 2
<211> LENGTH: 1290
<212> TYPE: DNA
<213> ORGANISM: Artificial Sequence
<220> FEATURE:
<223> OTHER INFORMATION: Synthetic nucleic acid sequence encoding a
      cellulase

<400> SEQUENCE: 2
atggctcttc ttctttctct ttctcttctt gctacaacaa tctctgctca acaaatcggc      60
acacctgaaa tccgtcctcg tcttacaaca taccattgca catctgctaa cggctgcaca     120
gaacaaaaca catctgttgt tcttgatgct gctacacatc ctatccatga tgcttctaac     180
ccttctgttt cttgcacaac atctaacggc cttaaccctc tctttgccc tgataaacaa     240 acatgcgctg ataactgcgt tatcgatggc atcacagatt acgctgctca tggcgttgaa     300
acacatggct ctcgtcttac acttacacaa taccgtaacg ttaacggcgc tctttctttct     360 gtttctcctc gtgtttacct tgttgatgaa tctgatcctg atgaacaaga ataccgtgct     420
```

```
ctttctcttc ttgctcaaga attcacattc acagttaacg tttctgctct tccttgcggc      480
atgaacggcg ctctttacct ttctgaaatg tctccttctg gcggccgttc tgctcttaac      540
cctgctggcg cttcttacgg cacaggctac tgcgatgctc aatgctacgt taacccttgg      600
atcaacggcg aaggcaacat caacggctac ggcgcttgct gcaacgaaat ggatatctgg      660
gaagctaact ctcgttctac aggcttcaca cctcatgctt gcctttacga acctgaagaa      720
acagaaggcc gtggcgttta cgaatgcgct tctgaagatg aatgcgattc tgctggcgaa      780
aacgatggca tctgcgataa atggggctgc ggcttcaacc cttacgctct tggcaacaca      840
gaatactacg gccgtggcca aggcttcgaa gttgatacaa agaacccttt cacagttgtt      900
acacaattcc ttacagatga tggcacatct acaggcgctc ttacagaaat ccgtcgtctt      960
tacatccaaa acggccaagt tatcgaaaac gctgttgttt cttctggcgc tgattctctt     1020
acagattctc tttgcgcttc tacagcttct tggttcgatt cttacggcgg catggaaggc     1080
atgggccgtg ctcttggccg tggcatggtt cttgctatgt ctatctggaa cgatgctggc     1140
ggctacatgc aatggcttga tggcggcgat gctggcccct gcaacgctac agaaggcgct     1200
cctgaattca tcgaagaaca tacaccttgg acacgtgttg ttttcgaaga tcttaaatgg     1260
ggcgatatcg gctctacatt ccaagcttga                                       1290
```

<210> SEQ ID NO 3
<211> LENGTH: 2343
<212> TYPE: DNA
<213> ORGANISM: Artificial Sequence
<220> FEATURE:
<223> OTHER INFORMATION: Synthetic nucleic acid sequence encoding a
      cellobiose dehydrogenase

<400> SEQUENCE: 3

```
atgcattctt tccttcgttc tttcgctgct cttgttgctg ctggctctga tcctgataca       60
ggcatcgttt tcgatacatg gacagttgaa gcttcttctt cttctgctgg cttcacattc      120
ggcgtttctc ttcctgaaga tgctcttgat acagatgcta cagaattcat cggctacctt      180
tcttgctctt cttcttctac atctgaattc acaggctggt gcggcctttc tatgggctct      240
tctatgaact ctaaccttct tcttgttgct tacgctcaag atgatacagt tcttacatct      300
ttccgtttct cttctggcta cgctatgcct tctgtttact ctggcaacgc tacacttaca      360
caaatctctt ctacagttac agctgataaa ttcgaagttc ttttccgttg cgaagaatgc      420
cttcgttggg atcatgaagg cgtttctggc tctgctacaa catctgctgg ccaacttatc      480
cttgcttggg ctcaagctga agaatctcct acaaacgctg attgccctga tgatctttct      540
cttgttcaac atgaagctca aggcatctgg gttggcaaac tttctggcga tgctgctaca      600
tctaactacg aaacatgggc tgctcttgct acaaacgttg ttgatggcac atgcggcaca      660
gatggcggcg cggcggcgga taacggcaac ggcacaacac ctggcgttcc tgttcctaca      720
aacgttacat acgattacat catcgttggc tctggccctg ctggcatggt tcttgctgat      780
cgtctttctg aagctggcgc taaaacactt cttatcgaaa aaggccctcc ttctatcggc      840
ctttggaacg gcacaatgaa acctgattgg cttaacggca cagatcttac acgtttcgat      900
gttcctggcc tttgcaacga aatctggaaa aactctgatg gcatcgcttg ccctgataac      960
gatcaaatgg ctggctgcct tgttggcggc ggcacagctg ttaactctgg cctttggtgg     1020
aaaccttact ctaaagattt cgatgaatct ttccctgaaa catggaaata cgatgatgtt     1080
cgtgatgctg ttacacgtgt tttcacacgt atccctggca caacaacacc ttctacagat     1140
```

```
aaccgtctttt accttgctga aggcccttct gttatcatga acggccttct tgcttctggc    1200
tggaaaggca caacattcaa cgatgaacct gaagaaaaat acaaatctgt tggctactct    1260
ccttacatgt tctctcatgg ccaacgtaac ggccctatgg ctacatacct tcttgatgct    1320
taccaacgtc ctaacttcga tctttgggtt aacacagttg ttcgtcgtgt tgttcgtgat    1380
ggcgctacag ttacaggcgt tgaagttgaa cctttcaacg atggcggcta cgaaggctct    1440
cttcaactta acgaaggcgg ccgtgttatc ctttctgctg cgctttcgg cacacctaaa    1500 atccttttcc gttctggcat cggccctgaa gatcaacttg ctatcgttaa cggctctgct    1560
tctgatggcg aaacaatgat ctctgaagat caatggatca accttcctgt tggcgaaaac    1620
cttatggatc atcctaacac agaaatcgtt gttcaacatc ctgatgttgt tttctacgat    1680
tactacgctg cttacgatga tcctatcgaa gctgatgctc aatcttacct tgttaaccgt    1740
acaggccctc ttgctcaatc tgctcctaac gttaaccctg ttttcttcga tcaagttaca    1800
ggctctgata cgttacacg tcaacttcaa taccaagctc gtgttgaagg ctctcataac    1860
gttgctgatg ccatacaat ctctatctct caatacgttg gccgtggcca acatctcgt     1920 ggcaaactta caatcacatc tgctcttaac acagttgttt ctacacttcc ttggcttcaa    1980
gatgataacg atacagatgc tgttatcgct ggccttgaac gtcttcgtga ttctctttct    2040
acaatccaag gccttacatg ggcttaccct aaagctaacg tttctatggc tgaacatgtt    2100
aactctatgg ctaaaacagg ccgtggctct aaccattgga tgggctcttg caaaatgggc    2160
cctgatgatg gccgtgatgg cggctcttct gttgttgatc ttaacacaaa agtttacggc    2220
atggataacc ttttcgttgt tgatgcttct atcttccctg gcatgatctc tacaaaccct    2280
tctgcttaca tcacagttgt tgctgaacgt gctgctgaac gtatccttgc tcttcaaggc    2340
tga                                                                  2343
```

<210> SEQ ID NO 4
<211> LENGTH: 1593
<212> TYPE: DNA
<213> ORGANISM: Artificial Sequence
<220> FEATURE:
<223> OTHER INFORMATION: Synthetic nucleic acid sequence encoding a cellobiose dehydrogenase

<400> SEQUENCE: 4

```
atggcttctt ctttccaact ttacaaagct cttctttttct tctcttctct tctttctgct    60
gttcaagctc aaaaagttgg cacacaacaa gctgaagttc atcctggcct acatggcaa     120 acatgcacat cttctggctc ttgcacaaca gttaacggcg aagttacaat cgatgctaac    180
tggcgttggc ttcatacagt taacggctac acaaactgct acacaggcaa cgaatgggat    240
acatctatct gcacatctaa cgaagtttgc gctgaacaat gcgctgttga tggcgctaac    300
tacgcttcta catacggcat cacaacatct ggctcttctc ttcgtcttaa cttcgttaca    360
caatctcaac aaaaaaacat cggctctcgt gtttaccttta tggatgatga agatacatac    420
acaatgttct accttcttaa caaagaattc acattcgatg ttgatgtttc tgaacttcct    480
tgcggcctta acggcgctgt ttacttcgtt tctatggatg ctgatggcgg caaatctcgt    540
tacgctacaa acgaagctgg cgctaaatac ggcacaggct actgcgattc tcaatgccct    600
cgtgatctta aattcatcaa cggcgttgct aacgttgaag ctgggaatc ttctgataca    660 aacccctaacg cgcgcgttgg caaccatggc tcttgctgcg ctgaaatgga tatctgggaa    720
gctaactcta tctctacagc tttcacacct catccttgcg atacacctgg ccaaacactt    780
```

```
tgcacaggcg attcttgcgg cggcacatac tctaacgatc gttacggcgg cacatgcgat    840
cctgatggct gcgatttcaa ctcttaccgt caaggcaaca aaacattcta cggccctggc    900
cttacagttg atacaaactc tcctgttaca gttgttacac aattccttac agatgataac    960
acagatacag gcacactttc tgaaatcaaa cgtttctacg ttcaaaacgg cgttgttatc   1020
cctaactctg aatctacata ccctgctaac cctggcaact ctatcacaac agaattctgc   1080
gaatctcaaa agaacttttt cggcgatgtt gatgttttct ctgctcatgg cggcatggct   1140
ggcatgggcg ctgctcttga caaggcatg gttcttgttc tttctctttg ggatgataac   1200
tactctaaca tgctttggct tgattctaac taccctacag atgctgatcc tacacaacct   1260
ggcatcgctc gtggcacatg ccctacagat tctggcgttc cttctgaagt tgaagctcaa   1320
taccctaacg cttacgttgt ttactctaac atcaaattcg ccctatcgg ctctacattc    1380 ggcaacggcg gcggctctgg ccctacaaca acagttacaa catctacagc tacatctaca   1440
acatcttctg ctacatctac agctacaggc caagctcaac attgggaaca atgcggcggc   1500
aacggctgga caggccctac agtttgcgct tctccttggg cttgcacagt tgttaactct   1560
tggtactctc aatgccttct tgaagatggc tga                                1593
```

<210> SEQ ID NO 5
<211> LENGTH: 928
<212> TYPE: DNA
<213> ORGANISM: Artificial Sequence
<220> FEATURE:
<223> OTHER INFORMATION: Synthetic nucleic acid sequence encoding a
      xylanase <400> SEQUENCE: 5

```
atggttcatc ttaaaacact tgctggctct gctgttttcg cttctcttgc tacagctgct     60
gttcttcctc gtcaatctgc ttctcttaac gatcttttcg ttgctgctgg caaatcttac    120
ttcggcacat gctctgatca agctcttctt caaaactctc aaaacgaagc tatcgttgct    180
tctcaattcg gcgttatcac acctgaaaac tctatgaaat gggatgctct tgaaccttct    240
caaggcaact cggctggtct ggcgctgatt accttgttga ttacgctaca acacataaca    300
aaaaagttcg tggccataca cttgtttggc attctcaact tccttcttgg gtttcttcta    360
tcggcgatgc taacacactt cgttctgtta tgacaaacca tatcaacgaa gttgttggcc    420
gttacaaagg caaaatcatg cattgggagt tgttaacgaa atcttcaacg aagatggcac    480
attccgtaac tctgttttct acaaccttct tggcgaagat tcgttcgta tcgctttcga    540 aacagctcgt gctgctgatc ctgatgctaa actttacatc aacgattaca accttgattc    600
tgcttcttac gctaaaacac aagctatggc ttcttacgtt aaaaaatggc ttgctgaagg    660
cgttcctatc gatggcatcg ctcttttctc tcttgctaac acaggcgttt ctgaagttgc    720
tatcacagaa cttgatatcg ctggcgctgc ttcttctgat tacccttaacc ttcttaacgc    780 ttgccttaac gaacaaaaat gcgttggcat cacagtttgg ggcgtttctg ataaagattc    840
ttggcgtgct tctgattctc ctcttctttt cgatggcaac taccaaccta agatgcttta    900
caacgctatc gttaacgctc tttcttga                                       928
```

<210> SEQ ID NO 6
<211> LENGTH: 2987
<212> TYPE: DNA
<213> ORGANISM: Artificial Sequence
<220> FEATURE:
<223> OTHER INFORMATION: Synthetic nucleic acid sequence encoding a rhammnoglacturonan lyase

<400> SEQUENCE: 6

```
atgttcgctt ctacacttcg taaaacattc gttttccttg gccttgctac atactctgct      60
gctgctctta caacaacatc taactctaca cattacacaa tctctaactc tcgtttctct     120
gttgctgttg ctaaatctat aacggcacag attctacagg cacaccttac gttggcgtta     180
tcatgacaga tacatacgaa acaacaaacc aaacactttc tcaataccct tccttcgtg      240
gcgaagaaac aggccttcat gctttctctc gtgttacata ctacaacgaa tctgattact     300
tccttcgtgg ccttggcgaa cttcgtacac ttttccgtcc taacacaaac ctttggacac     360
atttctctgg ctctgaaggc aactacggcc ctatgcctct ttcttctaca gaaaaaatca     420
cagttcaaga tgctacaaca taccttggcg atacaacaga tgatccttac gttttctcaat    480
actctgatta cttcacaaaa tacacactta cagaatcttg gcgtgatcat gatgttcatg     540
gccatttctc taacggctct acatctggcg atggcaacac atacggcgct tggcttgttc     600
ataacacacg tgaaacatac tacggcggcc ctcttcatgc tgatcttgtt gttgatggca     660
tcgtttacaa ctcatcgtt tctggccatt acggcgctcc taaccctaac cttacacatg      720
gcttcgatcg tacattcggc cctcaatact accatttcaa ctctggcggc cctggcacaa     780
cacttgaaga acttcgtgct gatgctgctc aatacgcttc tcctgaatgg aacgctgaat     840
ctacgattc tatcgctaaa catatccta actacgttcc ttctacaggc cgtacaacat       900
tccgtggcaa agttaacctt cctaaaggcg ctaaaaaacc tatcatcgtt ctttctgaaa     960
acgaacaaga tttccaactt aacgttttca aaaaagattc tcttcaatac tgggctgaaa    1020
tcgatggctc tggcgctttc acaatccctc gtgttgttaa aggcacatac cgtgttacaa    1080
tctacgctga tgaaatcttc ggctggttca tcaaagataa cgttaaagtt atcggctcta    1140
acgctcatac attcacatgg aaagaagaaa cagctggcaa agaaatctgg cgtatcggcg    1200
ttcctgataa atcttctggc gaattccttc atggctacgc tcctgataca tctaaacctc    1260
ttcaacctga caataccgt atctactggg gcaaatacga ttacccttct gatttccctg     1320
aaggcgttaa ctaccatgtt ggcaaatctg atcctgctaa agatcttaac tacatccatt    1380
ggtctttctt cccttctcaa ggcaaccatc ttcgtaacga accttactac caaaacgtta    1440
caaactggac aatcacattc gatcttacag cttctcaact tcgtaacaca aaaacagcta    1500
cattcacagt tcaacttgct ggcacacgta acgctaacgg caactctaaa tggaaccctg    1560
atcctgctaa atcaacaac cttccttgga cagttaacgt taacggcatc tacgaagata    1620
catgggaaat cccttactgg cgttctggct cttgcggcgt tcgttctggc gttcaatgcc    1680
aaaacacaga acataaattc gttttcgatg ctggcaaact tcgtaaaggc cgtaacgaat    1740
tcgttctttc tcttcctttc aacgctacat ctgttgaaac agctcttctt cctaactctc    1800
tttacgttca agttgtttct atggaagctg tttctgtttc taacgatatg cgtgttcttg    1860
ttcaagcttt catgcctctt gttacatggg gcacagctgt tgaaaacgt gttcttctta     1920
caggcatcgt ttctgtttct gctatggcta agaagatta ccctatgatc tctcgtcctt    1980
gccctcgtaa aggcggcaca cgtcgtcgta aaaaagaacg taaaaaagaa ggcaaaaaac    2040
aaggccgtac agttcttgat gctcttcttc aacgttctga acaagattct ttctggtctc    2100
gtttctgccg ttctcctatc gaatctgttg ctcaatacgt ttacggccaa ggctctacag    2160
ctcttcgtaa aaaacaaca gataaaccttg ttcgtgttgt ttgcgtttct gatacacata    2220
acacaaaacc taaccttcct gatggcgata tccttatcca tgctggcgat cttacagaat    2280
```

| | |
|---|---|
| ctggcacaaa agaagaactt gaaaaacaaa tctactggct tgattctcaa cctcatcgtt | 2340 |
| acaaaatcgt tatcgctggc aaccatgaaa cattccttga tcgtaactac cattctcatc | 2400 |
| atggcaacga acgtgttaca atggattgga atctcttat ctaccttgaa aacacatctg | 2460 |
| ctatccttga tcttggcgct ggccatcaac ttaaagtttt cggctctcct tacacaccta | 2520 |
| aacatggcaa cggcgctttc aatacccctc gtacagatac aacaacatgg aagaaatcc | 2580 |
| ctaaagatac agatcttctt gttacacatg gccctcctaa agctcatctt gatcttggcc | 2640 |
| atcttggctg ccgtgttctt cgtcaagctc tttgggaaat ggaatctcgt cctcttcttc | 2700 |
| atgttttcgg ccatatccat ggcggctacg gcaaagaagt gtttgctgg gatctttgcc | 2760 |
| aacgtgctta cgaagctatc atggatggcg aatctcgttg gtggaacctt tgcgttcttt | 2820 |
| tctactgctg gatccttcgt cttttcttcg attggacagc tgatggccgt gctacagttc | 2880 |
| ttgttaacgc tgctacagtt ggcggcgttc gtgatcttaa acgtcgtgaa gctatctgcg | 2940 |
| ttgatatcca agctggctct aaacgtttcc tttctggctg cacatga | 2987 |

<210> SEQ ID NO 7
<211> LENGTH: 738
<212> TYPE: DNA
<213> ORGANISM: Artificial Sequence
<220> FEATURE:
<223> OTHER INFORMATION: Synthetic nucleic acid sequence encoding a
      rhammnoglacturonan acetylesterase

<400> SEQUENCE: 7

| | |
|---|---|
| atgaaatcta tcgctcttac atctctttct cttcttcctt ctgctcttgc tcaaacaatc | 60 |
| taccttgctg gcgattctac aatggcttct tctacacctg gctggggcga ttacatcgct | 120 |
| gattctgttt ctgttgaaat ctctaaccaa gctatcggcg ccgttctgc tcgttcttac | 180 |
| acacgtgaag gccgtttcca agctatcgct gatgttcttc aagctggcga ttacgttgtt | 240 |
| atcgaattcg gccataacga tggcggctct cttttctaacg ataacggccg tacagattgc | 300 |
| cctggcgatg gcgatgaaac atgcgaaaca gtttacaacg gcgttgctga aacagttctt | 360 |
| acattccctg cttacatcga aaacgctgct cttcttttcc ttgaaaaagg cgctaacgtt | 420 |
| cttatctctt ctcaaacacc taacaaccct tgggaatctg gcacattctc ttacacacct | 480 |
| aaccgtttcg ttggctacgc tgaacttgct gctcaacgtg ctggcgttga ttacgttgat | 540 |
| catggcgctt acacagcttc tatcttcgaa gctcttggcg ctgatacagt taactctttc | 600 |
| tacccctaacg atcatacaca tacaaacgct gaaggctctt ctgttgttgc tgatgctttc | 660 |
| cttaaagctg ttgtttgctc tggcgttgct cttaacgatg ttcttacacg tacagatttc | 720 |
| gatggcgaat gcctttga | 738 |

<210> SEQ ID NO 8
<211> LENGTH: 981
<212> TYPE: DNA
<213> ORGANISM: Artificial Sequence
<220> FEATURE:
<223> OTHER INFORMATION: Synthetic nucleic acid sequence encoding a
      endoglucanase

<400> SEQUENCE: 8

| | |
|---|---|
| atgcgttctc ttgttcttct ttcttctgtt cttgctcttg ttgctccttc taaaggcgct | 60 |
| ttcacatggc ttggcacaaa cgaagctggc gctgaattcg gcgaaggctc ttaccctggc | 120 |
| gaacttggca cagaatacat ctggcctgat cttggcacaa tcggcacact tcgtaacgaa | 180 |

| | |
|---|---:|
| ggcatgaaca tcttccgtgt tgctttctct atggaacgtc ttgttcctga ttctcttgct | 240 |
| ggccctgttg ctgatgaata cttccaagat cttgttgaaa cagttaacgg catcacagct | 300 |
| cttggcgctt acgctgttct tgatcctcat aactacggcc gttactacgg caacatcatc | 360 |
| acatctacag atgatttcgc tgcttttctgg acaatccttg ctacagaatt cgcttctaac | 420 |
| gaacttgtta tcttcgatac aaacaacgaa taccatacaa tggatcaatc tcttgttctt | 480 |
| aaccttaacc aagctgctat cgatgctatc cgtgcttctg cgctacatc tcaatacatc | 540 |
| ttcgctgaag gcaactcttg gacaggcgct tggacatggg ttgatgttaa cgataacatg | 600 |
| aaagctctta cagatcctca agataaactt atctacgaaa tgcatcaata ccttgattct | 660 |
| gatggctctg gcacaaacac agcttgcgtt tcttctacaa tcggctctga acgtgttaca | 720 |
| gctgctacaa actggcttcg tgaaaacggc aaacttggcg ttcttggcga attcgctggc | 780 |
| gctaacaacc aagtttgcaa agatgctgtt gctgatcttc ttgaataccct tgaagaaaac | 840 |
| tctgatgttt ggcttggcgc tctttggtgg gctgctggcc cttggtgggg cgattacatg | 900 |
| ttcaacatgg aacctacatc tggcatcgct taccaagaat actctgaaat ccttcaacct | 960 |
| tacttcgttg gctctcaatg a | 981 |

<210> SEQ ID NO 9
<211> LENGTH: 1152
<212> TYPE: DNA
<213> ORGANISM: Artificial Sequence
<220> FEATURE:
<223> OTHER INFORMATION: Synthetic nucleic acid sequence encoding a mannanase

<400> SEQUENCE: 9

| | |
|---|---:|
| atgaaattct ctcaagctct tctttctctt gcttctcttg cttgctgc tgctcttcct | 60 |
| catgcttcta cacctgttta cacaccttct acaacacctt ctcctacacc tacaccttct | 120 |
| gcttctggct ctttcgctac aacatctggc atccaattcg ttatcgatgg cgaagctggc | 180 |
| tacttccctg gctctaacgc ttactggatc ggcttcctta aaaacaactc tgatgttgat | 240 |
| cttgttttcg atcatatggc ttcttctggc cttcgtatcc ttcgtgtttg gggcttcaac | 300 |
| gatgttaaca cagctcctac agatggctct gtttacttcc aacttcatca agatggcaaa | 360 |
| tctacaatca cacaggcaa agatggcctt caacgtcttg attacgttgt tcattctgct | 420 |
| gaaaaacatg gcatcaaact tatcatcaac ttcgttaact actgggatga ttacggcggc | 480 |
| atgaacgctt acatgcgtgc ttacggcggc ggcgataaag ctgattggtt cgaaaacgaa | 540 |
| ggcatccaag ctgcttacca agcttacgtt gaagctgttg ttaaacgtta catcaactct | 600 |
| acagctgttt tcgctgggga acttgctaac gaacctcgtt gcacaggctg cgaaccttct | 660 |
| gttcttcata ctggatcga aaaacatctc gctttcatca aaggccttga tgaaaaacat | 720 |
| cttgtttgca tcggcgatgg ctctgatggc tcttaccctt tccaatacac agaaggctct | 780 |
| gatttcgctc tgctcttac aatcgataca atcgatttcg gcacattcca tctttaccct | 840 |
| gattcttggg gcacaaacaa cgattggggc aaactttgga tcacatctca tgctgctgct | 900 |
| tgcgctgctg ctggcaaacc ttgccttttc gaagaatacg gcgttacatc taaccattgc | 960 |
| gctatcgaaa acaatggca aaacgctgct cttaacgcta caggcatcgc tgctgatctt | 1020 |
| tactggcaat acggcgatac acttctttct ggcccttctc tgatgatgg caacacattc | 1080 |
| tactacggct ctgaagaatt cgaatgcctt gttacaaacc atgttgaaac aatcgaacgt | 1140 |
| tctgctaaat ga | 1152 |

<210> SEQ ID NO 10
<211> LENGTH: 1353
<212> TYPE: DNA
<213> ORGANISM: Artificial Sequence
<220> FEATURE:
<223> OTHER INFORMATION: Synthetic nucleic acid sequence encoding a cellobiohydrolase

<400> SEQUENCE: 10

| | | |
|---|---|---|
| atgcattact ctgcttctgg ccttgctctt gctttccttc ttcctgctat ccaagctcaa | 60 |
| caaacacttt acggccaatg cggcggctct ggctggacag cgctacatc ttgcgttgct | 120 |
| ggcgctgctt gctctacact taaccaatgg tacgctcaat gccttcctgc tgctacaaca | 180 |
| acatctacaa cacttacaac aacaacatct tctgttacaa caacatctaa ccctggctct | 240 |
| acaacaacaa catcttctgt tacagttaca gctacagctc tggcaacccc tttctctggc | 300 |
| taccaacttt acgttaaccc ttactactct tctgaagttc aatctatcgc tatcccttct | 360 |
| cttacaggca cactttcttc tcttgctcct gctgctacag ctgctgctaa aacacgtgat | 420 |
| gttgctgcta agttcctac aatggctaca taccttgctg atatccgttc tcaaaacgct | 480 |
| gctggcgcta accctcctat cgctggccaa ttcgttgttt acgatcttcc tgatcgtgat | 540 |
| tgcgctgctc ttgcttctaa cggcgaattc gctatctctg atggcggcgt tcaacattac | 600 |
| aaagattaca tcgattctat ccgtgaaatc cttgttgaat actctgatgt tcatgttatc | 660 |
| cttgttatcg aacctgattc tcttgctaac cttgttacaa accttaacgt tgctaaatgc | 720 |
| gctaacgctc aatctgctta ccttgaatgc acaaactacg ctgttacaca acttaaccct | 780 |
| cctaacgttg ctatgtacct tgatgctggc catgctggct ggcttggctg gcctgctaac | 840 |
| cttcaacctg ctgctaacct ttacgctggc gtttactctg atgctggctc tcctgctgct | 900 |
| cttcgtggcc ttgctacaaa cgttgctaac tacaacgctt gggctatcga tacatgccct | 960 |
| tcttacacac aaggcaactc tgtttgcgat gaaaaagatt acatcaacgc tcttgctcct | 1020 |
| cttcttcgtg ctcaaggctt cgatgctcat ttcatcacag atacaggccg taacggcaaa | 1080 |
| caacctacag ccaacaagc ttggggcgat tggtgcaacg ttatcggcac aggcttcggc | 1140 |
| gctcgtcctt ctacaaacac aggcgattct cttcttgatg ctttcgtttg ggttaaacct | 1200 |
| ggcggcgaat ctgatggcac atctgataca tctgctgctc gttacgatgc tcattgcggc | 1260 |
| tactctgatg ctcttcaacc tgctcctgaa gctggcacat ggttccaagc ttacttcgtt | 1320 |
| caacttcttc aaaacgctaa cccttctttc tga | 1353 |

<210> SEQ ID NO 11
<211> LENGTH: 774
<212> TYPE: DNA
<213> ORGANISM: Artificial Sequence
<220> FEATURE:
<223> OTHER INFORMATION: Synthetic nucleic acid sequence encoding a cutinase

<400> SEQUENCE: 11

| | | |
|---|---|---|
| atgcatttca acttcttttc tcttgctgct cttgctggcc tttctgttgc ttctcctctt | 60 |
| aaccttgatg aacgtcaaca tgctgttggc tcttcttctg caacgatct tcgtgatggc | 120 |
| gattgcaaac tgttacatt catcttcgct cgtgcttcta cagaacctgg ccttcttggc | 180 |
| atgtctacag gccctgctgt ttgcaacgat cttaaagctg atgcttctct tggcggcgtt | 240 |
| gcttgccaag gcgttggccc taaatacaca gctggccttg ctgaaaacgc tcttcctcaa | 300 |
| ggcacatctt ctgctgctat caacgaagct aaagaacttt tcgaacttgc tgcttctaaa | 360 |

```
tgccctgata cacgtatcgt tgctggcggc tactctcaag gcacagctgt tatgcatggc    420
gctatccctg atctttctga tgaaatcaaa gataaaatcg ctggcgttgt tcttttcggc    480
gatacacgta acaaacaaga tggcggccaa atcaaaaact ccctaaaga taaaatcaaa    540 atctactgcg ctacaggcga tcttgtttgc gatggcacac ttgttgttac agctgctcat    600
ttcacatacg ttgctaacac aggcgaagct tctaaatggc ttgaacaaca acttgcttct    660
atgcctgctt ctacatctac atcttcttct tcttcttctt cttcttctgc tcctgcttct    720
caaacatctc aatcttctgg cctttcttct tggttctctg gccttggcaa ctga          774
```

<210> SEQ ID NO 12
<211> LENGTH: 1553
<212> TYPE: DNA
<213> ORGANISM: Artificial Sequence
<220> FEATURE:
<223> OTHER INFORMATION: Synthetic nucleic acid sequence encoding a
      rhamnogalacturonase

<400> SEQUENCE: 12

```
atgtacgttt ctcgtcttct tcttttcctt gctcctcttc ttgttaaagg ccaactttct     60
ggctctgttg gccctcttac atctgtttct tctaaatctc aaacaaaaac atgcaacgtt    120
cttgattacg gcgctgttgc tgataaatct acagatatcg gccctgctct ttcttctgct    180
tgggatgaat gcgctgatgg cggcgttgtt tacatccctc tggcgatta cgctatcgaa    240 acatgggtta aactttctgg cggcaaagct tgcgctatcc aacttgatgg catcatctac    300
cgtacaggca cagatggcgg caacatgatc atgatcgaac atacatctga tttcgaattc    360
ttctcttcta catctaaagg cgcttttcca ggctacggct acgaattcca tgctaaaggc    420
tcttctgatg gccctcgtat ccttcgtctt tacgatgttt ctgatttctc tgttcatgat    480
gttgctcttg ttgattctcc tcttttccat ttctctatgg atacatgctc taacggcgaa    540
gtttacaaca tggctatccg tggcggcaac atgggcggcc ttgatggcat cgatgtttgg    600
tctacaaacg tttggatcca tgatgttatc catgctgaac attctccttt cgatgctcgt    660
tctgatcgtc ttcaatctcc ttctaaaaac atccttgttg aaaacatcta ctgcaactgg    720
tctggcggct gcgctatggg ctctcttggc acagatacag atatctctga tatcgtttac    780
cgtaacgttt acacatggaa atctaaccaa atgtacatgg ttaaatctaa cggcggctct    840
ggcacagttt ctaaccttgt tcttgaaaac ttcatcgctc gtgctgattc taaaggccat    900
ggcaacgctt actctcttga tatcgattct gcttggtctt ctatgtctac aatcgaaggc    960
gatggcgttg aacttaaaaa cgttacaatc cgtaactgga aaggcacaga agctgatggc   1020
tctcaacgtg gccctatcaa agttaaatgc gcttctggcg ctccttgcac agatgttaca   1080
gttgaagatt tcgctatgtg gacagaatct ggcgatgaac aaacatacgt tgcgaaaac   1140 gctttcggcg atggcttctg ccttgctgat ggcgatggca catctacatt cacaacaaca   1200
cttacagctt ctgctgctcc ttctggctac tctgctcctt ctatggatgc tgatcttgaa   1260
acagctttcg gcacagattc tgaaatccct atccctacaa tccctacatc tttctaccct   1320
ggcgctacac cttactctgc tcttgctggc gcttctgttt cttcttctca gttcctgctt   1380
gcttcttctt ctgctgaagc taaattcgtt gcttctcctg ctacatcttc tcctacagct   1440
acatctacag ctatctcttc tgttgatcct gtttctgctg ctacaacaac agctacatct   1500
catggccatg caaatctcat cataaacatc aatgccgtgc tcatcgtcat tga           1553
```

<210> SEQ ID NO 13
<211> LENGTH: 1855
<212> TYPE: DNA
<213> ORGANISM: Artificial Sequence
<220> FEATURE:
<223> OTHER INFORMATION: Synthetic nucleic acid sequence encoding a glucosidase

<400> SEQUENCE: 13

```
atgcgtgttg attctacagt tcttgctctt gttgctcttg ctacagattg ccttggcctt      60
gctatcaaat ctaacgaacc tgaacttctt cgtcgtgatg ctcttcctat ctacaaaaac     120
gcttcttact gcgttgatga acgtgttcgt gatcttcttt ctcgtatgac acttgaagaa     180
aaagctggcc aacttttcca taaacaactt tctgaaggcc ctcttgatga tgattcttct     240
ggcaactcta cagaaacaat gatcggcaaa aacatatga cacatttcaa ccttgcttct     300
gatatcacaa acgctacaca aacagctgaa ttcatcaacc ttatccaaaa acgtgctctt     360
caaacacgtc ttggcatccc tatcacaatc tctacagatc ctcgtcattc tttcacagaa     420
aacgttggca caggcttcca agctggcgtt ttctctcaat ggcctgaatc tcttggcctt     480
gctgctcttc gtgatcctca acttgttcgt gaattcgctg aagttgctcg tgaagaatac     540
cttgctgttg gcatccgtgc tgctcttcat cctcaagttg atctttctac agaacctcgt     600
tgggctcgta tctctggcac atggggcgaa aactctacac ttacatctga acttatcgtt     660
gaatacatca aaggcttcca aggcgaaggc aaacttggcc taaatctgt taaaacagtt     720
acaaaacatt tccctggcgg cggccctatg gaaaacggcg aagattctca tttctactac     780
ggcaaaaacc aaacatccct ggcaacaaca tcgatgaaca tcttatccct ttcaaagctg     840
ctcttgctgc tggcgctaca gaaatcatgc cttactactc tcgtcctatc ggcacaaact     900
gggaagctgt tggcttctct ttcaacaaag aaatcgttac agatcttctt cgtggcgaac     960
ttggcttcga tggcatcgtt cttacagatt ggggccttat cacagataca tacatcggca    1020
accaatacat gcctgctcgt gcttggggcg ttgaataccc tctgaacttc aacgtgctgc    1080
tcgtatcctt gatgctggct gcgatcaatt cggcggcgaa gaacgtcctg aacttatcgt    1140
tcaacttgtt cgtgaaggca caatctctga agatcgtatc gatgtttctg ttgctcgtct    1200
tcttaaagaa aaattccttc ttggcctttt cgataaccct ttcgttaacg cttctgctgc    1260
taacaacatc gttggcaacg aacatttcgt taaccttggc cgtgatgctc aacgtcgttc    1320
ttacacactt cttacaaaca accaaacaat ccttcctctt gctaaacctg gcgaaggcac    1380
acgtttctac atcgaaggct tcgattctgc tttcatgtct gctcgtaact acacagttgt    1440
taacacaaca gaagaagctg atttcgctct tcttcgttac aacgctcctt acgaacctcg    1500
taacggcaca ttcgaagcta acttccatgc tggctctctt gctttcaacg ctacagaaaa    1560
agctcgtcaa gctaaaatct actcttctct tcctacaatc gttgatatca tccttgatcg    1620
tcctgctgtt atccctgaag ttgttgaaca agctcaagct gttcttgctt cttacggctc    1680
tgattctgaa gctttccttg atgttgtttt cggcgtttct aaacctgaag caaacttcc    1740
tttcgatctt cctcgttcta tggatgctgt tgaagctcaa gctgaagatc ttcctttcga    1800
tacagaaaac cctgttttcc gttacggcca tggccttgaa tacgaagata actga         1855
```

<210> SEQ ID NO 14
<211> LENGTH: 1140
<212> TYPE: DNA
<213> ORGANISM: Artificial Sequence
<220> FEATURE:
<223> OTHER INFORMATION: Synthetic nucleic acid sequence encoding a pectin lyase

<400> SEQUENCE: 14

| | |
|---|---|
| atgcgtcttc atgctcctat cctttctctt cttgctgctg ctgcttctac atctgctgct | 60 |
| ggcgttacag gctctgctga aggcttcgct aaaggcgtta caggcggcgg ctctgctaca | 120 |
| cctgtttacc cttctacaac agctgaactt gtttcttacc ttggcgattc ttctgctcgt | 180 |
| gttatcgttc ttacaaaaac attcgatttc acaggcacag aaggcacaac aacagaaaca | 240 |
| ggctgcgctc cttggggcac agcttctgct tgccaagttg ctatcaacaa aaacgattgg | 300 |
| tgcacaaaact accaacctaa cgctccttct gtttctgtta catacgataa cgctggcgtt | 360 |
| cttggcatca cagttaaatc taacaaatct cttgttggcg aaggctcttc tggcgttatc | 420 |
| aaaggcaaag gccttcgtat cgtttctggc gcttctaacg ttatcatcca aaacatcgct | 480 |
| atcacagatc ttaaccctaa atacgtttgg ggcggcgatg ctatcacact tgataacgct | 540 |
| gatatggttt ggatcgatca tgttacaaca gctcgtatcg gccgtcaaca tcttgttctt | 600 |
| ggcacatctg cttctaaccg tgttacagtt tctaactctt acttcaacgg cgttacatct | 660 |
| tactctgcta catgcgatgg ctaccattac tggggcatct accttacagg ctctaacgat | 720 |
| atggttacac ttaaaggcaa ctacatctac catatgtctg gccgttctcc taaagttggc | 780 |
| ggcaacacac ttcttcatgc tgttaacaac tactggtacg attcttctgg ccatgctttc | 840 |
| gaaatcgatt ctggcggcta cgttcttgct gaaggcaact tttccaaaa catccctaca | 900 |
| gttatcgaag gcacagttgg cggccaactt ttcacatctc ctgattcttc tacaaacgct | 960 |
| atctgctcta cataccttgg ccatacatgc caagttaacg gcttcggctc ttctggcaca | 1020 |
| ttcaaacaag ctgatacagc tttccttgtt aacttccaag gcaaaaacat cgcttctgct | 1080 |
| tctgcttaca cagttgctca atcttctgtt ccttctaacg ctggccaagg caaactttga | 1140 |

<210> SEQ ID NO 15
<211> LENGTH: 2252
<212> TYPE: DNA
<213> ORGANISM: Artificial Sequence
<220> FEATURE:
<223> OTHER INFORMATION: Synthetic nucleic acid sequence encoding a
      galactosidase

<400> SEQUENCE: 15

| | |
|---|---|
| atgttccgtt ctacagctac agttgctgct gctacagcta tgggccttct tacagctaca | 60 |
| ggccatggct ctcttgctat cgctcaaggc acaacaggct ctaacgctgt tgttgttgat | 120 |
| ggcacaaact tcgctcttaa cggcgcttct atgtcttacg ttttccatgc taactctaca | 180 |
| acaggcgatc ttgtttctga tcatttcggc gctacaatct ctggcgctat ccctgctcct | 240 |
| aaagaacctg ctgttaacgg ctgggttggc atgcctggcc gtatccgtcg tgaattccct | 300 |
| gatcaaggcc gtggcgattt ccgtatccct gctgttcgta ccgtcaaac agctggctac | 360 |
| acagtttctg atcttcaata ccaaggccat gaagttgttg atggcaaacc tgctcttcct | 420 |
| ggccttcctg ctacattcgg cgaagctggc gatgttacaa cacttgttgt tcatctttac | 480 |
| gataactact ctgctgttgc tgctgatctt tcttactctg ttttccctga attcgatgct | 540 |
| gttgttcgtt ctgttaacgt tacaaacaaa ggcaaaggca acatcacaat cgaaaaccctt | 600 |
| gcttctcttt ctgttgattt ccctcttgaa gatcttgatc ttgtttctct tcgtggcgat | 660 |
| tgggctcgtg aagctaaccg tgaacgtcgt cgtgttgaat acggcatcca aggcttcggc | 720 |
| tcttctacag gctactcttc tcatcttcat aacccttttct tcgctcttgt tcatccttct | 780 |

| | |
|---|---:|
| acaacagaat ctcaaggcga agcttggggc ttcaaccttg tttacacagg ctctttctct | 840 |
| gctcaagttg aaaaaggctc tcaaggcctt acacgtgctc ttatcggctt caaccctgat | 900 |
| caactttctt ggaaccttgg ccctggcgaa acacttacat ctcctgaatg cgtttctgtt | 960 |
| tactctaaag atggcatcgg cggcatgtct cgtaaattcc atcgtcttta ccgtaaacat | 1020 |
| cttatccgtt ctaaattcgc tacatctgat cgtcctcctc ttcttaactc ttgggaaggc | 1080 |
| gtttacttcg atttcaacca atcttctatc gaaacacttg ctgaacaatc tgctgctctt | 1140 |
| ggcatccgtc ttttcgttat ggatgatggc tggttcggcg ataaataccc tcgtacatct | 1200 |
| gataacgctg gccttggcga ttggacacct aaccctgatc gtttccctaa cggccttgaa | 1260 |
| cctgttgttg aagaaatcac aaaccttaca gttaacgata catctgctga aaaacttcgt | 1320 |
| ttcggcatct gggttgaacc tgaaatggtt aaccctaact cttctcttta ccgtgaacat | 1380 |
| cctgattggg ctcttcatgc tggcgcttac gctcgtacag aacgtcgtaa ccaacttgtt | 1440 |
| cttaaccttg ctcttcctga agttcaagaa tacatcatcg atttcatgac agatcttctt | 1500 |
| aactctgctg atatctctta catcaaatgg ataacaacc gtggcatcca tgaagctcct | 1560 |
| tctccttcta cagatcatga atacatgctt ggcgtttacc gtgttttcga tacacttaca | 1620 |
| gctcgtttcc ctgatgttct ttgggaaggc tgcgcttctg gcggcggccg tttcgatgct | 1680 |
| ggcgttcttc attacttccc tcaaatctgg acatctgata acacagatgg cgttgatcgt | 1740 |
| gttacaatcc aattcggcac atctcttgct taccctcctt ctgctatggg cgctcatctt | 1800 |
| tctgctgttc ctaaccatca aacaggccgt acagttcctc ttgaattccg tgctcatgtt | 1860 |
| gctatgatgg gcggctcttt cggccttgaa cttgatcctg ctacacttca agatgatcct | 1920 |
| gatgttcctg aacttatcca atggctgaa aaagttaacc ctcttgttct taacggcgat | 1980 |
| cttaccgtc ttcgtcttcc tgaagaatct caatggcctg ctgctctttt cgttgctgaa | 2040 |
| gatggctctc aagctgttct tttctacttc caactttctc ctaacgttaa ccatgctgct | 2100 |
| ccttgggttc gtcttcaagg ccttgatcct gaagcttctt acacagttga tggcgataaa | 2160 |
| acatacacag gcgctacact tatgaacctt ggccttcaat acacattcga tacagaaacg | 2220 |
| gctctaaagt tgttttcctt gaacgtcaat ga | 2252 |

<210> SEQ ID NO 16
<211> LENGTH: 1143
<212> TYPE: DNA
<213> ORGANISM: Artificial Sequence
<220> FEATURE:
<223> OTHER INFORMATION: Synthetic nucleic acid sequence encoding a
     polygalacturnoase

<400> SEQUENCE: 16

| | |
|---|---:|
| atgttctacg ctcttggccc tcttgctctt ttcgctttcg ctacagaagt tatggctaca | 60 |
| cctgttgctt accctatgac aacagcttct cctacacttg ctaacgtga ttcttgcaca | 120 |
| ttctctggct ctgatggcgc tgcttctgct ctcgttctc aaacagattg cgctacaatc | 180 |
| acactttctg atatcacagt tccttctggc acaacacttg atctttctga tcttgaagat | 240 |
| gatacaacag ttatcttcga aggcacaaca tcttgggaat acgaagaatg ggatggccct | 300 |
| cttcttcaaa tcaaaggcaa cggcatcaca atcaaaggcg ctgatggcgc taaacttaac | 360 |
| cctgatggct ctcgttggtg ggatggcgaa ggctctaacg gcggcgttac aaaacctaaa | 420 |
| ttcttctacg ctcatgatct tacagattct acaatccaaa acctttacat cgaaaacaca | 480 |
| cctgttcaag ctgtttctat caacggctgc gatggcctta caatcacaga tatgacaatc | 540 |

```
gataactctg ctggcgatga tgctggcggc cataacacag atggcttcga tatcggcgaa      600
tcttctaacg ttgttatcac aggcgctaaa gtttacaacc aagatgattg cgttgctgtt      660
aactctggca catctatcac attctctggc ggcacatgct ctggcggcca tggcctttct      720
atcggctctg ttggcggccg tgatgataac acagttgata cagttacatt caaagattct      780
acagtttcta actctgttaa cggcatccgt atcaaagcta atctggcga aacaggcgaa       840 atcaaaggcg ttacatactc tggcatctct cttgaatcta tctctgatta cggcatcctt      900
atcgaacaaa actacgatgg cggcgatctt gatggcgaag ttacatctgg catccctatc      960
acagatctta caatcgaaaa catctctggc tctggcgctg ttgattctga tggctacaac     1020
atcgttatcg tttgcggcga tgatgcttgc tctaactgga catggtctga tgttgaagtt     1080
acaggcggcg aagattacgg ctcttgcgaa acgttcctt ctgttgcttc ttgctctaca      1140
tga                                                                   1143

<210> SEQ ID NO 17
<211> LENGTH: 1305
<212> TYPE: DNA
<213> ORGANISM: Artificial Sequence
<220> FEATURE:
<223> OTHER INFORMATION: Synthetic nucleic acid sequence encoding a
      monooxygenase

<400> SEQUENCE: 17
atgtctgttg ctcgtacagc tggcttcgct ctttgcttctg ctgctatcgt tgctggccat       60
ggctacgtta caggcatcgt tgctgatggc acatactacg gcggctacct tgttaaccaa      120 taccttact ctaacgatcc tcctgctgtt gttggctggg ctgaagatgc tacagatctt       180
ggcttcgttg atggctctgg ctacacatct ggcgatatca tctgccataa agatgctaca      240
aacgctcaag cttctgctac agttgctgct ggcggcacag ttgaacttca atggacagaa      300
tggcctgaat ctcatcatgg ccctgttatc gattacatcg cttcttgcaa cggcgattgc      360
acaacagttg ataaaacaac acttgaatgg gttaaaatct ctgaatctgg ccttgttgat      420
ggctcttctg ctcctggcac atgggcttct gataacctta tctctaacaa caactcttgg      480
acagttacaa tcccttcttc tcttgctgct ggcggctacg tcttcgtca tgaaatcatc       540 gctcttcatt ctgctggcaa cgaaaacggc gctcaaaact accctcaatg cgttaacctt      600
gaagttacag gcggcggctc tgcttctcct tctggcacag ttggcacaga actttacaca      660
cctacagatc ctggcatcct tgttaacatc tacacatctc ttgattctta cacaatccct      720
ggccctgctc tttgggatgg cgcttcttct ctggcggca actctggctc tggctctgct       780
tcttcttctg ctgctgctac atctacacct acaacacctt ctgtttctgt tcctgttatc     840
cctacagctt cttctggcgc ttcttctaca cctcttgttc ctacaccttc tgctcctgct      900
gttacacctt ctgttcctgc tggcaaccaa gctcctcaac ctacatacac atctacatac      960
atcgaaacag aaacacttcc tggccaaaca gttacatcta caacacaga atacgcttct     1020 gaacctacac aacctgctgt tgaaacacaa gttgctcaac cttctgaaac agaagctgct     1080
acatctacat ctcagttac agaaacagct ctgctacag ctgctcctac aggctcttct      1140
ggctcttctt ctggctctgg ctcttcttct acagaactc ctacagattc ttcttctctt     1200
tctgattact ctcttcctct ttctgctgaa gaattcctta accttcttaa agaaacactt     1260
aaatggcttg ttacagataa agttcatgct cgttctcttc attga                     1305

<210> SEQ ID NO 18
```

<211> LENGTH: 864
<212> TYPE: DNA
<213> ORGANISM: Artificial Sequence
<220> FEATURE:
<223> OTHER INFORMATION: Synthetic nucleic acid sequence encoding a monooxygenase

<400> SEQUENCE: 18

```
atgaaacttt ctcttcttgc tgctgctgct atcgctccta tggtttctgc tcattacttc      60
ttcgatacac ttgttatcga tggccaagaa acaacaccta accaatacgt tcgttctaac     120
acacgtcctg aaaaatacaa ccctacaaaa tgggttaaca cacgtgatga tatgacacct     180
gatatgccta tttccgttg caacaaaggc tctttcacat cgctggcca aacagataca      240
gctgaagtta agctggctc taaacttgct atgaaacttg cgttggcgc tacaatgcaa      300
catcctggcc ctggccttgt ttacatgtct aaagctcctg cgctgctaa ccaatacgaa     360
ggcgatggcg attggttcaa atccatgaa gaaggcatct gcgatacatc taagatatc      420
aaaacagatg cttggtgcac atgggataaa gatcgtatcg aattcacaat ccctgctgat    480
cttcctgatg gcgaatacct tatccgttct gaacatatcg gcgttcatgg cgctcatgat    540
ggccaagctg aattctacta cgaatgcgct caagttaaag ttacaggcgg cggcaacggc    600
aaccctcaag atacaatcaa attccctggc ggctaccaaa aagatgatcc ttctttcaac    660
ttctctgttt ggggcggcat gaaagattac cctatgcctg ccctgctgt ttacacaggc    720
ggctctggct cttctacagg ctcttacaac gaatctaacg ctgaagattc taacgaatac    780
ccttaccaaa aagaatctgg cacatgccaa tctaacttct accgtcgtga acatgctcgt    840
gatttctctc atcgtcgtgc ttga                                            864
```

<210> SEQ ID NO 19
<211> LENGTH: 696
<212> TYPE: DNA
<213> ORGANISM: Artificial Sequence
<220> FEATURE:
<223> OTHER INFORMATION: Synthetic nucleic acid sequence encoding a monooxygenase

<400> SEQUENCE: 19

```
atgaaatctg gccttctttt cacaacagct tctcttgctc ttacagcttc tgctcattac      60
gttttccctg ctcttgttca agatggcgct gctacaggcg attggaaata cgttcgtgat    120
tggacaggct cttacggcaa cggccctgtt gaagatgtta catctcttga tatccgttgc    180
aacaaagatg cttctacaaa cggcaacgct acagaaacac ttcctgttaa agctggcgaa    240
gaaatcggct tcacagttcg tacaaacatc ggccatcctg ccctcttct tgcttacatg    300
gctaaagctc ctggcgatgc ttctgatttc gatggcgatg ccaagtttg gttcaaaatc    360
tacgaagatg ccctacagt tacagatgat ggccttacat ggccttctga tggcgctaca    420
aacgttaact tcacaatccc ttcttctctt cctgatggcg attaccttct tcgtgttgaa    480
catatcgctc ttcatggcgc tggcacagaa ggcggcgctc aattctacct tcttgcggc    540
caagtttctg ttacaggcgg cggcaacggc gatcctgctc tcttgttgc tttccctggc    600
gcttacgatc ctacagatcc tggcatcctt atcaacatct actggcctgt tcctacaaac    660
tacacacctc ctggccctaa agtttggtct ggctga                              696
```

<210> SEQ ID NO 20
<211> LENGTH: 1209
<212> TYPE: DNA
<213> ORGANISM: Artificial Sequence
<220> FEATURE:
<223> OTHER INFORMATION: Synthetic nucleic acid sequence encoding a
      monooxygenase

<400> SEQUENCE: 20

```
atgtctcgtc ttgtttcttt cgcttctctt cttgctgctg ttaacgctca tggctacgtt      60
caaacatcg ttgttaacgg cgtttactac tctggctggg aaatcaacac ataccctttac     120
atgacagatc ctcctgttgt tgctgcttgg caaatcccta actctaacgg ccctgttgat     180
gtttctaacg gctacacaac agaagatatc atctgcaacc ttaacgctac aaacgctgct     240
ggctacgttg aagttgctgc tggcgataaa atcaaccttc aatggtctgc ttggcctgat     300
acacatcatg gccctgttat ctcttacctt gctgattgcg gcgatgattg cacaacagtt     360
gataaaacaa cacttgaatt cttcaaaatc gatgctgttg gccttgttga tgattctaca     420
gttcctggca catggggcga tgatgaactt atcgaaaaca caactcttg  gatggttgaa     480
atccctacat ctatcgctcc tggcaactac gttcttcgtc atgaaatcat cgctcttcat     540
tctgctggca cagaaggcgg cgctcaaaac taccctcaat gcttcaacct taagttaca      600
ggctctggca cagattctcc tgctggcaca cttggcacag aactttacaa ccttgatgat     660
cctggcatcc ttgttaacat ctacgcttct cttcctctacat acgttatccc tggccctaca     720
ctttactctg gcgctacatc tatcgctcaa gctacatctg ctatcacagc tacaggctct     780
gctacatctg gcgctggcgg cgctgctgct acaggctctt ctgctgctac aacaacagct     840
gctgctgctt ctacaacagc tacacctaca acagctgctg ctcaaacagc taaatctgct     900
tctgctcctt cttctgctgc tacaggctct gttcctgctg ctcctacaac agctacagtt     960
tctacaacaa catctatcgc tacatctgtt ggcacaacac ttacacgtac aacacttgct    1020
acaacaacaa cagctgctgc tgctgaacct tctgcttctg ctcctgctcc ttctggcaac    1080
tctgcttctg ctctaaccc tctttacgct caatgcggcg gccttaactt caaaggcgct    1140
tctggctgcg ttgctggcgc tacatgcaaa aaaatgaacc cttactactc tcaatgcgtt    1200
tctgcttga                                                             1209
```

<210> SEQ ID NO 21
<211> LENGTH: 249
<212> TYPE: PRT
<213> ORGANISM: Artificial Sequence
<220> FEATURE:
<223> OTHER INFORMATION: Synthetic amino acid sequence of a feruloyl
      esterase

<400> SEQUENCE: 21

```
Ala Asn Ser Pro Gly Cys Gly Lys Gln Pro Thr Leu Thr Asn Gly Val
1               5                   10                  15
Asn Gln Ile Asn Gly Arg Glu Tyr Val Leu Lys Ile Pro Asp Gly Tyr
            20                  25                  30
Asp Pro Ser Lys Pro His His Leu Ile Phe Gly Leu His Trp Arg Gly
        35                  40                  45
Gly Asn Met Tyr Asn Val Val Asn Gly Asp Ser Ile Gln Pro Trp Tyr
    50                  55                  60
Gly Leu Glu Ala Arg Ala Gln Gly Ser Ala Ile Phe Val Ala Pro Asn
65                  70                  75                  80
Gly Leu Asn Ala Gly Trp Ala Asn Thr Asn Gly Glu Asp Val Ala Phe
                85                  90                  95
Ile Asp Ala Ile Met Glu Gln Val Glu Asp Leu Cys Val Asp Gln
            100                 105                 110
```

```
Ala Ser Arg Phe Ala Thr Gly Phe Ser Trp Gly Gly Met Ser Tyr
            115                 120                 125

Ala Leu Ala Cys Ala Arg Ala Ala Glu Phe Arg Ala Val Ser Val Leu
        130                 135                 140

Ser Gly Gly Leu Ile Ser Gly Cys Asp Gly Gly Asn Asp Pro Ile Ala
145                 150                 155                 160

Tyr Leu Gly Ile His Gly Ile Asn Asp Pro Val Leu Pro Leu Asp Gly
                165                 170                 175

Gly Val Thr Leu Ala Asn Thr Phe Val Ser Asn Asn Gly Cys Gln Pro
            180                 185                 190

Thr Asp Ile Gly Gln Pro Ala Ser Gly Ser Gly Gly Ser Val Arg Thr
        195                 200                 205

Asp Phe Ser Gly Cys Ser His Pro Val Ser Phe Ile Ala Tyr Asp Gly
    210                 215                 220

Gly His Asp Gly Ala Pro Leu Gly Val Gly Ser Ser Leu Ala Pro Asp
225                 230                 235                 240

Ala Thr Trp Glu Phe Phe Met Ala Ala
                245

<210> SEQ ID NO 22
<211> LENGTH: 412
<212> TYPE: PRT
<213> ORGANISM: Artificial Sequence
<220> FEATURE:
<223> OTHER INFORMATION: Synthetic amino acid sequence of a cellulase

<400> SEQUENCE: 22

Gln Gln Ile Gly Thr Pro Glu Ile Arg Pro Arg Leu Thr Thr Tyr His
1               5                   10                  15

Cys Thr Ser Ala Asn Gly Cys Thr Glu Gln Asn Thr Ser Val Val Leu
            20                  25                  30

Asp Ala Ala Thr His Pro Ile His Asp Ala Ser Asn Pro Ser Val Ser
        35                  40                  45

Cys Thr Thr Ser Asn Gly Leu Asn Pro Ala Leu Cys Pro Asp Lys Gln
    50                  55                  60

Thr Cys Ala Asp Asn Cys Val Ile Asp Gly Ile Thr Asp Tyr Ala Ala
65                  70                  75                  80

His Gly Val Glu Thr His Gly Ser Arg Leu Thr Leu Thr Gln Tyr Arg
                85                  90                  95

Asn Val Asn Gly Ala Leu Ser Ser Val Ser Pro Arg Val Tyr Leu Val
            100                 105                 110

Asp Glu Ser Asp Pro Asp Glu Gln Glu Tyr Arg Ala Leu Ser Leu Leu
        115                 120                 125

Ala Gln Glu Phe Thr Phe Thr Val Asn Val Ser Ala Leu Pro Cys Gly
    130                 135                 140

Met Asn Gly Ala Leu Tyr Leu Ser Glu Met Ser Pro Ser Gly Gly Arg
145                 150                 155                 160

Ser Ala Leu Asn Pro Ala Gly Ala Ser Tyr Gly Thr Gly Tyr Cys Asp
                165                 170                 175

Ala Gln Cys Tyr Val Asn Pro Trp Ile Asn Gly Glu Gly Asn Ile Asn
            180                 185                 190

Gly Tyr Gly Ala Cys Cys Asn Glu Met Asp Ile Trp Glu Ala Asn Ser
        195                 200                 205

Arg Ser Thr Gly Phe Thr Pro His Ala Cys Leu Tyr Glu Pro Glu Glu
    210                 215                 220
```

```
Thr Glu Gly Arg Gly Val Tyr Glu Cys Ala Ser Glu Asp Glu Cys Asp
225                 230                 235                 240

Ser Ala Gly Glu Asn Asp Gly Ile Cys Asp Lys Trp Gly Cys Gly Phe
                245                 250                 255

Asn Pro Tyr Ala Leu Gly Asn Thr Glu Tyr Tyr Gly Arg Gly Gln Gly
                260                 265                 270

Phe Glu Val Asp Thr Lys Glu Pro Phe Thr Val Val Thr Gln Phe Leu
                275                 280                 285

Thr Asp Asp Gly Thr Ser Thr Gly Ala Leu Thr Glu Ile Arg Arg Leu
290                 295                 300

Tyr Ile Gln Asn Gly Gln Val Ile Glu Ala Val Val Ser Ser Gly Ala
305                 310                 315                 320

Asp Ser Leu Thr Asp Ser Leu Cys Ala Ser Thr Ala Ser Trp Phe Asp
                325                 330                 335

Ser Tyr Gly Gly Met Glu Gly Met Gly Arg Ala Leu Gly Arg Gly Met
                340                 345                 350

Val Leu Ala Met Ser Ile Trp Asn Asp Ala Gly Gly Tyr Met Gln Trp
                355                 360                 365

Leu Asp Gly Gly Asp Ala Gly Pro Cys Asn Ala Thr Glu Gly Ala Pro
370                 375                 380

Glu Phe Ile Glu Glu His Thr Pro Trp Thr Arg Val Val Phe Glu Asp
385                 390                 395                 400

Leu Lys Trp Gly Asp Ile Gly Ser Thr Phe Gln Ala
                405                 410

<210> SEQ ID NO 23
<211> LENGTH: 779
<212> TYPE: PRT
<213> ORGANISM: Artificial Sequence
<220> FEATURE:
<223> OTHER INFORMATION: Synthetic amino acid sequence of a cellobiose
      dehydrogenase

<400> SEQUENCE: 23

His Ser Phe Leu Arg Ser Phe Ala Ala Leu Val Ala Ala Gly Ser Asp
1               5                   10                  15

Pro Asp Thr Gly Ile Val Phe Asp Thr Trp Thr Val Glu Ala Ser Ser
                20                  25                  30

Ser Ser Ala Gly Phe Thr Phe Gly Val Ser Leu Pro Glu Asp Ala Leu
                35                  40                  45

Asp Thr Asp Ala Thr Glu Phe Ile Gly Tyr Leu Ser Cys Ser Ser Ser
                50                  55                  60

Ser Thr Ser Glu Phe Thr Gly Trp Cys Gly Leu Ser Met Gly Ser Ser
65                  70                  75                  80

Met Asn Ser Asn Leu Leu Val Ala Tyr Ala Gln Asp Asp Thr Val
                85                  90                  95

Leu Thr Ser Phe Arg Phe Ser Ser Gly Tyr Ala Met Pro Ser Val Tyr
                100                 105                 110

Ser Gly Asn Ala Thr Leu Thr Gln Ile Ser Ser Thr Val Thr Ala Asp
                115                 120                 125

Lys Phe Glu Val Leu Phe Arg Cys Glu Glu Cys Leu Arg Trp Asp His
                130                 135                 140

Glu Gly Val Ser Gly Ser Ala Thr Thr Ser Ala Gly Gln Leu Ile Leu
145                 150                 155                 160

Ala Trp Ala Gln Ala Glu Glu Ser Pro Thr Asn Ala Asp Cys Pro Asp
```

```
                165                 170                 175
Asp Leu Ser Leu Val Gln His Glu Ala Gln Gly Ile Trp Val Gly Lys
            180                 185                 190

Leu Ser Gly Asp Ala Ala Thr Ser Asn Tyr Glu Thr Trp Ala Ala Leu
        195                 200                 205

Ala Thr Asn Val Val Asp Gly Thr Cys Gly Thr Asp Gly Gly Gly Gly
    210                 215                 220

Gly Asp Asn Gly Asn Gly Thr Thr Pro Gly Val Pro Val Pro Thr Asn
225                 230                 235                 240

Val Thr Tyr Asp Tyr Ile Ile Val Gly Ser Gly Pro Ala Gly Met Val
                245                 250                 255

Leu Ala Asp Arg Leu Ser Glu Ala Gly Ala Lys Thr Leu Leu Ile Glu
            260                 265                 270

Lys Gly Pro Pro Ser Ile Gly Leu Trp Asn Gly Thr Met Lys Pro Asp
        275                 280                 285

Trp Leu Asn Gly Thr Asp Leu Thr Arg Phe Asp Val Pro Gly Leu Cys
    290                 295                 300

Asn Glu Ile Trp Lys Asn Ser Asp Gly Ile Ala Cys Pro Asp Asn Asp
305                 310                 315                 320

Gln Met Ala Gly Cys Leu Val Gly Gly Thr Ala Val Asn Ser Gly
                325                 330                 335

Leu Trp Trp Lys Pro Tyr Ser Lys Asp Phe Asp Glu Ser Phe Pro Glu
            340                 345                 350

Thr Trp Lys Tyr Asp Asp Val Arg Asp Ala Val Thr Arg Val Phe Thr
        355                 360                 365

Arg Ile Pro Gly Thr Thr Pro Ser Thr Asp Asn Arg Leu Tyr Leu
    370                 375                 380

Ala Glu Gly Pro Ser Val Ile Met Asn Gly Leu Leu Ala Ser Gly Trp
385                 390                 395                 400

Lys Gly Thr Thr Phe Asn Asp Glu Pro Glu Glu Lys Tyr Lys Ser Val
                405                 410                 415

Gly Tyr Ser Pro Tyr Met Phe Ser His Gly Gln Arg Asn Gly Pro Met
            420                 425                 430

Ala Thr Tyr Leu Leu Asp Ala Tyr Gln Arg Pro Asn Phe Asp Leu Trp
        435                 440                 445

Val Asn Thr Val Val Arg Arg Val Val Arg Asp Gly Ala Thr Val Thr
    450                 455                 460

Gly Val Glu Val Glu Pro Phe Asn Asp Gly Tyr Glu Gly Ser Leu
465                 470                 475                 480

Gln Leu Asn Glu Gly Gly Arg Val Ile Leu Ser Ala Gly Ala Phe Gly
                485                 490                 495

Thr Pro Lys Ile Leu Phe Arg Ser Gly Ile Gly Pro Glu Asp Gln Leu
            500                 505                 510

Ala Ile Val Asn Gly Ser Ala Ser Asp Gly Glu Thr Met Ile Ser Glu
        515                 520                 525

Asp Gln Trp Ile Asn Leu Pro Val Gly Glu Asn Leu Met Asp His Pro
    530                 535                 540

Asn Thr Glu Ile Val Val Gln His Pro Asp Val Val Phe Tyr Asp Tyr
545                 550                 555                 560

Tyr Ala Ala Tyr Asp Asp Pro Ile Glu Ala Asp Ala Gln Ser Tyr Leu
                565                 570                 575

Val Asn Arg Thr Gly Pro Leu Ala Gln Ser Ala Pro Asn Val Asn Pro
            580                 585                 590
```

Val Phe Phe Asp Gln Val Thr Gly Ser Asp Asn Val Thr Arg Gln Leu
            595                 600                 605

Gln Tyr Gln Ala Arg Val Glu Gly Ser His Asn Val Ala Asp Gly His
        610                 615                 620

Thr Ile Ser Ile Ser Gln Tyr Val Gly Arg Gly Gln Thr Ser Arg Gly
625                 630                 635                 640

Lys Leu Thr Ile Thr Ser Ala Leu Asn Thr Val Ser Thr Leu Pro
                645                 650                 655

Trp Leu Gln Asp Asp Asn Asp Thr Asp Ala Val Ile Ala Gly Leu Glu
            660                 665                 670

Arg Leu Arg Asp Ser Leu Ser Thr Ile Gln Gly Leu Thr Trp Ala Tyr
            675                 680                 685

Pro Lys Ala Asn Val Ser Met Ala Glu His Val Asn Ser Met Ala Lys
        690                 695                 700

Thr Gly Arg Gly Ser Asn His Trp Met Gly Ser Cys Lys Met Gly Pro
705                 710                 715                 720

Asp Asp Gly Arg Asp Gly Gly Ser Ser Val Val Asp Leu Asn Thr Lys
                725                 730                 735

Val Tyr Gly Met Asp Asn Leu Phe Val Val Asp Ala Ser Ile Phe Pro
            740                 745                 750

Gly Met Ile Ser Thr Asn Pro Ser Ala Tyr Ile Thr Val Val Ala Glu
        755                 760                 765

Arg Ala Ala Glu Arg Ile Leu Ala Leu Gln Gly
        770                 775

<210> SEQ ID NO 24
<211> LENGTH: 507
<212> TYPE: PRT
<213> ORGANISM: Artificial Sequence
<220> FEATURE:
<223> OTHER INFORMATION: Synthetic amino acid sequence of a cellulose
      1,4-beta-cellobiosidase

<400> SEQUENCE: 24

Gln Lys Val Gly Thr Gln Gln Ala Glu Val His Pro Gly Leu Thr Trp
1               5                   10                  15

Gln Thr Cys Thr Ser Gly Ser Cys Thr Thr Val Asn Gly Glu Val
            20                  25                  30

Thr Ile Asp Ala Asn Trp Arg Trp Leu His Thr Val Asn Gly Tyr Thr
            35                  40                  45

Asn Cys Tyr Thr Gly Asn Glu Trp Asp Thr Ser Ile Cys Thr Ser Asn
    50                  55                  60

Glu Val Cys Ala Glu Gln Cys Ala Val Asp Gly Ala Asn Tyr Ala Ser
65                  70                  75                  80

Thr Tyr Gly Ile Thr Thr Ser Gly Ser Ser Leu Arg Leu Asn Phe Val
                85                  90                  95

Thr Gln Ser Gln Gln Lys Asn Ile Gly Ser Arg Val Tyr Leu Met Asp
            100                 105                 110

Asp Glu Asp Thr Tyr Thr Met Phe Tyr Leu Leu Asn Lys Glu Phe Thr
        115                 120                 125

Phe Asp Val Asp Val Ser Glu Leu Pro Cys Gly Leu Asn Gly Ala Val
    130                 135                 140

Tyr Phe Val Ser Met Asp Ala Asp Gly Gly Lys Ser Arg Tyr Ala Thr
145                 150                 155                 160

Asn Glu Ala Gly Ala Lys Tyr Gly Thr Gly Tyr Cys Asp Ser Gln Cys

```
            165                 170                 175
Pro Arg Asp Leu Lys Phe Ile Asn Gly Val Ala Asn Val Glu Gly Trp
        180                 185                 190

Glu Ser Ser Asp Thr Asn Pro Asn Gly Val Gly Asn His Gly Ser
        195                 200                 205

Cys Cys Ala Glu Met Asp Ile Trp Glu Ala Asn Ser Ile Ser Thr Ala
        210                 215                 220

Phe Thr Pro His Pro Cys Asp Thr Pro Gly Gln Thr Leu Cys Thr Gly
225                 230                 235                 240

Asp Ser Cys Gly Gly Thr Tyr Ser Asn Asp Arg Tyr Gly Gly Thr Cys
                245                 250                 255

Asp Pro Asp Gly Cys Asp Phe Asn Ser Tyr Arg Gln Gly Asn Lys Thr
                260                 265                 270

Phe Tyr Gly Pro Gly Leu Thr Val Asp Thr Asn Ser Pro Val Thr Val
                275                 280                 285

Val Thr Gln Phe Leu Thr Asp Asp Asn Thr Asp Thr Gly Thr Leu Ser
        290                 295                 300

Glu Ile Lys Arg Phe Tyr Val Gln Asn Gly Val Val Ile Pro Asn Ser
305                 310                 315                 320

Glu Ser Thr Tyr Pro Ala Asn Pro Gly Asn Ser Ile Thr Thr Glu Phe
                325                 330                 335

Cys Glu Ser Gln Lys Glu Leu Phe Gly Asp Val Asp Val Phe Ser Ala
                340                 345                 350

His Gly Gly Met Ala Gly Met Gly Ala Ala Leu Glu Gln Gly Met Val
                355                 360                 365

Leu Val Leu Ser Leu Trp Asp Asp Asn Tyr Ser Asn Met Leu Trp Leu
        370                 375                 380

Asp Ser Asn Tyr Pro Thr Asp Ala Asp Pro Thr Gln Pro Gly Ile Ala
385                 390                 395                 400

Arg Gly Thr Cys Pro Thr Asp Ser Gly Val Pro Ser Glu Val Glu Ala
                405                 410                 415

Gln Tyr Pro Asn Ala Tyr Val Val Tyr Ser Asn Ile Lys Phe Gly Pro
                420                 425                 430

Ile Gly Ser Thr Phe Gly Asn Gly Gly Ser Gly Pro Thr Thr Thr
        435                 440                 445

Val Thr Thr Ser Thr Ala Thr Ser Thr Thr Ser Ala Thr Ser Thr
        450                 455                 460

Ala Thr Gly Gln Ala Gln His Trp Glu Gln Cys Gly Gly Asn Gly Trp
465                 470                 475                 480

Thr Gly Pro Thr Val Cys Ala Ser Pro Trp Ala Cys Thr Val Val Asn
                485                 490                 495

Ser Trp Tyr Ser Gln Cys Leu Leu Glu Asp Gly
                500                 505

<210> SEQ ID NO 25
<211> LENGTH: 290
<212> TYPE: PRT
<213> ORGANISM: Artificial Sequence
<220> FEATURE:
<223> OTHER INFORMATION: Synthetic amino acid sequence of a xylanase

<400> SEQUENCE: 25

Ala Val Leu Pro Arg Gln Ser Ala Ser Leu Asn Asp Leu Phe Val Ala
1               5                   10                  15

Ala Gly Lys Ser Tyr Phe Gly Thr Cys Ser Asp Gln Ala Leu Leu Gln
```

-continued

```
                    20                  25                  30
Asn Ser Gln Asn Glu Ala Ile Val Ala Ser Gln Phe Gly Val Ile Thr
                35                  40                  45

Pro Glu Asn Ser Met Lys Trp Asp Ala Leu Glu Pro Ser Gln Gly Asn
 50                  55                  60

Phe Gly Trp Ser Gly Ala Asp Tyr Leu Val Asp Tyr Ala Thr Gln His
 65                  70                  75                  80

Asn Lys Lys Val Arg Gly His Thr Leu Val Trp His Ser Gln Leu Pro
                85                  90                  95

Ser Trp Val Ser Ser Ile Gly Asp Ala Asn Thr Leu Arg Ser Val Met
                100                 105                 110

Thr Asn His Ile Asn Glu Val Val Gly Arg Tyr Lys Gly Lys Ile Met
            115                 120                 125

His Trp Asp Val Val Asn Glu Ile Phe Asn Glu Asp Gly Thr Phe Arg
            130                 135                 140

Asn Ser Val Phe Tyr Asn Leu Leu Gly Glu Asp Phe Val Arg Ile Ala
145                 150                 155                 160

Phe Glu Thr Ala Arg Ala Ala Asp Pro Asp Ala Lys Leu Tyr Ile Asn
                165                 170                 175

Asp Tyr Asn Leu Asp Ser Ala Ser Tyr Ala Lys Thr Gln Ala Met Ala
                180                 185                 190

Ser Tyr Val Lys Lys Trp Leu Ala Glu Gly Val Pro Ile Asp Gly Ile
                195                 200                 205

Ala Leu Ser Ser Leu Ala Asn Thr Gly Val Ser Glu Val Ala Ile Thr
            210                 215                 220

Glu Leu Asp Ile Ala Gly Ala Ala Ser Ser Asp Tyr Leu Asn Leu Leu
225                 230                 235                 240

Asn Ala Cys Leu Asn Glu Gln Lys Cys Val Gly Ile Thr Val Trp Gly
                245                 250                 255

Val Ser Asp Lys Asp Ser Trp Arg Ala Ser Asp Ser Pro Leu Leu Phe
                260                 265                 270

Asp Gly Asn Tyr Gln Pro Lys Asp Ala Tyr Asn Ala Ile Val Asn Ala
            275                 280                 285

Leu Ser
    290

<210> SEQ ID NO 26
<211> LENGTH: 1020
<212> TYPE: PRT
<213> ORGANISM: Artificial Sequence
<220> FEATURE:
<223> OTHER INFORMATION: Synthetic amino acid sequence of a
      rhammnoglacturonan lyase

<400> SEQUENCE: 26

Ala Leu Thr Thr Thr Ser Asn Ser Thr His Tyr Thr Ile Ser Asn Ser
1               5                   10                  15

Arg Phe Ser Val Ala Val Ala Lys Ser Asn Gly His Val Val Asp Ala
                20                  25                  30

Asn Leu Asp Gly Gln Asp Leu Leu Gly Pro Leu Ser Gly Asn Ser Gly
            35                  40                  45

Lys Gly Pro Tyr Leu Asp Cys Ser Cys Thr Pro Glu Gly Phe Trp Thr
    50                  55                  60

Pro Gly Ala Glu Pro Ala Leu Val Asn Gly Thr Asp Ser Thr Gly Thr
65                  70                  75                  80
```

-continued

```
Pro Tyr Val Gly Val Ile Met Thr Asp Thr Tyr Glu Thr Thr Asn Gln
                 85                  90                  95
Thr Leu Ser Gln Tyr Leu Phe Leu Arg Gly Glu Glu Thr Gly Leu His
            100                 105                 110
Ala Phe Ser Arg Val Thr Tyr Tyr Asn Glu Ser Asp Tyr Phe Leu Arg
        115                 120                 125
Gly Leu Gly Glu Leu Arg Thr Leu Phe Arg Pro Asn Thr Asn Leu Trp
    130                 135                 140
Thr His Phe Ser Gly Ser Glu Gly Asn Tyr Gly Pro Met Pro Leu Ser
145                 150                 155                 160
Ser Thr Glu Lys Ile Thr Val Gln Asp Ala Thr Thr Tyr Leu Gly Asp
                165                 170                 175
Thr Thr Asp Asp Pro Tyr Val Ser Gln Tyr Ser Asp Tyr Phe Thr Lys
            180                 185                 190
Tyr Thr Leu Thr Glu Ser Trp Arg Asp His Asp Val His Gly His Phe
        195                 200                 205
Ser Asn Gly Ser Thr Ser Gly Asp Gly Asn Thr Tyr Gly Ala Trp Leu
    210                 215                 220
Val His Asn Thr Arg Glu Thr Tyr Tyr Gly Gly Pro Leu His Ala Asp
225                 230                 235                 240
Leu Val Val Asp Gly Ile Val Tyr Asn Tyr Ile Val Ser Gly His Tyr
                245                 250                 255
Gly Ala Pro Asn Pro Asn Leu Thr His Gly Phe Asp Arg Thr Phe Gly
            260                 265                 270
Pro Gln Tyr Tyr His Phe Asn Ser Gly Gly Pro Gly Thr Thr Leu Glu
        275                 280                 285
Glu Leu Arg Ala Asp Ala Ala Gln Tyr Ala Ser Pro Glu Trp Asn Ala
    290                 295                 300
Glu Phe Tyr Asp Ser Ile Ala Lys His Ile Pro Asn Tyr Val Pro Ser
305                 310                 315                 320
Thr Gly Arg Thr Thr Phe Arg Gly Lys Val Asn Leu Pro Lys Gly Ala
                325                 330                 335
Lys Lys Pro Ile Ile Val Leu Ser Glu Asn Glu Gln Asp Phe Gln Leu
            340                 345                 350
Asn Val Phe Lys Lys Asp Ser Leu Gln Tyr Trp Ala Glu Ile Asp Gly
        355                 360                 365
Ser Gly Ala Phe Thr Ile Pro Arg Val Val Lys Gly Thr Tyr Arg Val
    370                 375                 380
Thr Ile Tyr Ala Asp Glu Ile Phe Gly Trp Phe Ile Lys Asp Asn Val
385                 390                 395                 400
Lys Val Ile Gly Ser Asn Ala His Thr Phe Thr Trp Lys Glu Glu Thr
                405                 410                 415
Ala Gly Lys Glu Ile Trp Arg Ile Gly Val Pro Asp Lys Ser Ser Gly
            420                 425                 430
Glu Phe Leu His Gly Tyr Ala Pro Asp Thr Ser Lys Pro Leu Gln Pro
        435                 440                 445
Glu Gln Tyr Arg Ile Tyr Trp Gly Lys Tyr Asp Tyr Pro Ser Asp Phe
    450                 455                 460
Pro Glu Gly Val Asn Tyr His Val Gly Lys Ser Asp Pro Ala Lys Asp
465                 470                 475                 480
Leu Asn Tyr Ile His Trp Ser Phe Phe Pro Ser Gln Gly Asn His Leu
                485                 490                 495
Arg Asn Glu Pro Tyr Tyr Gln Asn Val Asn Asn Trp Thr Ile Thr Phe
```

-continued

```
            500                 505                 510
Asp Leu Thr Ala Ser Gln Leu Arg Asn Thr Lys Thr Ala Thr Phe Thr
            515                 520                 525
Val Gln Leu Ala Gly Thr Arg Asn Ala Asn Gly Asn Ser Lys Trp Asn
            530                 535                 540
Pro Asp Pro Ala Lys Tyr Asn Asn Leu Pro Trp Thr Val Asn Val Asn
545                 550                 555                 560
Gly Ile Tyr Glu Asp Thr Trp Glu Ile Pro Tyr Trp Arg Ser Gly Ser
                    565                 570                 575
Cys Gly Val Arg Ser Gly Val Gln Cys Gln Asn Thr Glu His Lys Phe
                580                 585                 590
Val Phe Asp Ala Gly Lys Leu Arg Lys Gly Arg Asn Glu Phe Val Leu
            595                 600                 605
Ser Leu Pro Phe Asn Ala Thr Ser Val Glu Thr Ala Leu Leu Pro Asn
            610                 615                 620
Ser Leu Tyr Val Gln Val Val Ser Met Glu Ala Val Ser Val Ser Asn
625                 630                 635                 640
Asp Met Arg Val Leu Val Gln Ala Phe Met Pro Leu Val Thr Trp Gly
                    645                 650                 655
Thr Ala Val Glu Lys Arg Val Leu Leu Thr Gly Ile Val Ser Val Ser
                660                 665                 670
Ala Met Ala Lys Glu Asp Tyr Pro Met Ile Ser Arg Pro Cys Pro Arg
            675                 680                 685
Lys Gly Gly Thr Arg Arg Lys Lys Glu Arg Lys Lys Glu Gly Lys
            690                 695                 700
Lys Gln Gly Arg Thr Val Leu Asp Ala Leu Leu Gln Arg Ser Glu Gln
705                 710                 715                 720
Asp Ser Phe Trp Ser Arg Phe Cys Arg Ser Pro Ile Glu Ser Val Ala
                    725                 730                 735
Gln Tyr Val Tyr Gly Gln Gly Ser Thr Ala Leu Arg Lys Lys Thr Thr
                740                 745                 750
Asp Asn Leu Val Arg Val Val Cys Val Ser Asp Thr His Asn Thr Lys
            755                 760                 765
Pro Asn Leu Pro Asp Gly Asp Ile Leu Ile His Ala Gly Asp Leu Thr
            770                 775                 780
Glu Ser Gly Thr Lys Glu Glu Leu Glu Lys Gln Ile Tyr Trp Leu Asp
785                 790                 795                 800
Ser Gln Pro His Arg Tyr Lys Ile Val Ile Ala Gly Asn His Glu Thr
                    805                 810                 815
Phe Leu Asp Arg Asn Tyr His Ser His His Gly Asn Glu Arg Val Thr
                820                 825                 830
Met Asp Trp Lys Ser Leu Ile Tyr Leu Glu Asn Thr Ser Ala Ile Leu
            835                 840                 845
Asp Leu Gly Ala Gly His Gln Leu Lys Val Phe Gly Ser Pro Tyr Thr
            850                 855                 860
Pro Lys His Gly Asn Gly Ala Phe Gln Tyr Pro Arg Thr Asp Thr Thr
865                 870                 875                 880
Thr Trp Glu Glu Ile Pro Lys Asp Thr Asp Leu Leu Val Thr His Gly
                    885                 890                 895
Pro Pro Lys Ala His Leu Asp Leu Gly His Leu Gly Cys Arg Val Leu
                900                 905                 910
Arg Gln Ala Leu Trp Glu Met Glu Ser Arg Pro Leu Leu His Val Phe
            915                 920                 925
```

```
Gly His Ile His Gly Gly Tyr Gly Lys Glu Val Val Cys Trp Asp Leu
            930                 935                 940

Cys Gln Arg Ala Tyr Glu Ala Ile Met Asp Gly Glu Ser Arg Trp Trp
945                 950                 955                 960

Asn Leu Cys Val Leu Phe Tyr Cys Trp Ile Leu Arg Leu Phe Phe Asp
                965                 970                 975

Trp Thr Ala Asp Gly Arg Ala Thr Val Leu Val Asn Ala Ala Thr Val
            980                 985                 990

Gly Gly Val Arg Asp Leu Lys Arg Arg Glu Ala Ile Cys Val Asp Ile
            995                 1000                1005

Gln Ala Gly Ser Lys Arg Phe Leu Ser Gly Cys Thr
    1010            1015                1020

<210> SEQ ID NO 27
<211> LENGTH: 228
<212> TYPE: PRT
<213> ORGANISM: Artificial Sequence
<220> FEATURE:
<223> OTHER INFORMATION: Synthetic amino acid sequence of a
      rhammnoglacturonan acetylesterase

<400> SEQUENCE: 27

Gln Thr Ile Tyr Leu Ala Gly Asp Ser Thr Met Ala Ser Ser Thr Pro
1               5                   10                  15

Gly Trp Gly Asp Tyr Ile Ala Asp Ser Val Ser Val Glu Ile Ser Asn
            20                  25                  30

Gln Ala Ile Gly Gly Arg Ser Ala Arg Ser Tyr Thr Arg Glu Gly Arg
        35                  40                  45

Phe Gln Ala Ile Ala Asp Val Leu Gln Ala Gly Asp Tyr Val Val Ile
    50                  55                  60

Glu Phe Gly His Asn Asp Gly Ser Leu Ser Asn Asp Asn Gly Arg
65              70                  75                  80

Thr Asp Cys Pro Gly Asp Gly Asp Glu Thr Cys Glu Thr Val Tyr Asn
                85                  90                  95

Gly Val Ala Glu Thr Val Leu Thr Phe Pro Ala Tyr Ile Glu Asn Ala
            100                 105                 110

Ala Leu Leu Phe Leu Glu Lys Gly Ala Asn Val Leu Ile Ser Ser Gln
        115                 120                 125

Thr Pro Asn Asn Pro Trp Glu Ser Gly Thr Phe Ser Tyr Thr Pro Asn
    130                 135                 140

Arg Phe Val Gly Tyr Ala Glu Leu Ala Ala Gln Arg Ala Gly Val Asp
145                 150                 155                 160

Tyr Val Asp His Gly Ala Tyr Thr Ala Ser Ile Phe Glu Ala Leu Gly
                165                 170                 175

Ala Asp Thr Val Asn Ser Phe Tyr Pro Asn Asp His Thr His Thr Asn
            180                 185                 190

Ala Glu Gly Ser Ser Val Val Ala Asp Ala Phe Leu Lys Ala Val Val
        195                 200                 205

Cys Ser Gly Val Ala Leu Asn Asp Val Leu Thr Arg Thr Asp Phe Asp
    210                 215                 220

Gly Glu Cys Leu
225

<210> SEQ ID NO 28
<211> LENGTH: 307
<212> TYPE: PRT
```

<213> ORGANISM: Artificial Sequence
<220> FEATURE:
<223> OTHER INFORMATION: Synthetic amino acid sequence of an endoglucanase

<400> SEQUENCE: 28

```
Ala Phe Thr Trp Leu Gly Thr Asn Glu Ala Gly Ala Glu Phe Gly Glu
1               5                   10                  15
Gly Ser Tyr Pro Gly Glu Leu Gly Thr Glu Tyr Ile Trp Pro Asp Leu
            20                  25                  30
Gly Thr Ile Gly Thr Leu Arg Asn Glu Gly Met Asn Ile Phe Arg Val
        35                  40                  45
Ala Phe Ser Met Glu Arg Leu Val Pro Asp Ser Leu Ala Gly Pro Val
    50                  55                  60
Ala Asp Glu Tyr Phe Gln Asp Leu Val Glu Thr Val Asn Gly Ile Thr
65                  70                  75                  80
Ala Leu Gly Ala Tyr Ala Val Leu Asp Pro His Asn Tyr Gly Arg Tyr
                85                  90                  95
Tyr Gly Asn Ile Ile Thr Ser Thr Asp Asp Phe Ala Ala Phe Trp Thr
            100                 105                 110
Ile Leu Ala Thr Glu Phe Ala Ser Asn Glu Leu Val Ile Phe Asp Thr
        115                 120                 125
Asn Asn Glu Tyr His Thr Met Asp Gln Ser Leu Val Leu Asn Leu Asn
130                 135                 140
Gln Ala Ala Ile Asp Ala Ile Arg Ala Ser Gly Ala Thr Ser Gln Tyr
145                 150                 155                 160
Ile Phe Ala Glu Gly Asn Ser Trp Thr Gly Ala Trp Thr Trp Val Asp
                165                 170                 175
Val Asn Asp Asn Met Lys Ala Leu Thr Asp Pro Gln Asp Lys Leu Ile
            180                 185                 190
Tyr Glu Met His Gln Tyr Leu Asp Ser Asp Gly Ser Gly Thr Asn Thr
        195                 200                 205
Ala Cys Val Ser Ser Thr Ile Gly Ser Glu Arg Val Thr Ala Ala Thr
    210                 215                 220
Asn Trp Leu Arg Glu Asn Gly Lys Leu Gly Val Leu Gly Glu Phe Ala
225                 230                 235                 240
Gly Ala Asn Asn Gln Val Cys Lys Asp Ala Val Ala Asp Leu Leu Glu
                245                 250                 255
Tyr Leu Glu Glu Asn Ser Asp Val Trp Leu Gly Ala Leu Trp Trp Ala
            260                 265                 270
Ala Gly Pro Trp Trp Gly Asp Tyr Met Phe Asn Met Glu Pro Thr Ser
        275                 280                 285
Gly Ile Ala Tyr Gln Glu Tyr Ser Glu Ile Leu Gln Pro Tyr Phe Val
    290                 295                 300
Gly Ser Gln
305
```

<210> SEQ ID NO 29
<211> LENGTH: 365
<212> TYPE: PRT
<213> ORGANISM: Artificial Sequence
<220> FEATURE:
<223> OTHER INFORMATION: Synthetic amino acid sequence of a mannanase

<400> SEQUENCE: 29

```
Leu Pro His Ala Ser Thr Pro Val Tyr Thr Pro Ser Thr Thr Pro Ser
1               5                   10                  15
```

```
Pro Thr Pro Thr Pro Ser Ala Ser Gly Ser Phe Ala Thr Thr Ser Gly
             20                  25                  30

Ile Gln Phe Val Ile Asp Gly Glu Ala Gly Tyr Phe Pro Gly Ser Asn
         35                  40                  45

Ala Tyr Trp Ile Gly Phe Leu Lys Asn Asn Ser Asp Val Asp Leu Val
 50                  55                  60

Phe Asp His Met Ala Ser Ser Gly Leu Arg Ile Leu Arg Val Trp Gly
 65                  70                  75                  80

Phe Asn Asp Val Asn Thr Ala Pro Thr Asp Gly Ser Val Tyr Phe Gln
                 85                  90                  95

Leu His Gln Asp Gly Lys Ser Thr Ile Asn Thr Gly Lys Asp Gly Leu
            100                 105                 110

Gln Arg Leu Asp Tyr Val Val His Ser Ala Glu Lys His Gly Ile Lys
            115                 120                 125

Leu Ile Ile Asn Phe Val Asn Tyr Trp Asp Asp Tyr Gly Gly Met Asn
130                 135                 140

Ala Tyr Met Arg Ala Tyr Gly Gly Asp Lys Ala Asp Trp Phe Glu
145                 150                 155                 160

Asn Glu Gly Ile Gln Ala Ala Tyr Gln Ala Tyr Val Glu Ala Val Val
                165                 170                 175

Lys Arg Tyr Ile Asn Ser Thr Ala Val Phe Ala Trp Glu Leu Ala Asn
            180                 185                 190

Glu Pro Arg Cys Thr Gly Cys Glu Pro Ser Val Leu His Asn Trp Ile
            195                 200                 205

Glu Lys Thr Ser Ala Phe Ile Lys Gly Leu Asp Glu Lys His Leu Val
            210                 215                 220

Cys Ile Gly Asp Gly Ser Asp Gly Ser Tyr Pro Phe Gln Tyr Thr Glu
225                 230                 235                 240

Gly Ser Asp Phe Ala Ala Ala Leu Thr Ile Asp Thr Ile Asp Phe Gly
                245                 250                 255

Thr Phe His Leu Tyr Pro Asp Ser Trp Gly Thr Asn Asn Asp Trp Gly
            260                 265                 270

Lys Leu Trp Ile Thr Ser His Ala Ala Cys Ala Ala Ala Gly Lys
            275                 280                 285

Pro Cys Leu Phe Glu Glu Tyr Gly Val Thr Ser Asn His Cys Ala Ile
290                 295                 300

Glu Lys Gln Trp Gln Asn Ala Ala Leu Asn Ala Thr Gly Ile Ala Ala
305                 310                 315                 320

Asp Leu Tyr Trp Gln Tyr Gly Asp Thr Leu Ser Ser Gly Pro Ser Pro
                325                 330                 335

Asp Asp Gly Asn Thr Phe Tyr Tyr Gly Ser Glu Glu Phe Glu Cys Leu
            340                 345                 350

Val Thr Asn His Val Glu Thr Ile Glu Arg Ser Ala Lys
            355                 360                 365
```

<210> SEQ ID NO 30
<211> LENGTH: 431
<212> TYPE: PRT
<213> ORGANISM: Artificial Sequence
<220> FEATURE:
<223> OTHER INFORMATION: Synthetic amino acid sequence of a
      cellobiohydrolase

<400> SEQUENCE: 30

Gln Gln Thr Leu Tyr Gly Gln Cys Gly Gly Ser Gly Trp Thr Gly Ala

```
                1               5                    10                   15
            Thr Ser Cys Val Ala Gly Ala Ala Cys Ser Thr Leu Asn Gln Trp Tyr
                            20                  25                  30
            Ala Gln Cys Leu Pro Ala Ala Thr Thr Thr Ser Thr Thr Leu Thr Thr
                            35                  40                  45
            Thr Thr Ser Ser Val Thr Thr Thr Ser Asn Pro Gly Ser Thr Thr Thr
            50                          55                  60
            Thr Ser Ser Val Thr Val Thr Ala Thr Ala Ser Gly Asn Pro Phe Ser
            65                  70                  75                  80
            Gly Tyr Gln Leu Tyr Val Asn Pro Tyr Ser Ser Glu Val Gln Ser
                            85                  90                  95
            Ile Ala Ile Pro Ser Leu Thr Gly Thr Leu Ser Ser Leu Ala Pro Ala
                            100                 105                 110
            Ala Thr Ala Ala Ala Lys Thr Arg Asp Val Ala Ala Lys Val Pro Thr
                            115                 120                 125
            Met Ala Thr Tyr Leu Ala Asp Ile Arg Ser Gln Asn Ala Ala Gly Ala
                            130                 135                 140
            Asn Pro Pro Ile Ala Gly Gln Phe Val Val Tyr Asp Leu Pro Asp Arg
            145                         150                 155                 160
            Asp Cys Ala Ala Leu Ala Ser Asn Gly Glu Phe Ala Ile Ser Asp Gly
                                165                 170                 175
            Gly Val Gln His Tyr Lys Asp Tyr Ile Asp Ser Ile Arg Glu Ile Leu
                            180                 185                 190
            Val Glu Tyr Ser Asp Val His Val Ile Leu Val Ile Glu Pro Asp Ser
                            195                 200                 205
            Leu Ala Asn Leu Val Thr Asn Leu Asn Val Ala Lys Cys Ala Asn Ala
            210                         215                 220
            Gln Ser Ala Tyr Leu Glu Cys Thr Asn Tyr Ala Val Thr Gln Leu Asn
            225                         230                 235                 240
            Leu Pro Asn Val Ala Met Tyr Leu Asp Ala Gly His Ala Gly Trp Leu
                                245                 250                 255
            Gly Trp Pro Ala Asn Leu Gln Pro Ala Ala Asn Leu Tyr Ala Gly Val
                            260                 265                 270
            Tyr Ser Asp Ala Gly Ser Pro Ala Ala Leu Arg Gly Leu Ala Thr Asn
                            275                 280                 285
            Val Ala Asn Tyr Asn Ala Trp Ala Ile Asp Thr Cys Pro Ser Tyr Thr
                            290                 295                 300
            Gln Gly Asn Ser Val Cys Asp Glu Lys Asp Tyr Ile Asn Ala Leu Ala
            305                         310                 315                 320
            Pro Leu Leu Arg Ala Gln Gly Phe Asp Ala His Phe Ile Thr Asp Thr
                                325                 330                 335
            Gly Arg Asn Gly Lys Gln Pro Thr Gly Gln Gln Ala Trp Gly Asp Trp
                            340                 345                 350
            Cys Asn Val Ile Gly Thr Gly Phe Gly Ala Arg Pro Ser Thr Asn Thr
                            355                 360                 365
            Gly Asp Ser Leu Leu Asp Ala Phe Val Trp Val Lys Pro Gly Gly Glu
                            370                 375                 380
            Ser Asp Gly Thr Ser Asp Thr Ser Ala Ala Arg Tyr Asp Ala His Cys
            385                         390                 395                 400
            Gly Tyr Ser Asp Ala Leu Gln Pro Ala Pro Glu Ala Gly Thr Trp Phe
                                405                 410                 415
            Gln Ala Tyr Phe Val Gln Leu Leu Gln Asn Ala Asn Pro Ser Phe
                            420                 425                 430
```

```
<210> SEQ ID NO 31
<211> LENGTH: 240
<212> TYPE: PRT
<213> ORGANISM: Artificial Sequence
<220> FEATURE:
<223> OTHER INFORMATION: Synthetic amino acid sequence of a cutinase

<400> SEQUENCE: 31

Ser Pro Leu Asn Leu Asp Glu Arg Gln His Ala Val Gly Ser Ser Ser
1               5                   10                  15

Gly Asn Asp Leu Arg Asp Gly Asp Cys Lys Pro Val Thr Phe Ile Phe
            20                  25                  30

Ala Arg Ala Ser Thr Glu Pro Gly Leu Leu Gly Met Ser Thr Gly Pro
        35                  40                  45

Ala Val Cys Asn Asp Leu Lys Ala Asp Ala Ser Leu Gly Gly Val Ala
    50                  55                  60

Cys Gln Gly Val Gly Pro Lys Tyr Thr Ala Gly Leu Ala Glu Asn Ala
65                  70                  75                  80

Leu Pro Gln Gly Thr Ser Ser Ala Ala Ile Asn Glu Ala Lys Glu Leu
                85                  90                  95

Phe Glu Leu Ala Ala Ser Lys Cys Pro Asp Thr Arg Ile Val Ala Gly
            100                 105                 110

Gly Tyr Ser Gln Gly Thr Ala Val Met His Gly Ala Ile Pro Asp Leu
        115                 120                 125

Ser Asp Glu Ile Lys Asp Lys Ile Ala Gly Val Val Leu Phe Gly Asp
    130                 135                 140

Thr Arg Asn Lys Gln Asp Gly Gly Gln Ile Lys Asn Phe Pro Lys Asp
145                 150                 155                 160

Lys Ile Lys Ile Tyr Cys Ala Thr Gly Asp Leu Val Cys Asp Gly Thr
                165                 170                 175

Leu Val Val Thr Ala Ala His Phe Thr Tyr Val Ala Asn Thr Gly Glu
            180                 185                 190

Ala Ser Lys Trp Leu Glu Gln Gln Leu Ala Ser Met Pro Ala Ser Thr
        195                 200                 205

Ser Thr Ser Ser Ser Ser Ser Ser Ser Ser Ala Pro Ala Ser Gln
    210                 215                 220

Thr Ser Gln Ser Ser Gly Leu Ser Ser Trp Phe Ser Gly Leu Gly Asn
225                 230                 235                 240

<210> SEQ ID NO 32
<211> LENGTH: 500
<212> TYPE: PRT
<213> ORGANISM: Artificial Sequence
<220> FEATURE:
<223> OTHER INFORMATION: Synthetic amino acid sequence of a
      rhamnogalacturonase

<400> SEQUENCE: 32

Gln Leu Ser Gly Ser Val Gly Pro Leu Thr Ser Val Ser Ser Lys Ser
1               5                   10                  15

Gln Thr Lys Thr Cys Asn Val Leu Asp Tyr Gly Ala Val Ala Asp Lys
            20                  25                  30

Ser Thr Asp Ile Gly Pro Ala Leu Ser Ser Ala Trp Asp Glu Cys Ala
        35                  40                  45

Asp Gly Gly Val Val Tyr Ile Pro Pro Gly Asp Tyr Ala Ile Glu Thr
    50                  55                  60
```

```
Trp Val Lys Leu Ser Gly Gly Lys Ala Cys Ala Ile Gln Leu Asp Gly
 65                  70                  75                  80

Ile Ile Tyr Arg Thr Gly Thr Asp Gly Gly Asn Met Ile Met Ile Glu
                     85                  90                  95

His Thr Ser Asp Phe Glu Phe Phe Ser Ser Thr Ser Lys Gly Ala Phe
                100                 105                 110

Gln Gly Tyr Gly Tyr Glu Phe His Ala Lys Gly Ser Ser Asp Gly Pro
            115                 120                 125

Arg Ile Leu Arg Leu Tyr Asp Val Ser Asp Phe Ser Val His Asp Val
130                 135                 140

Ala Leu Val Asp Ser Pro Leu Phe His Phe Ser Met Asp Thr Cys Ser
145                 150                 155                 160

Asn Gly Glu Val Tyr Asn Met Ala Ile Arg Gly Gly Asn Met Gly Gly
                165                 170                 175

Leu Asp Gly Ile Asp Val Trp Ser Thr Asn Val Trp Ile His Asp Val
                180                 185                 190

Ile His Ala Glu His Ser Pro Phe Asp Ala Arg Ser Asp Arg Leu Gln
            195                 200                 205

Ser Pro Ser Lys Asn Ile Leu Val Glu Asn Ile Tyr Cys Asn Trp Ser
210                 215                 220

Gly Gly Cys Ala Met Gly Ser Leu Gly Thr Asp Thr Asp Ile Ser Asp
225                 230                 235                 240

Ile Val Tyr Arg Asn Val Tyr Thr Trp Lys Ser Asn Gln Met Tyr Met
                245                 250                 255

Val Lys Ser Asn Gly Gly Ser Gly Thr Val Ser Asn Leu Val Leu Glu
                260                 265                 270

Asn Phe Ile Ala Arg Ala Asp Ser Lys Gly His Gly Asn Ala Tyr Ser
            275                 280                 285

Leu Asp Ile Asp Ser Ala Trp Ser Ser Met Ser Thr Ile Glu Gly Asp
290                 295                 300

Gly Val Glu Leu Lys Asn Val Thr Ile Arg Asn Trp Lys Gly Thr Glu
305                 310                 315                 320

Ala Asp Gly Ser Gln Arg Gly Pro Ile Lys Val Lys Cys Ala Ser Gly
                325                 330                 335

Ala Pro Cys Thr Asp Val Thr Val Glu Asp Phe Ala Met Trp Thr Glu
            340                 345                 350

Ser Gly Asp Glu Gln Thr Tyr Val Cys Glu Asn Ala Phe Gly Asp Gly
            355                 360                 365

Phe Cys Leu Ala Asp Gly Asp Gly Thr Ser Thr Phe Thr Thr Thr Leu
370                 375                 380

Thr Ala Ser Ala Ala Pro Ser Gly Tyr Ser Ala Pro Ser Met Asp Ala
385                 390                 395                 400

Asp Leu Glu Thr Ala Phe Gly Thr Asp Ser Glu Ile Pro Ile Pro Thr
                405                 410                 415

Ile Pro Thr Ser Phe Tyr Pro Gly Ala Thr Pro Tyr Ser Ala Leu Ala
                420                 425                 430

Gly Ala Ser Val Ser Ser Ser Gln Val Pro Ala Ala Ser Ser Ser Ala
            435                 440                 445

Glu Ala Lys Phe Val Ala Ser Pro Ala Thr Ser Ser Pro Thr Ala Thr
            450                 455                 460

Ser Thr Ala Ile Ser Ser Val Asp Pro Val Ser Ala Ala Thr Thr Thr
465                 470                 475                 480

Ala Thr Ser His Gly His Gly Lys Ser His His Lys His Gln Cys Arg
```

```
                        485                 490                 495

Ala His Arg His
            500

<210> SEQ ID NO 33
<211> LENGTH: 599
<212> TYPE: PRT
<213> ORGANISM: Artificial Sequence
<220> FEATURE:
<223> OTHER INFORMATION: Synthetic amino acid sequence of a glucosidase

<400> SEQUENCE: 33

Leu Ala Ile Lys Ser Asn Glu Pro Glu Leu Arg Arg Asp Ala Leu
1               5                   10                  15

Pro Ile Tyr Lys Asn Ala Ser Tyr Cys Val Asp Glu Arg Val Arg Asp
                20                  25                  30

Leu Leu Ser Arg Met Thr Leu Glu Glu Lys Ala Gly Gln Leu Phe His
            35                  40                  45

Lys Gln Leu Ser Glu Gly Pro Leu Asp Asp Ser Ser Gly Asn Ser
50                  55                  60

Thr Glu Thr Met Ile Gly Lys Lys His Met Thr His Phe Asn Leu Ala
65                  70                  75                  80

Ser Asp Ile Thr Asn Ala Thr Gln Thr Ala Glu Phe Ile Asn Leu Ile
                85                  90                  95

Gln Lys Arg Ala Leu Gln Thr Arg Leu Gly Ile Pro Ile Thr Ile Ser
            100                 105                 110

Thr Asp Pro Arg His Ser Phe Thr Glu Asn Val Gly Thr Gly Phe Gln
        115                 120                 125

Ala Gly Val Phe Ser Gln Trp Pro Glu Ser Leu Gly Leu Ala Ala Leu
    130                 135                 140

Arg Asp Pro Gln Leu Val Arg Glu Phe Ala Glu Val Ala Arg Glu Glu
145                 150                 155                 160

Tyr Leu Ala Val Gly Ile Arg Ala Ala Leu His Pro Gln Val Asp Leu
                165                 170                 175

Ser Thr Glu Pro Arg Trp Ala Arg Ile Ser Gly Thr Trp Gly Glu Asn
            180                 185                 190

Ser Thr Leu Thr Ser Glu Leu Ile Val Glu Tyr Ile Lys Gly Phe Gln
        195                 200                 205

Gly Glu Gly Lys Leu Gly Pro Lys Ser Val Lys Thr Val Lys His
    210                 215                 220

Phe Pro Gly Gly Gly Pro Met Glu Asn Gly Glu Asp Ser His Phe Tyr
225                 230                 235                 240

Tyr Gly Lys Asn Gln Thr Tyr Pro Gly Asn Asn Ile Asp Glu His Leu
                245                 250                 255

Ile Pro Phe Lys Ala Ala Leu Ala Ala Gly Ala Thr Glu Ile Met Pro
            260                 265                 270

Tyr Tyr Ser Arg Pro Ile Gly Thr Asn Trp Glu Ala Val Gly Phe Ser
        275                 280                 285

Phe Asn Lys Glu Ile Val Thr Asp Leu Leu Arg Gly Glu Leu Gly Phe
    290                 295                 300

Asp Gly Ile Val Leu Thr Asp Trp Gly Leu Ile Thr Asp Thr Tyr Ile
305                 310                 315                 320

Gly Asn Gln Tyr Met Pro Ala Arg Ala Trp Gly Val Glu Tyr Leu Ser
                325                 330                 335

Glu Leu Gln Arg Ala Ala Arg Ile Leu Asp Ala Gly Cys Asp Gln Phe
```

```
                340                 345                 350
Gly Gly Glu Glu Arg Pro Glu Leu Ile Val Gln Leu Val Arg Glu Gly
            355                 360                 365

Thr Ile Ser Glu Asp Arg Ile Asp Val Ser Val Ala Arg Leu Leu Lys
        370                 375                 380

Glu Lys Phe Leu Leu Gly Leu Phe Asp Asn Pro Phe Val Asn Ala Ser
385                 390                 395                 400

Ala Ala Asn Asn Ile Val Gly Asn Glu His Phe Val Asn Leu Gly Arg
                405                 410                 415

Asp Ala Gln Arg Arg Ser Tyr Thr Leu Leu Thr Asn Asn Gln Thr Ile
            420                 425                 430

Leu Pro Leu Ala Lys Pro Gly Glu Gly Thr Arg Phe Tyr Ile Glu Gly
        435                 440                 445

Phe Asp Ser Ala Phe Met Ser Ala Arg Asn Tyr Thr Val Val Asn Thr
    450                 455                 460

Thr Glu Glu Ala Asp Phe Ala Leu Leu Arg Tyr Asn Ala Pro Tyr Glu
465                 470                 475                 480

Pro Arg Asn Gly Thr Phe Glu Ala Asn Phe His Ala Gly Ser Leu Ala
                485                 490                 495

Phe Asn Ala Thr Glu Lys Ala Arg Gln Ala Lys Ile Tyr Ser Ser Leu
            500                 505                 510

Pro Thr Ile Val Asp Ile Ile Leu Asp Arg Pro Ala Val Ile Pro Glu
        515                 520                 525

Val Val Glu Gln Ala Gln Ala Val Leu Ala Ser Tyr Gly Ser Asp Ser
    530                 535                 540

Glu Ala Phe Leu Asp Val Val Phe Gly Val Ser Lys Pro Glu Gly Lys
545                 550                 555                 560

Leu Pro Phe Asp Leu Pro Arg Ser Met Asp Ala Val Glu Ala Gln Ala
                565                 570                 575

Glu Asp Leu Pro Phe Asp Thr Glu Asn Pro Val Phe Arg Tyr Gly His
            580                 585                 590

Gly Leu Glu Tyr Glu Asp Asn
        595

<210> SEQ ID NO 34
<211> LENGTH: 360
<212> TYPE: PRT
<213> ORGANISM: Artificial Sequence
<220> FEATURE:
<223> OTHER INFORMATION: Synthetic amino acid sequence of a pectin lyase

<400> SEQUENCE: 34

Ala Gly Val Thr Gly Ser Ala Glu Gly Phe Ala Lys Gly Val Thr Gly
1               5                   10                  15

Gly Gly Ser Ala Thr Pro Val Tyr Pro Ser Thr Thr Ala Glu Leu Val
            20                  25                  30

Ser Tyr Leu Gly Asp Ser Ser Ala Arg Val Ile Val Leu Thr Lys Thr
        35                  40                  45

Phe Asp Phe Thr Gly Thr Glu Gly Thr Thr Thr Glu Thr Gly Cys Ala
    50                  55                  60

Pro Trp Gly Thr Ala Ser Ala Cys Gln Val Ala Ile Asn Lys Asn Asp
65                  70                  75                  80

Trp Cys Thr Asn Tyr Gln Pro Asn Ala Pro Ser Val Ser Val Thr Tyr
                85                  90                  95

Asp Asn Ala Gly Val Leu Gly Ile Thr Val Lys Ser Asn Lys Ser Leu
```

```
        100                 105                 110
Val Gly Glu Gly Ser Ser Gly Val Ile Lys Gly Lys Gly Leu Arg Ile
        115                 120                 125

Val Ser Gly Ala Ser Asn Val Ile Ile Gln Asn Ile Ala Ile Thr Asp
        130                 135                 140

Leu Asn Pro Lys Tyr Val Trp Gly Gly Asp Ala Ile Thr Leu Asp Asn
145                 150                 155                 160

Ala Asp Met Val Trp Ile Asp His Val Thr Thr Ala Arg Ile Gly Arg
                165                 170                 175

Gln His Leu Val Leu Gly Thr Ser Ala Ser Asn Arg Val Thr Val Ser
        180                 185                 190

Asn Ser Tyr Phe Asn Gly Val Thr Ser Tyr Ser Ala Thr Cys Asp Gly
        195                 200                 205

Tyr His Tyr Trp Gly Ile Tyr Leu Thr Gly Ser Asn Asp Met Val Thr
        210                 215                 220

Leu Lys Gly Asn Tyr Ile Tyr His Met Ser Gly Arg Ser Pro Lys Val
225                 230                 235                 240

Gly Gly Asn Thr Leu Leu His Ala Val Asn Asn Tyr Trp Tyr Asp Ser
                245                 250                 255

Ser Gly His Ala Phe Glu Ile Asp Ser Gly Gly Tyr Val Leu Ala Glu
        260                 265                 270

Gly Asn Val Phe Gln Asn Ile Pro Thr Val Ile Glu Gly Thr Val Gly
        275                 280                 285

Gly Gln Leu Phe Thr Ser Pro Asp Ser Ser Thr Asn Ala Ile Cys Ser
        290                 295                 300

Thr Tyr Leu Gly His Thr Cys Gln Val Asn Gly Phe Gly Ser Ser Gly
305                 310                 315                 320

Thr Phe Lys Gln Ala Asp Thr Ala Phe Leu Val Asn Phe Gln Gly Lys
                325                 330                 335

Asn Ile Ala Ser Ala Ser Ala Tyr Thr Val Ala Gln Ser Ser Val Pro
        340                 345                 350

Ser Asn Ala Gly Gln Gly Lys Leu
        355                 360

<210> SEQ ID NO 35
<211> LENGTH: 729
<212> TYPE: PRT
<213> ORGANISM: Artificial Sequence
<220> FEATURE:
<223> OTHER INFORMATION: Synthetic amino acid sequence of a
      galactosidase

<400> SEQUENCE: 35

His Gly Ser Leu Ala Ile Ala Gln Gly Thr Thr Gly Ser Asn Ala Val
1               5                   10                  15

Val Val Asp Gly Thr Asn Phe Ala Leu Asn Gly Ala Ser Met Ser Tyr
                20                  25                  30

Val Phe His Ala Asn Ser Thr Thr Gly Asp Leu Val Ser Asp His Phe
            35                  40                  45

Gly Ala Thr Ile Ser Gly Ala Ile Pro Ala Pro Lys Glu Pro Ala Val
        50                  55                  60

Asn Gly Trp Val Gly Met Pro Gly Arg Ile Arg Arg Glu Phe Pro Asp
65                  70                  75                  80

Gln Gly Arg Gly Asp Phe Arg Ile Pro Ala Val Arg Ile Arg Gln Thr
                85                  90                  95
```

-continued

```
Ala Gly Tyr Thr Val Ser Asp Leu Gln Tyr Gln Gly His Glu Val Val
                100                 105                 110
Asp Gly Lys Pro Ala Leu Pro Gly Leu Pro Ala Thr Phe Gly Glu Ala
            115                 120                 125
Gly Asp Val Thr Thr Leu Val Val His Leu Tyr Asp Asn Tyr Ser Ala
        130                 135                 140
Val Ala Ala Asp Leu Ser Tyr Ser Val Phe Pro Glu Phe Asp Ala Val
145                 150                 155                 160
Val Arg Ser Val Asn Val Thr Asn Lys Gly Lys Gly Asn Ile Thr Ile
                165                 170                 175
Glu Asn Leu Ala Ser Leu Ser Val Asp Phe Pro Leu Glu Asp Leu Asp
            180                 185                 190
Leu Val Ser Leu Arg Gly Asp Trp Ala Arg Glu Ala Asn Arg Glu Arg
        195                 200                 205
Arg Arg Val Glu Tyr Gly Ile Gln Gly Phe Gly Ser Ser Thr Gly Tyr
210                 215                 220
Ser Ser His Leu His Asn Pro Phe Phe Ala Leu Val His Pro Ser Thr
225                 230                 235                 240
Thr Glu Ser Gln Gly Glu Ala Trp Gly Phe Asn Leu Val Tyr Thr Gly
                245                 250                 255
Ser Phe Ser Ala Gln Val Glu Lys Gly Ser Gln Gly Leu Thr Arg Ala
            260                 265                 270
Leu Ile Gly Phe Asn Pro Asp Gln Leu Ser Trp Asn Leu Gly Pro Gly
        275                 280                 285
Glu Thr Leu Thr Ser Pro Glu Cys Val Ser Val Tyr Ser Lys Asp Gly
290                 295                 300
Ile Gly Gly Met Ser Arg Lys Phe His Arg Leu Tyr Arg Lys His Leu
305                 310                 315                 320
Ile Arg Ser Lys Phe Ala Thr Ser Asp Arg Pro Leu Leu Asn Ser
                325                 330                 335
Trp Glu Gly Val Tyr Phe Asp Phe Asn Gln Ser Ser Ile Glu Thr Leu
            340                 345                 350
Ala Glu Gln Ser Ala Ala Leu Gly Ile Arg Leu Phe Val Met Asp Asp
        355                 360                 365
Gly Trp Phe Gly Asp Lys Tyr Pro Arg Thr Ser Asp Asn Ala Gly Leu
370                 375                 380
Gly Asp Trp Thr Pro Asn Pro Asp Arg Phe Pro Asn Gly Leu Glu Pro
385                 390                 395                 400
Val Val Glu Glu Ile Thr Asn Leu Thr Val Asn Asp Thr Ser Ala Glu
                405                 410                 415
Lys Leu Arg Phe Gly Ile Trp Val Glu Pro Glu Met Val Asn Pro Asn
            420                 425                 430
Ser Ser Leu Tyr Arg Glu His Pro Asp Trp Ala Leu His Ala Gly Ala
        435                 440                 445
Tyr Ala Arg Thr Glu Arg Arg Asn Gln Leu Val Leu Asn Leu Ala Leu
450                 455                 460
Pro Glu Val Gln Glu Tyr Ile Ile Asp Phe Met Thr Asp Leu Leu Asn
465                 470                 475                 480
Ser Ala Asp Ile Ser Tyr Ile Lys Trp Asp Asn Asn Arg Gly Ile His
                485                 490                 495
Glu Ala Pro Ser Pro Ser Thr Asp His Glu Tyr Met Leu Gly Val Tyr
            500                 505                 510
Arg Val Phe Asp Thr Leu Thr Ala Arg Phe Pro Asp Val Leu Trp Glu
```

```
                515                 520                 525
Gly Cys Ala Ser Gly Gly Arg Phe Asp Ala Gly Val Leu His Tyr
530                 535                 540

Phe Pro Gln Ile Trp Thr Ser Asp Asn Thr Asp Gly Val Asp Arg Val
545                 550                 555                 560

Thr Ile Gln Phe Gly Thr Ser Leu Ala Tyr Pro Pro Ser Ala Met Gly
                565                 570                 575

Ala His Leu Ser Ala Val Pro Asn His Gln Thr Gly Arg Thr Val Pro
                580                 585                 590

Leu Glu Phe Arg Ala His Val Ala Met Met Gly Gly Ser Phe Gly Leu
                595                 600                 605

Glu Leu Asp Pro Ala Thr Leu Gln Asp Asp Pro Asp Val Pro Glu Leu
610                 615                 620

Ile Gln Met Ala Glu Lys Val Asn Pro Leu Val Leu Asn Gly Asp Leu
625                 630                 635                 640

Tyr Arg Leu Arg Leu Pro Glu Glu Ser Gln Trp Pro Ala Ala Leu Phe
                645                 650                 655

Val Ala Glu Asp Gly Ser Gln Ala Val Leu Phe Tyr Phe Gln Leu Ser
                660                 665                 670

Pro Asn Val Asn His Ala Ala Pro Trp Val Arg Leu Gln Gly Leu Asp
                675                 680                 685

Pro Glu Ala Ser Tyr Thr Val Asp Gly Asp Lys Thr Tyr Thr Gly Ala
690                 695                 700

Thr Leu Met Asn Leu Gly Leu Gln Tyr Thr Phe Asp Thr Glu Tyr Gly
705                 710                 715                 720

Ser Lys Val Val Phe Leu Glu Arg Gln
                725

<210> SEQ ID NO 36
<211> LENGTH: 361
<212> TYPE: PRT
<213> ORGANISM: Artificial Sequence
<220> FEATURE:
<223> OTHER INFORMATION: Synthetic amino acid sequence of a
      polygalacturnoase

<400> SEQUENCE: 36

Thr Pro Val Ala Tyr Pro Met Thr Thr Ala Ser Pro Thr Leu Ala Lys
1               5                   10                  15

Arg Asp Ser Cys Thr Phe Ser Gly Ser Asp Gly Ala Ala Ser Ala Ser
                20                  25                  30

Arg Ser Gln Thr Asp Cys Ala Thr Ile Thr Leu Ser Asp Ile Thr Val
                35                  40                  45

Pro Ser Gly Thr Thr Leu Asp Leu Ser Asp Leu Glu Asp Asp Thr Thr
            50                  55                  60

Val Ile Phe Glu Gly Thr Thr Ser Trp Glu Tyr Glu Glu Trp Asp Gly
65                  70                  75                  80

Pro Leu Leu Gln Ile Lys Gly Asn Gly Ile Thr Ile Lys Gly Ala Asp
                85                  90                  95

Gly Ala Lys Leu Asn Pro Asp Gly Ser Arg Trp Trp Asp Gly Glu Gly
                100                 105                 110

Ser Asn Gly Gly Val Thr Lys Pro Lys Phe Phe Tyr Ala His Asp Leu
            115                 120                 125

Thr Asp Ser Thr Ile Gln Asn Leu Tyr Ile Glu Asn Thr Pro Val Gln
        130                 135                 140
```

Ala Val Ser Ile Asn Gly Cys Asp Gly Leu Thr Ile Thr Asp Met Thr
145                 150                 155                 160

Ile Asp Asn Ser Ala Gly Asp Ala Gly Gly His Asn Thr Asp Gly
        165                 170                 175

Phe Asp Ile Gly Glu Ser Ser Asn Val Val Ile Thr Gly Ala Lys Val
                180                 185                 190

Tyr Asn Gln Asp Asp Cys Val Ala Val Asn Ser Gly Thr Ser Ile Thr
            195                 200                 205

Phe Ser Gly Gly Thr Cys Ser Gly Gly His Gly Leu Ser Ile Gly Ser
        210                 215                 220

Val Gly Gly Arg Asp Asp Asn Thr Val Asp Thr Val Thr Phe Lys Asp
225                 230                 235                 240

Ser Thr Val Ser Asn Ser Val Asn Gly Ile Arg Ile Lys Ala Lys Ser
                245                 250                 255

Gly Glu Thr Gly Glu Ile Lys Gly Val Thr Tyr Ser Gly Ile Ser Leu
            260                 265                 270

Glu Ser Ile Ser Asp Tyr Gly Ile Leu Ile Glu Gln Asn Tyr Asp Gly
        275                 280                 285

Gly Asp Leu Asp Gly Glu Val Thr Ser Gly Ile Pro Ile Thr Asp Leu
290                 295                 300

Thr Ile Glu Asn Ile Ser Gly Ser Gly Ala Val Asp Ser Asp Gly Tyr
305                 310                 315                 320

Asn Ile Val Ile Val Cys Gly Asp Asp Ala Cys Ser Asn Trp Thr Trp
                325                 330                 335

Ser Asp Val Glu Val Thr Gly Gly Glu Asp Tyr Gly Ser Cys Glu Asn
            340                 345                 350

Val Pro Ser Val Ala Ser Cys Ser Thr
        355                 360

<210> SEQ ID NO 37
<211> LENGTH: 415
<212> TYPE: PRT
<213> ORGANISM: Artificial Sequence
<220> FEATURE:
<223> OTHER INFORMATION: Synthetic amino acid sequence of a
      monooxygenase

<400> SEQUENCE: 37

His Gly Tyr Val Thr Gly Ile Val Ala Asp Gly Thr Tyr Tyr Gly Gly
1               5                   10                  15

Tyr Leu Val Asn Gln Tyr Pro Tyr Ser Asn Asp Pro Pro Ala Val Val
            20                  25                  30

Gly Trp Ala Glu Asp Ala Thr Asp Leu Gly Phe Val Asp Gly Ser Gly
        35                  40                  45

Tyr Thr Ser Gly Asp Ile Ile Cys His Lys Asp Ala Thr Asn Ala Gln
    50                  55                  60

Ala Ser Ala Thr Val Ala Ala Gly Gly Thr Val Glu Leu Gln Trp Thr
65                  70                  75                  80

Glu Trp Pro Glu Ser His His Gly Pro Val Ile Asp Tyr Ile Ala Ser
                85                  90                  95

Cys Asn Gly Asp Cys Thr Thr Val Asp Lys Thr Thr Leu Glu Trp Val
            100                 105                 110

Lys Ile Ser Glu Ser Gly Leu Val Asp Gly Ser Ser Ala Pro Gly Thr
        115                 120                 125

Trp Ala Ser Asp Asn Leu Ile Ser Asn Asn Ser Trp Thr Val Thr
    130                 135                 140

Ile Pro Ser Ser Leu Ala Ala Gly Gly Tyr Val Leu Arg His Glu Ile
145                 150                 155                 160

Ile Ala Leu His Ser Ala Gly Asn Glu Asn Gly Ala Gln Asn Tyr Pro
                165                 170                 175

Gln Cys Val Asn Leu Glu Val Thr Gly Gly Ser Ala Ser Pro Ser
            180                 185                 190

Gly Thr Val Gly Thr Glu Leu Tyr Thr Pro Thr Asp Pro Gly Ile Leu
            195                 200                 205

Val Asn Ile Tyr Thr Ser Leu Asp Ser Tyr Thr Ile Pro Gly Pro Ala
        210                 215                 220

Leu Trp Asp Gly Ala Ser Ser Gly Gly Asn Ser Gly Ser Gly Ser
225                 230                 235                 240

Ala Ser Ser Ser Ala Ala Ala Thr Ser Thr Pro Thr Thr Pro Ser Val
                245                 250                 255

Ser Val Pro Val Ile Pro Thr Ala Ser Ser Gly Ala Ser Ser Thr Pro
            260                 265                 270

Leu Val Pro Thr Pro Ser Ala Pro Ala Val Thr Pro Ser Val Pro Ala
            275                 280                 285

Gly Asn Gln Ala Pro Gln Pro Thr Tyr Thr Ser Thr Tyr Ile Glu Thr
            290                 295                 300

Glu Thr Leu Pro Gly Gln Thr Val Thr Ser Thr Thr Thr Glu Tyr Ala
305                 310                 315                 320

Ser Glu Pro Thr Gln Pro Ala Val Glu Thr Gln Val Ala Gln Pro Ser
                325                 330                 335

Glu Thr Glu Ala Ala Thr Ser Thr Ser Thr Val Thr Glu Thr Ala Ser
            340                 345                 350

Ala Thr Ala Ala Pro Thr Gly Ser Ser Gly Ser Ser Ser Gly Ser Gly
            355                 360                 365

Ser Ser Ser Thr Glu Leu Pro Thr Asp Ser Ser Ser Leu Ser Asp Tyr
370                 375                 380

Phe Ser Ser Leu Ser Ala Glu Glu Phe Leu Asn Leu Leu Lys Glu Thr
385                 390                 395                 400

Leu Lys Trp Leu Val Thr Asp Lys Val His Ala Arg Ser Leu His
                405                 410                 415

<210> SEQ ID NO 38
<211> LENGTH: 270
<212> TYPE: PRT
<213> ORGANISM: Artificial Sequence
<220> FEATURE:
<223> OTHER INFORMATION: Synthetic amino acid sequence of a
      monooxygenase

<400> SEQUENCE: 38

His Tyr Phe Phe Asp Thr Leu Val Ile Asp Gly Gln Glu Thr Thr Pro
1               5                   10                  15

Asn Gln Tyr Val Arg Ser Asn Thr Arg Pro Glu Lys Tyr Asn Pro Thr
                20                  25                  30

Lys Trp Val Asn Thr Arg Asp Asp Met Thr Pro Asp Met Pro Asp Phe
            35                  40                  45

Arg Cys Asn Lys Gly Ser Phe Thr Phe Ala Gly Gln Thr Asp Thr Ala
        50                  55                  60

Glu Val Lys Ala Gly Ser Lys Leu Ala Met Lys Leu Gly Val Gly Ala
65                  70                  75                  80

Thr Met Gln His Pro Gly Pro Gly Leu Val Tyr Met Ser Lys Ala Pro

```
                    85                  90                  95
Gly Ala Ala Asn Gln Tyr Glu Gly Asp Gly Asp Trp Phe Lys Ile His
                100                 105                 110
Glu Glu Gly Ile Cys Asp Thr Ser Lys Asp Ile Lys Thr Asp Ala Trp
            115                 120                 125
Cys Thr Trp Asp Lys Asp Arg Ile Glu Phe Thr Ile Pro Ala Asp Leu
130                 135                 140
Pro Asp Gly Glu Tyr Leu Ile Arg Ser Glu His Ile Gly Val His Gly
145                 150                 155                 160
Ala His Asp Gly Gln Ala Glu Phe Tyr Tyr Glu Cys Ala Gln Val Lys
                165                 170                 175
Val Thr Gly Gly Gly Asn Gly Asn Pro Gln Asp Thr Ile Lys Phe Pro
                180                 185                 190
Gly Gly Tyr Gln Lys Asp Pro Ser Phe Asn Phe Ser Val Trp Gly
            195                 200                 205
Gly Met Lys Asp Tyr Pro Met Pro Gly Pro Ala Val Tyr Thr Gly Gly
            210                 215                 220
Ser Gly Ser Ser Thr Gly Ser Tyr Asn Glu Ser Asn Ala Glu Asp Ser
225                 230                 235                 240
Asn Glu Tyr Pro Tyr Gln Lys Glu Ser Gly Thr Cys Gln Ser Asn Phe
                245                 250                 255
Tyr Arg Arg Glu His Ala Arg Asp Phe Ser His Arg Arg Ala
                260                 265                 270

<210> SEQ ID NO 39
<211> LENGTH: 213
<212> TYPE: PRT
<213> ORGANISM: Artificial Sequence
<220> FEATURE:
<223> OTHER INFORMATION: Synthetic amino acid sequence of a
      monooxygenase

<400> SEQUENCE: 39

His Tyr Val Phe Pro Ala Leu Val Gln Asp Gly Ala Ala Thr Gly Asp
1               5                   10                  15
Trp Lys Tyr Val Arg Asp Trp Thr Gly Ser Tyr Gly Asn Gly Pro Val
                20                  25                  30
Glu Asp Val Thr Ser Leu Asp Ile Arg Cys Asn Lys Asp Ala Ser Thr
            35                  40                  45
Asn Gly Asn Ala Thr Glu Thr Leu Pro Val Lys Ala Gly Glu Glu Ile
        50                  55                  60
Gly Phe Thr Val Arg Thr Asn Ile Gly His Pro Gly Pro Leu Leu Ala
65                  70                  75                  80
Tyr Met Ala Lys Ala Pro Gly Asp Ala Ser Asp Phe Asp Gly Asp Gly
                85                  90                  95
Gln Val Trp Phe Lys Ile Tyr Glu Asp Gly Pro Thr Val Thr Asp Asp
                100                 105                 110
Gly Leu Thr Trp Pro Ser Asp Gly Ala Thr Asn Val Asn Phe Thr Ile
            115                 120                 125
Pro Ser Ser Leu Pro Asp Gly Asp Tyr Leu Leu Arg Val Glu His Ile
        130                 135                 140
Ala Leu His Gly Ala Gly Thr Glu Gly Gly Ala Gln Phe Tyr Leu Ser
145                 150                 155                 160
Cys Gly Gln Val Ser Val Thr Gly Gly Gly Asn Gly Asp Pro Ala Pro
                165                 170                 175
```

```
Leu Val Ala Phe Pro Gly Ala Tyr Asp Pro Thr Asp Pro Gly Ile Leu
                180                 185                 190

Ile Asn Ile Tyr Trp Pro Val Pro Thr Asn Tyr Thr Pro Pro Gly Pro
            195                 200                 205

Lys Val Trp Ser Gly
        210

<210> SEQ ID NO 40
<211> LENGTH: 386
<212> TYPE: PRT
<213> ORGANISM: Artificial Sequence
<220> FEATURE:
<223> OTHER INFORMATION: Synthetic amino acid sequence of a
      monooxygenase

<400> SEQUENCE: 40

His Gly Tyr Val Gln Asn Ile Val Val Asn Gly Val Tyr Tyr Ser Gly
 1               5                  10                  15

Trp Glu Ile Asn Thr Tyr Pro Tyr Met Thr Asp Pro Pro Val Val Ala
            20                  25                  30

Ala Trp Gln Ile Pro Asn Ser Asn Gly Pro Val Asp Val Ser Asn Gly
        35                  40                  45

Tyr Thr Thr Glu Asp Ile Ile Cys Asn Leu Asn Ala Thr Asn Ala Ala
 50                  55                  60

Gly Tyr Val Glu Val Ala Ala Gly Asp Lys Ile Asn Leu Gln Trp Ser
 65                  70                  75                  80

Ala Trp Pro Asp Thr His His Gly Pro Val Ile Ser Tyr Leu Ala Asp
                85                  90                  95

Cys Gly Asp Asp Cys Thr Thr Val Asp Lys Thr Thr Leu Glu Phe Phe
            100                 105                 110

Lys Ile Asp Ala Val Gly Leu Val Asp Asp Ser Thr Val Pro Gly Thr
        115                 120                 125

Trp Gly Asp Asp Glu Leu Ile Glu Asn Asn Ser Trp Met Val Glu
130                 135                 140

Ile Pro Thr Ser Ile Ala Pro Gly Asn Tyr Val Leu Arg His Glu Ile
145                 150                 155                 160

Ile Ala Leu His Ser Ala Gly Thr Glu Gly Gly Ala Gln Asn Tyr Pro
                165                 170                 175

Gln Cys Phe Asn Leu Lys Val Thr Gly Ser Gly Thr Asp Ser Pro Ala
            180                 185                 190

Gly Thr Leu Gly Thr Glu Leu Tyr Asn Leu Asp Asp Pro Gly Ile Leu
        195                 200                 205

Val Asn Ile Tyr Ala Ser Leu Ser Thr Tyr Val Ile Pro Gly Pro Thr
210                 215                 220

Leu Tyr Ser Gly Ala Thr Ser Ile Ala Gln Thr Ser Ala Ile Thr
225                 230                 235                 240

Ala Thr Gly Ser Ala Thr Ser Gly Ala Gly Ala Ala Thr Gly
                245                 250                 255

Ser Ser Ala Ala Thr Thr Thr Ala Ala Ala Ser Thr Thr Ala Thr
            260                 265                 270

Pro Thr Thr Ala Ala Ala Gln Thr Ala Lys Ser Ala Ser Ala Pro Ser
        275                 280                 285

Ser Ala Ala Thr Gly Ser Val Pro Ala Ala Pro Thr Thr Ala Thr Val
    290                 295                 300

Ser Thr Thr Thr Ser Ile Ala Thr Ser Val Gly Thr Thr Leu Thr Arg
305                 310                 315                 320
```

-continued

```
Thr Thr Leu Ala Thr Thr Thr Thr Ala Ala Ala Ala Glu Pro Ser Ala
            325                 330                 335

Ser Ala Pro Ala Pro Ser Gly Asn Ser Ala Ser Gly Ser Asn Pro Leu
            340                 345                 350

Tyr Ala Gln Cys Gly Gly Leu Asn Phe Lys Gly Ala Ser Gly Cys Val
            355                 360                 365

Ala Gly Ala Thr Cys Lys Lys Met Asn Pro Tyr Tyr Ser Gln Cys Val
            370                 375                 380

Ser Ala
385
```